United States Patent
Novak et al.

(10) Patent No.: US 10,933,091 B1
(45) Date of Patent: Mar. 2, 2021

(54) COMPOSITION AND METHOD FOR THE TREATMENT OF TYPE I DIABETES

(71) Applicant: Vector Vitale IP LLC, North Miami Beach, FL (US)

(72) Inventors: Peter Novak, Sunny Isles Beach, FL (US); Maxim Temnikov, Miami, FL (US); Oleksandr Balakin, Dnepropetrovsk (UA)

(73) Assignee: Vector Vitale IP LLC, North Miami Beach, FL (US)

( * ) Notice: Subject to any disclaimer, the term of this patent is extended or adjusted under 35 U.S.C. 154(b) by 0 days.

(21) Appl. No.: 16/722,295

(22) Filed: Dec. 20, 2019

(51) Int. Cl.
*A61K 33/30* (2006.01)
*A61K 9/00* (2006.01)
*A61K 9/08* (2006.01)

(52) U.S. Cl.
CPC ............ *A61K 33/30* (2013.01); *A61K 9/0019* (2013.01); *A61K 9/0053* (2013.01); *A61K 9/08* (2013.01)

(58) Field of Classification Search
CPC .... A61K 33/30; A61K 9/0019; A61K 9/0053; A61K 9/08
See application file for complete search history.

(56) References Cited

U.S. PATENT DOCUMENTS

| | | | |
|---|---|---|---|
| 4,195,094 A * | 3/1980 | Fox, Jr. | C07D 285/135 514/494 |
| 8,512,676 B1 | 8/2013 | Eghbalnia et al. | |
| 8,753,889 B1 | 6/2014 | Roeder | |
| 9,861,659 B2 | 1/2018 | Novak et al. | |
| 10,183,041 B2 | 1/2019 | Novak et al. | |
| 10,226,484 B2 | 3/2019 | Novak et al. | |
| 2003/0068351 A1 | 4/2003 | Roig | |
| 2003/0118713 A1 | 6/2003 | Bjorkstrom et al. | |
| 2004/0013732 A1 | 1/2004 | Farber et al. | |
| 2007/0207191 A1 | 9/2007 | Kanzer et al. | |
| 2015/0056297 A1 | 2/2015 | Liu | |
| 2016/0151415 A1 | 6/2016 | Novak et al. | |
| 2016/0153957 A1 | 6/2016 | Novak et al. | |
| 2018/0055879 A1* | 3/2018 | Novak | A61K 2300/00 |

FOREIGN PATENT DOCUMENTS

WO 0182871 A2 11/2001
WO 2006072054 A1 7/2006

OTHER PUBLICATIONS

Jayawardena et al. (Diabetic metabolic syndrome2012, 4(13) 11 pages.*
Anyakundo et al (EC Nutrition 8.6 (2017): 224-232.).*
Albarede, "Medical applications of the Cu, Zn, and S Isotope effects," Metallomics, Jul. 25, 2016, pp. 1056-1070.
CRC Handbook of Chemistry and Physics (49th ed. 1968), pp. 1-3.
IRMM, Institute for Reference Materials and Measurements: Certificate (Zinc isotopes), Jul. 2007, pp. 1-2.
Jefferson Lab: "It's Elemental", Zinc isotopes, Science Education, May 2017, pp. 1-3.
U.S. Department of Energy "Products and Services Isotope Catalog" 2014, pp. 1-10.
International Application No. PCT/US19/55770 filed Oct. 11, 2019, not yet published.
U.S. Appl. No. 16/692,584, filed Nov. 22, 2019, not yet published.
U.S. Appl. No. 16/722,167, filed Dec. 20, 2019, not yet published.
U.S. Appl. No. 16/722,225, filed Dec. 20, 2019, not yet published.
U.S. Appl. No. 16/722,249, filed Dec. 20, 2019, not yet published.
Nyenwe et al., "Management of Type 2 Diabetes; Evolving Strategies for the Treatment of Patients with Type 2 Diabetes," Metabolism, Jan. 2011, vol. 60 No. 1, pp. 1-43.
Office Action in U.S. Appl. No. 16/722,225 dated May 12, 2020.
Himoto et al.; "Associations between Zinc Deficiency and Metabolic Abnormalities in Patients with Chronic Liver Disease," (Jan. 14, 2018), MDPI; Nutrients, vol. 10, No. 88, pp. 1-17. (Year: 2018).
Pearlman et al.; "State of the art: treatment of nonalcoholic steatohepatits," (2014), Lipponcott Williams & Wilkins; Current Opinion in Gastroenterology, vol. 30, No. 3, pp. 223-237. (Year: 2014).
PubChem entry for "Zinc: Other Experimental Properties", retrieved from: <pubchem.ncbi.nlm.nih.gov/compound/23994#section=Other-Experimental-Properties&fullscreen=true> on Jun. 8, 2020, p. 1. (Year: 2020).
Office Action in U.S. Appl. No. 16/722,249 dated Jun. 26, 2020.

* cited by examiner

*Primary Examiner* — Shirley V Gembeh
(74) *Attorney, Agent, or Firm* — Liang & Hennessey LLP; Stanley D. Liang

(57) ABSTRACT

A method of treating type I diabetes comprising administering a therapeutically effective amount of $^{64}$Zn-enriched zinc.

11 Claims, 24 Drawing Sheets

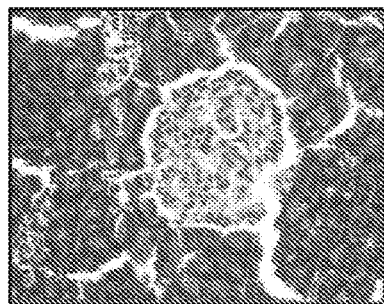
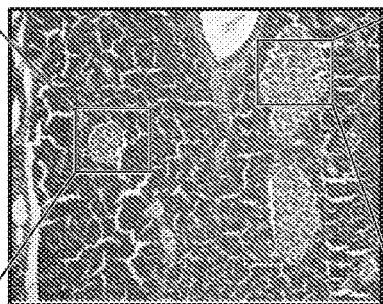
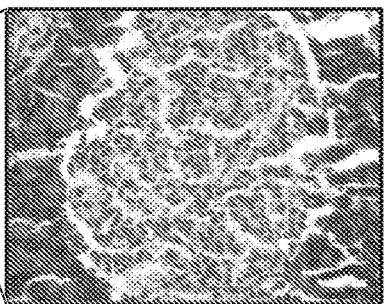
Control
FIG. 7A  FIG. 7B  FIG. 7C
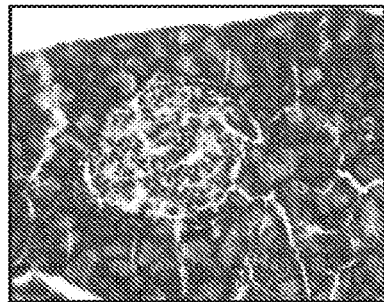
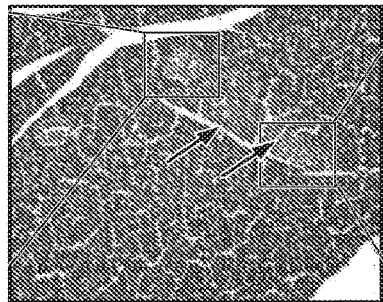
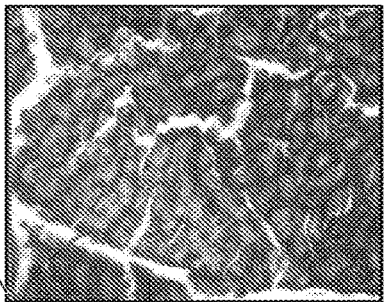
Obesity
FIG. 7D  FIG. 7E  FIG. 7F

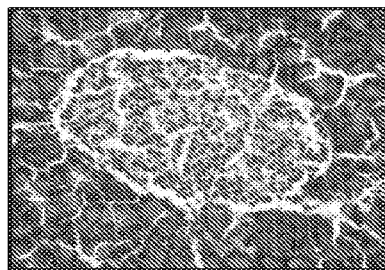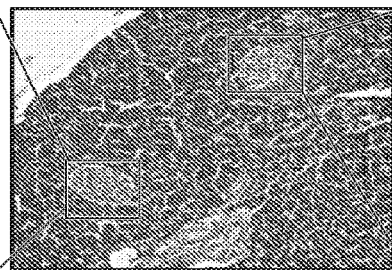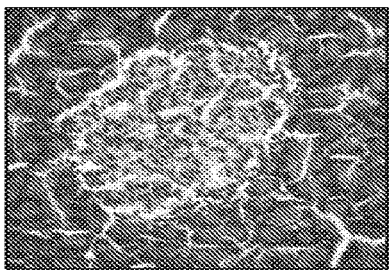
Control + Zn-64 stable isotope in aspartate form
FIG. 8A  FIG. 8B  FIG. 8C
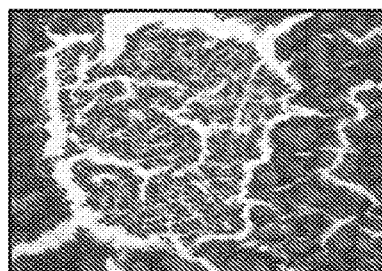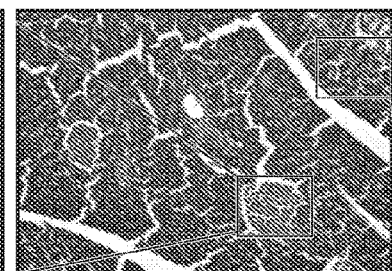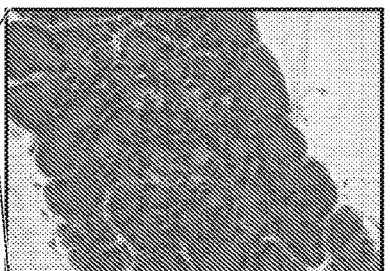
Obesity + Zn-64 stable isotope in aspartate form
FIG. 8D  FIG. 8E  FIG. 8F

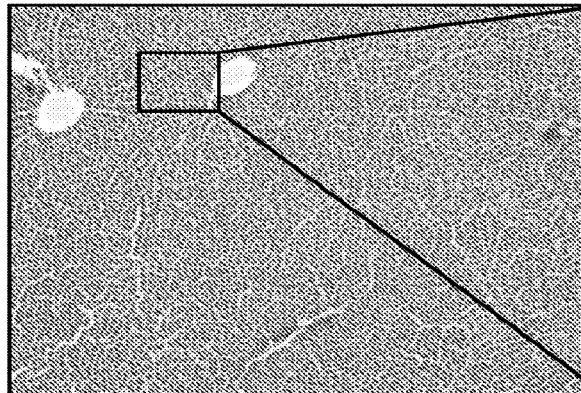
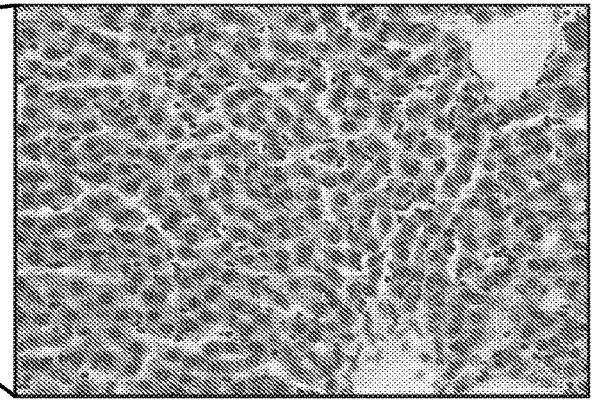
Control
FIG. 10A  FIG. 10B
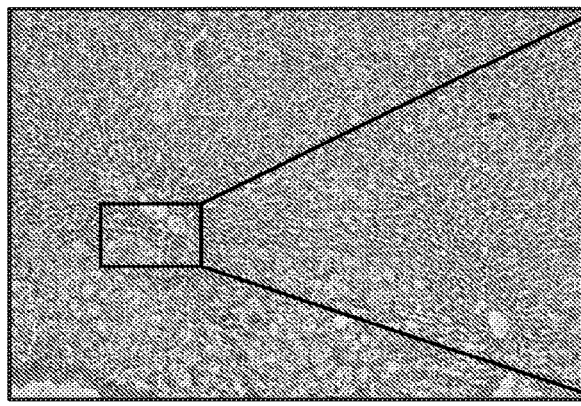
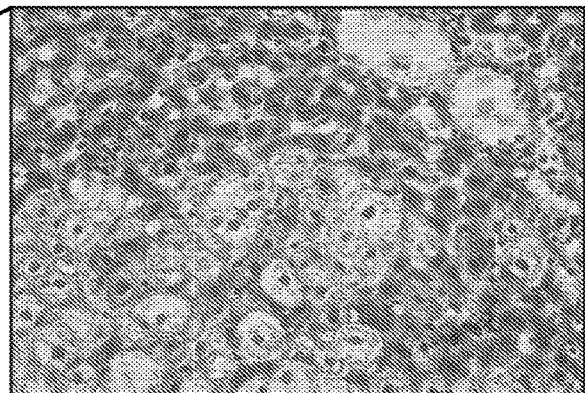
Obesity
FIG. 10C  FIG. 10D

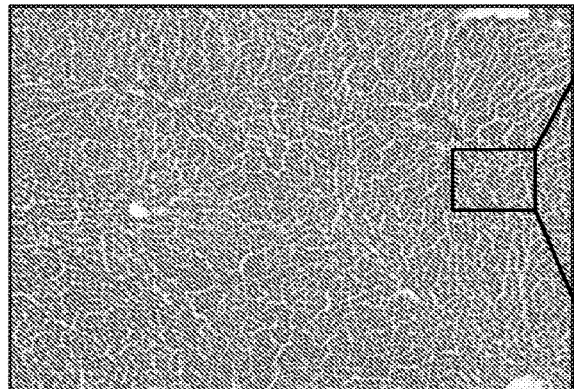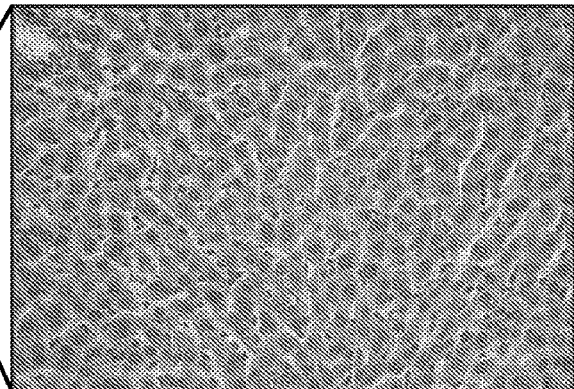
Control + Zn-64 stable isotope in aspartate form
FIG. 11A     FIG. 11B
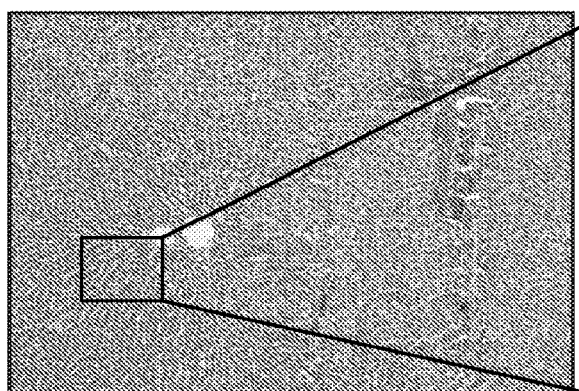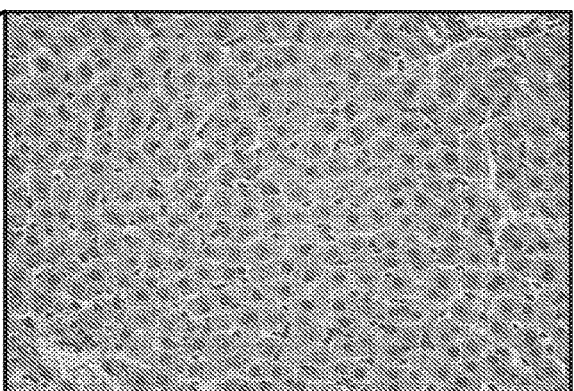
Obesity + Zn-64 isotope in aspartate form
FIG. 11C     FIG. 11D

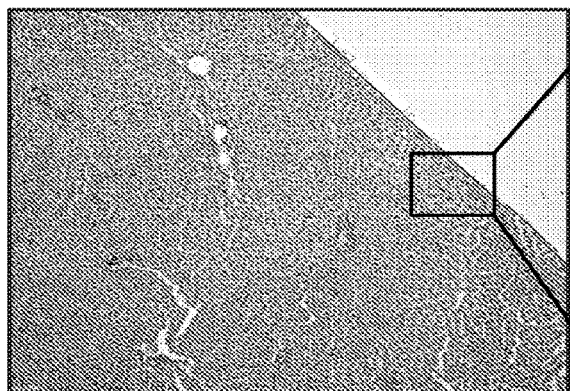 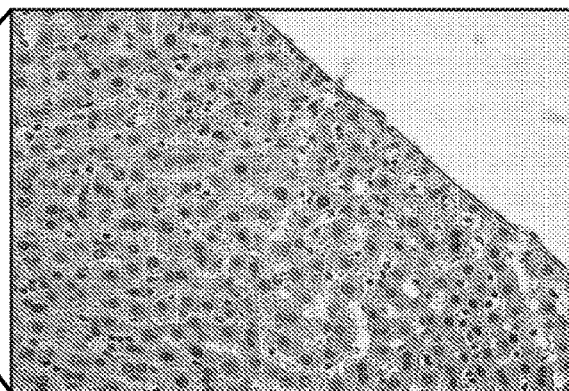
Control
FIG. 13A  FIG. 13B
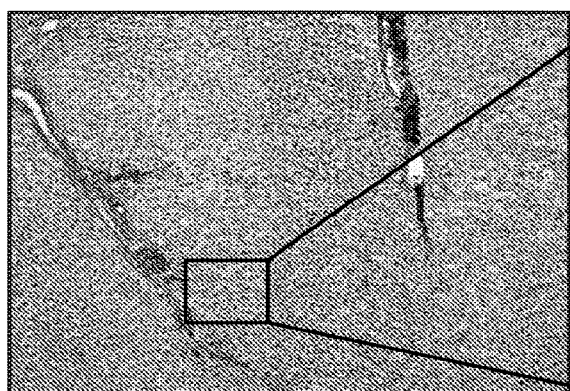 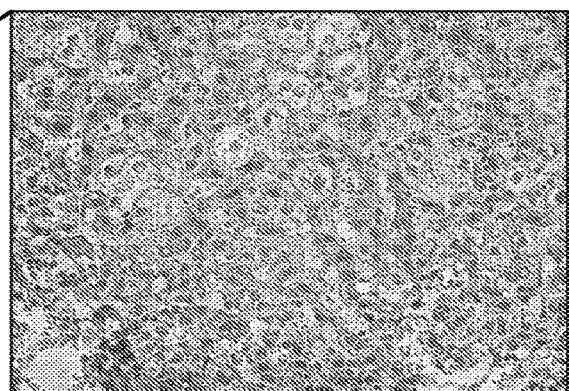
Obesity
FIG. 13C  FIG. 13D

Control + Zn-64 stable isotope in aspartate form

Obesity + Zn-64 stable isotope in aspartate form

Control (x10)

Control (x40)

Zn CHOOH (x10)

Zn CHOOH (x40)

Zn isotope (x10)

Zn isotope (x40)

Zn CHOOH (x10, x40)

Zn ISOTOpe (x10, x40)

COMPOSITION AND METHOD FOR THE TREATMENT OF TYPE I DIABETES

TECHNICAL FIELD

This disclosure relates to therapy of type I diabetes.

BACKGROUND

Type I diabetes (previously called insulin-dependent or juvenile diabetes) is usually diagnosed in children, teens, and young adults, but it can develop at any age. Patients with type I diabetes, does not make insulin or makes very little, insufficient amount of insulin.

SUMMARY

In one aspect, this disclosure provides a composition comprising zinc that is $^{64}$Zn-enriched zinc (the term "$^{64}$Zn$_e$" is used herein to refer to $^{64}$Zn-enriched zinc); the composition is provided at a therapeutically effective dose for treating type I diabetes. In another aspect, a method of use of said composition is provided. In some embodiments, the $^{64}$Zn-enriched zinc is in the form of a $^{64}$Zn$_e$ compound or a $^{64}$Zn$_e$ salt.

The disclosed compositions contain zinc that is enriched for $^{64}$Zn. In certain embodiments, the disclosed compositions contain zinc that is at least 80% $^{64}$Zn$_e$, at least 90% $^{64}$Zn$_e$, at least 95% $^{64}$Zn$_e$, or at least 99% $^{64}$Zn$_e$, for example, zinc that is 80% 64Zn$_e$, 85% 64Zn$_e$, 90% $^{64}$Zn$_e$, 95% $^{64}$Zn$_e$, 99% $^{64}$Zn$_e$, or 99.9% $^{64}$Zn$_e$.

The disclosed compositions may be administered to a subject to treat type I diabetes. The subject may be a human or a non-human mammal, such as a non-human primate or a domesticated dog or cat.

Numerous other aspects are provided in accordance with these and other aspects of the invention. Other features and aspects of the present invention will become more fully apparent from the following detailed description and the appended claims.

Note: 1—Control; 2—Control+$^{64}$Zn$_e$ stable isotope in aspartate form; 3—diet induced obesity+$^{64}$Zn$_e$ stable isotope in aspartate form; 4—Diet Induced Obesity.

Figure 3:
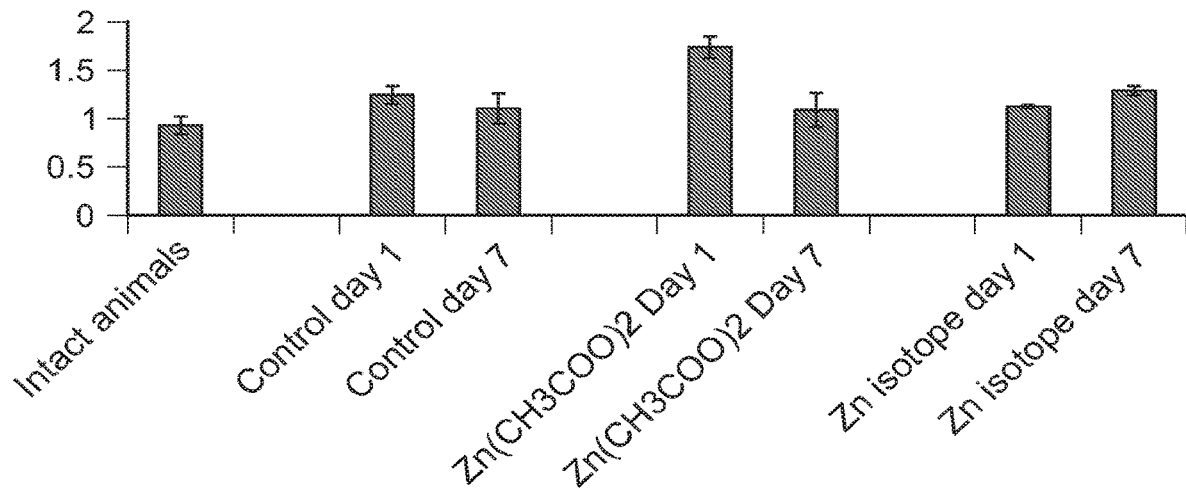

FIG. 3 shows insulin levels in the blood of experimental animals (M±n, n=10).

Figure 4:
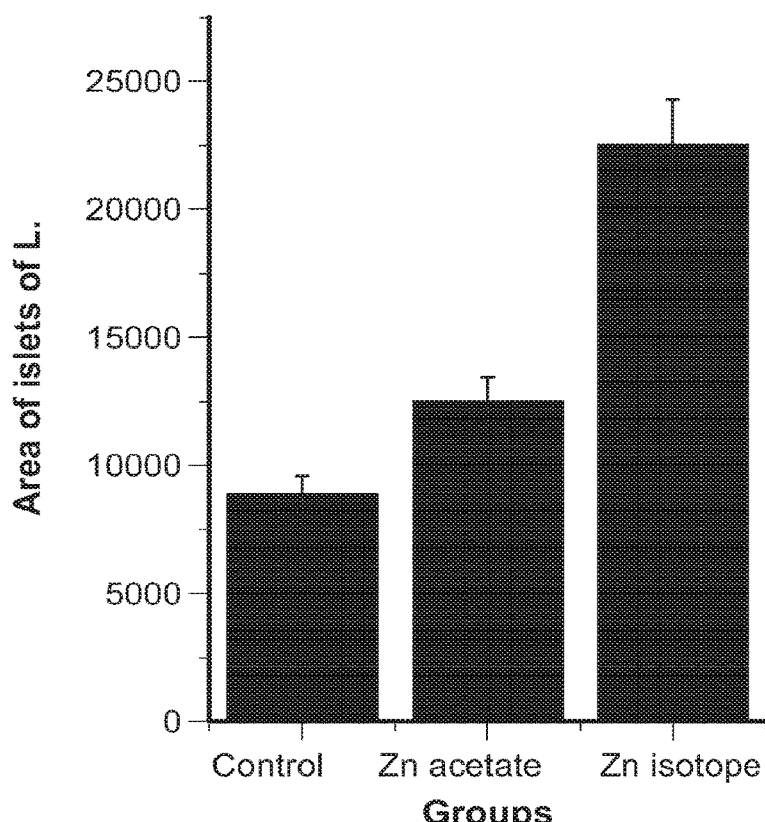

FIG. 4 shows pancreatic islet area of experimental animals (M±n, n=10).

Figure 5:
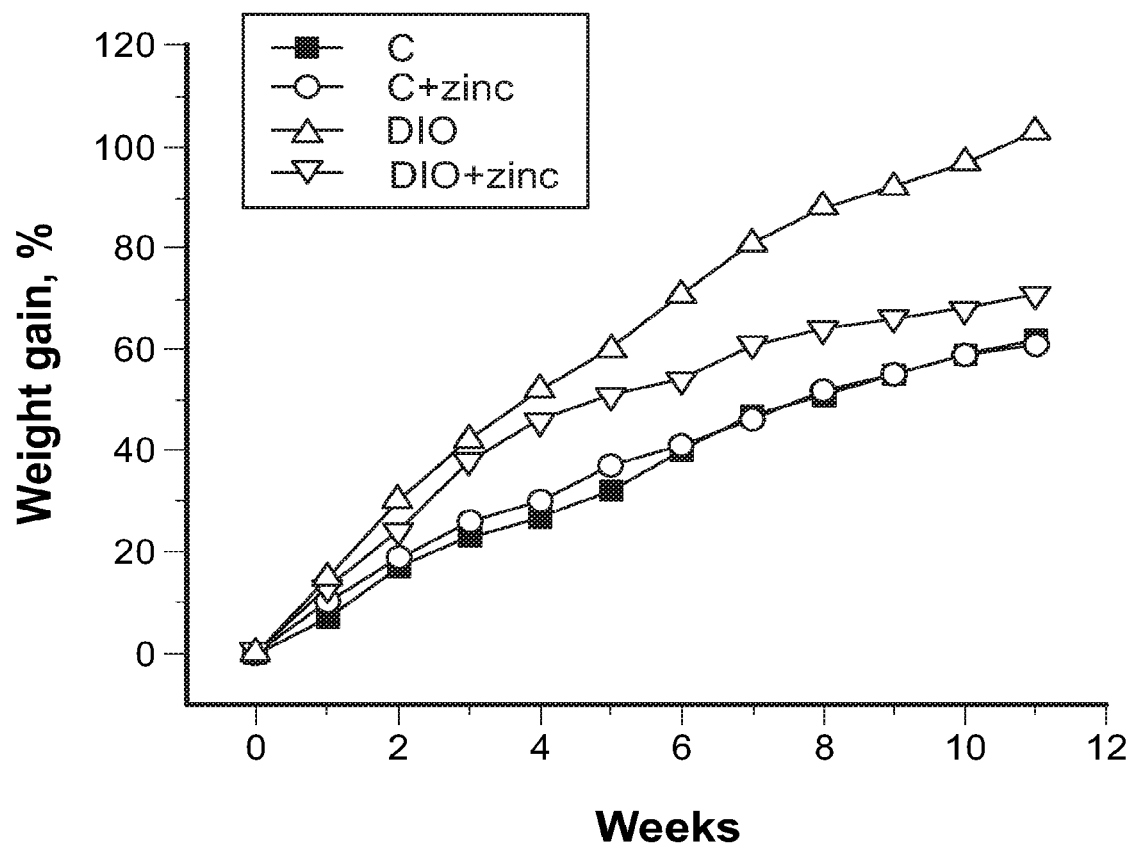

FIG. 5 shows Dynamics of increase in body weight of animals in experimental groups (M±n, n=10).

Note: C—control; C+zinc—control on the background of administration of Zn-64 stable isotope in aspartate form; DIO—diet induced obesity; DIO+zinc—diet induced obesity on the background of administration of Zn-64 stable isotope in aspartate form.

Figure 6:
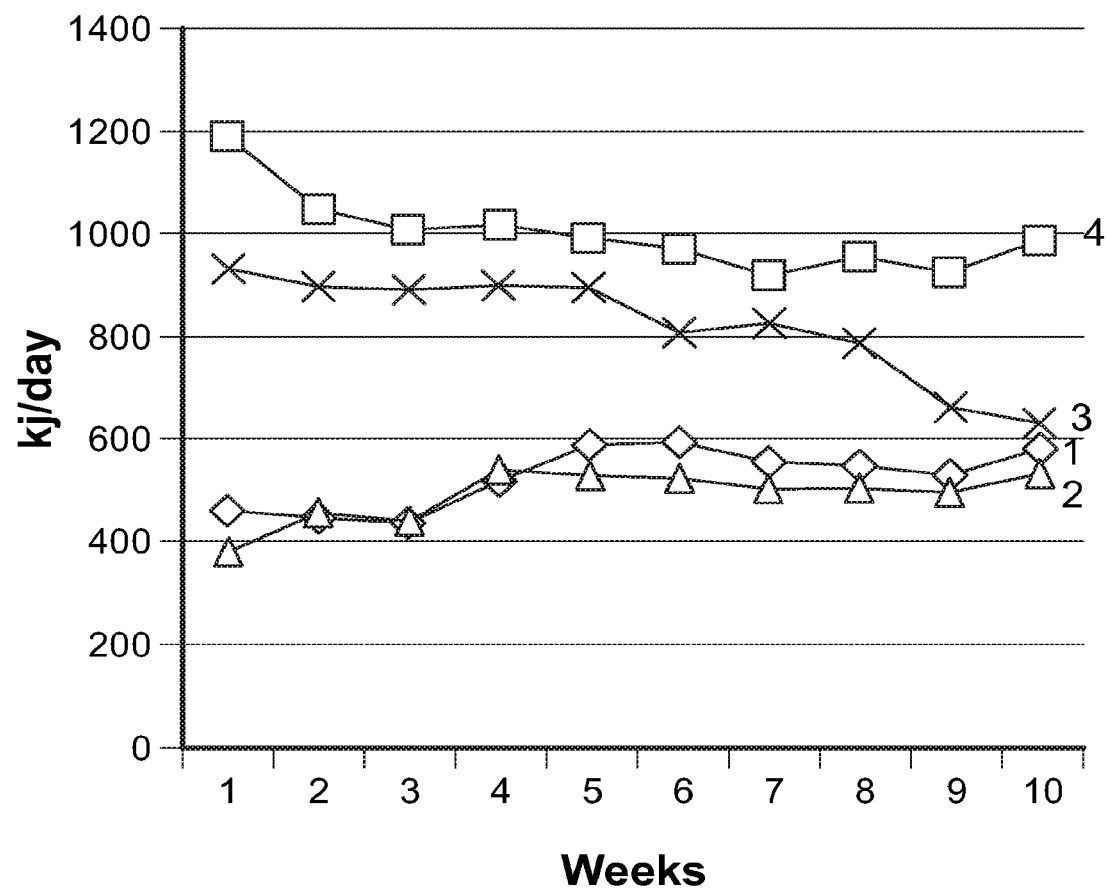

FIG. 6 shows Caloric content of food consumed by animals of experimental groups (M±n, n=10).

Note: 1—Control; 2—Control+Zn-64 stable isotope in aspartate form; 3—Obesity+Zn-64 stable isotope in aspartate form; 4—Obesity.

FIG. 7A-FIG. 7F show micrographs of sections of pancreas in animals from the control (FIG. 7A-FIG. 7C) and obesity (FIG. 7D-FIG. 7F) groups, hematoxylin & eosin, arrows show exocrine cells with marked fatty degeneration, eye. 10× obj. 10, eye. 10× obj. 40.

FIG. 8A-FIG. 8F show micrographs of sections of pancreas in animals from the control group (FIG. 8A-FIG. 8C) treated with Zn-64 stable isotope in aspartate form and animals from the obesity group (FIG. 8D-FIG. 8F) treated with Zn-64 stable isotope in aspartate form, hematoxylin & eosin, eye. 10× obj. 10, eye. 10× obj. 40.

Figure 9:
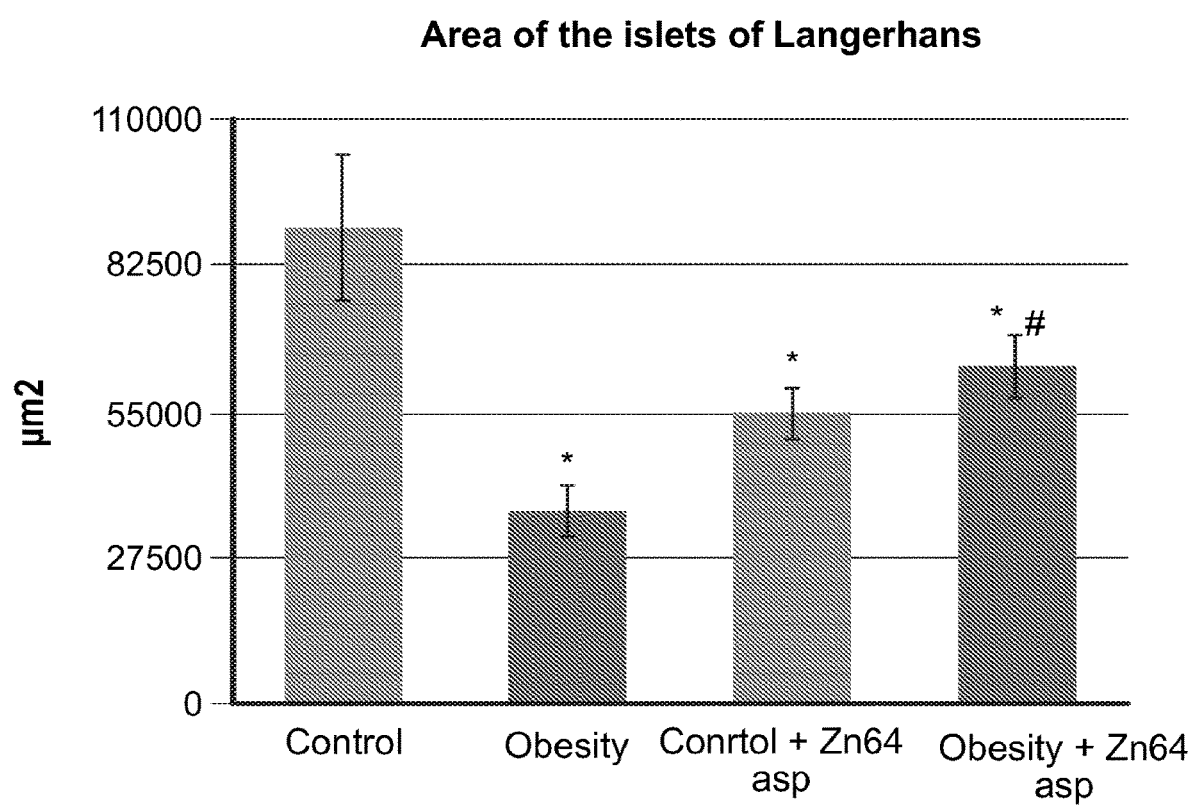

FIG. 9 shows cross-sectional surface area of the islets of Langerhans.

*—the difference between the control and experimental groups is significant when p≤0.05; #—the difference between the obesity group and obesity group treated with Zn-64 stable isotope in aspartate form is significant when p≤0.05.

FIG. 10A-FIG. 10D show micrographs of sections of liver in animals from the control (FIG. 10A and FIG. 10B) and obesity (FIG. 10C and FIG. 10D) groups, hematoxylin & eosin, eye. 10× obj. 10, eye. 10× obj. 40.

FIG. 11A-FIG. 11D show micrographs of sections of liver in animals from the control (FIG. 11A and FIG. 11B) and obesity (FIG. 11C and FIG. 11D) groups, all animals treated with Zn-64 stable isotope in aspartate form, hematoxylin & eosin, eye. 10× obj. 10, eye. 10× obj. 40.

Figure 12A:
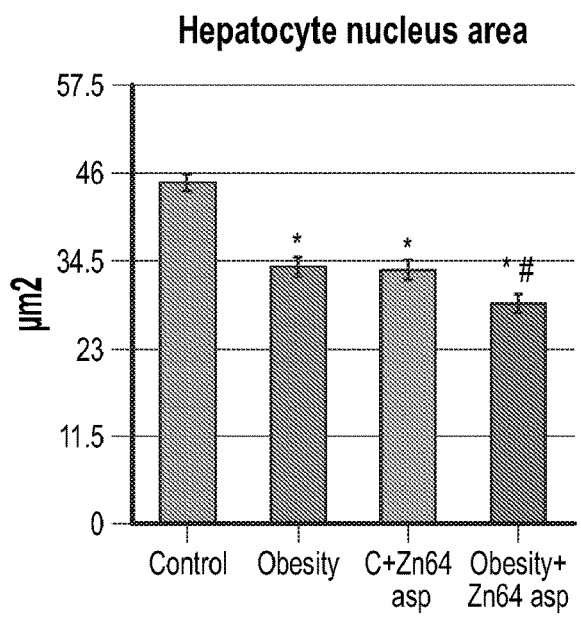
Figure 12B:
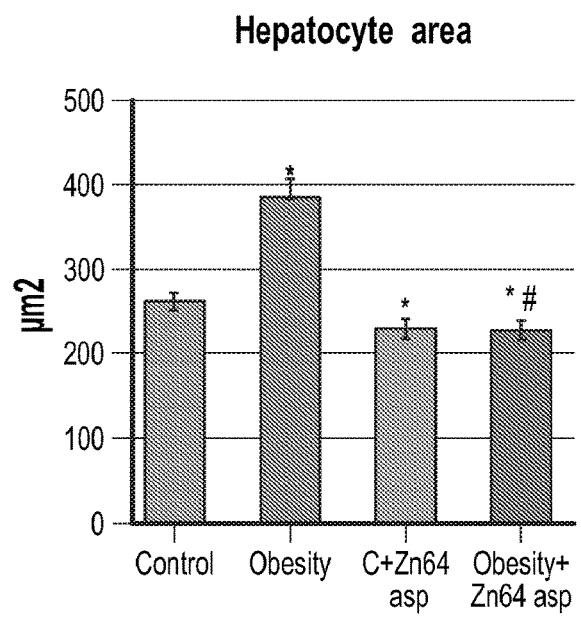
Figure 12C:
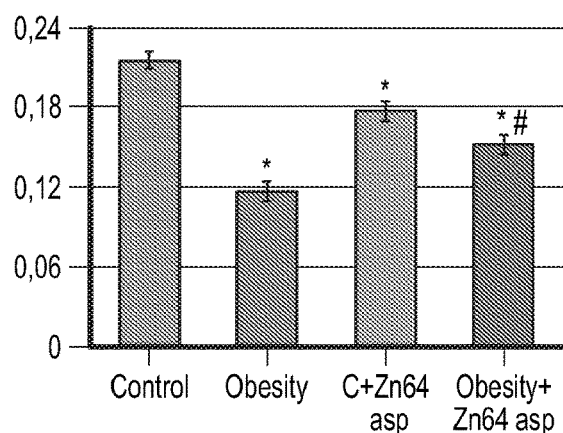
Figures 14A, 14B:
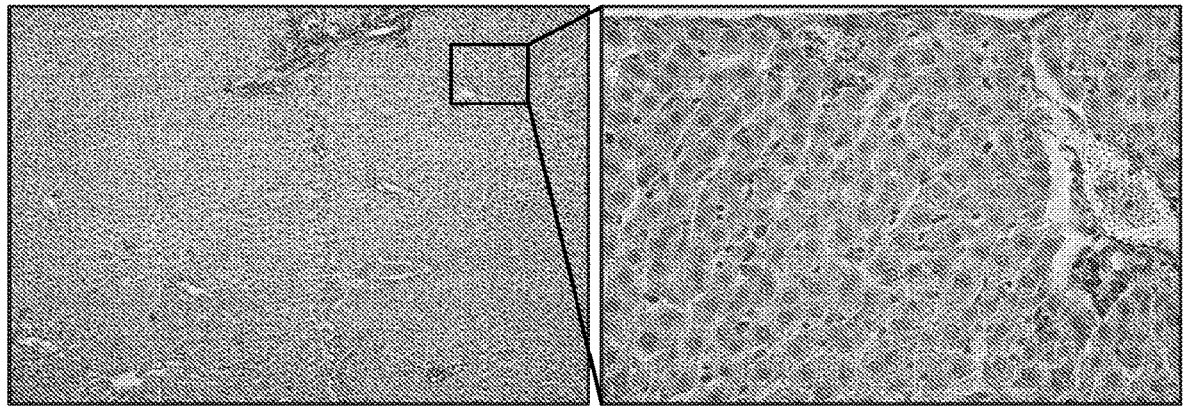
Figures 14C, 14D:
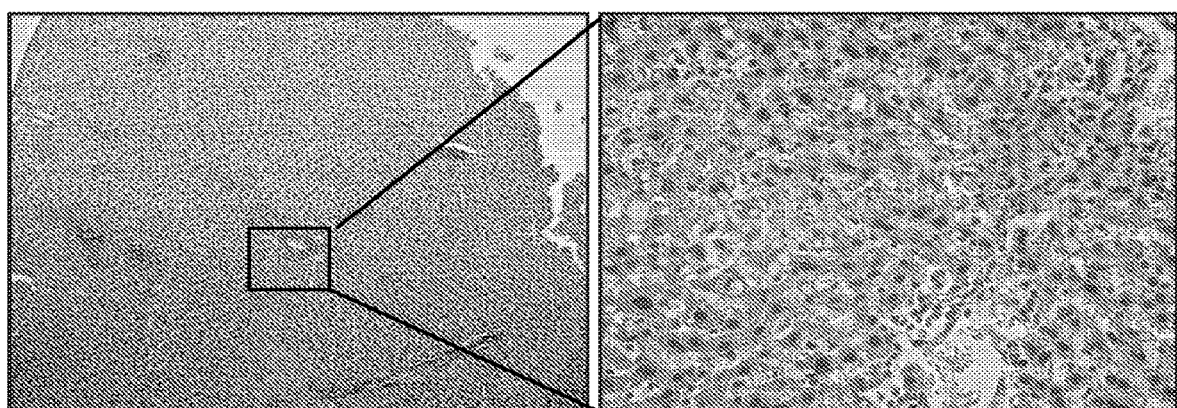

FIG. 12A (hepatocyte nucleus area), FIG. 12B (hepatocyte area), and FIG. 12C (nucleus-to-cytoplasm ratio of hepatocytes) show morphological analysis of the liver.

*—the difference between the control and experimental groups is significant when p≤0.05; #—the difference between the obesity group and obesity group treated with Zn-64 stable isotope in aspartate form is significant when p≤0.05.

FIG. 13A-FIG. 13D show micrographs of sections of liver in animals from the control (FIG. 13A and FIG. 13B) and obesity (FIG. 13C and FIG. 13D) groups, Van Gieson's staining method for the detection of collagen fibers (fibrosis) eye. 10× obj. 10, eye. 10× obj. 40.

FIG. 14A-FIG. 14D show micrographs of sections of liver in animals from the control (FIG. 14A and FIG. 14B) and obesity (FIG. 14C and FIG. 14D) groups, all animals treated with Zn-64 stable isotope in aspartate form, Van Gieson's stainin method for the detection of collagen fibers (fibrosis), eye. 10× obj. 10, eye. 10× obj. 40.

Figure 15:
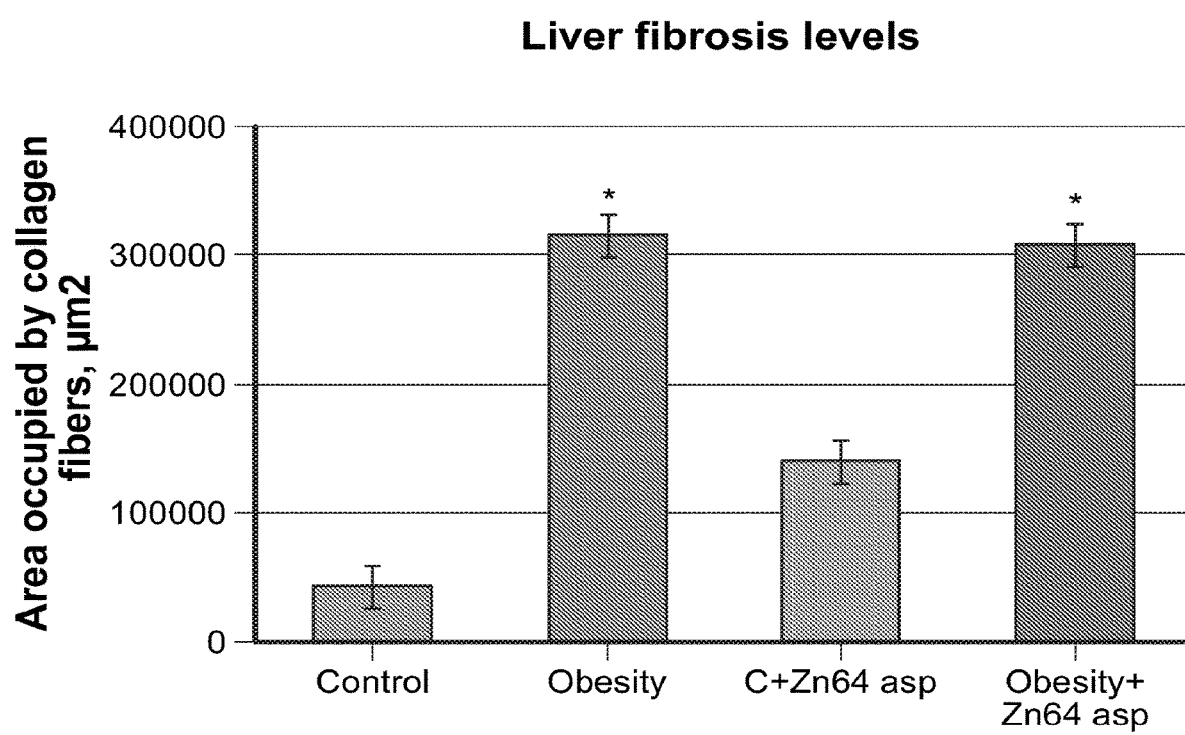

FIG. 15 shows morphometric analysis of liver fibrosis.
*—the difference between the control and experimental groups is significant when p≤0.05; #—the difference between the obesity group and obesity group treated with Zn-64 stable isotope in aspartate form is significant when p≤0.05.

Figure 16A:
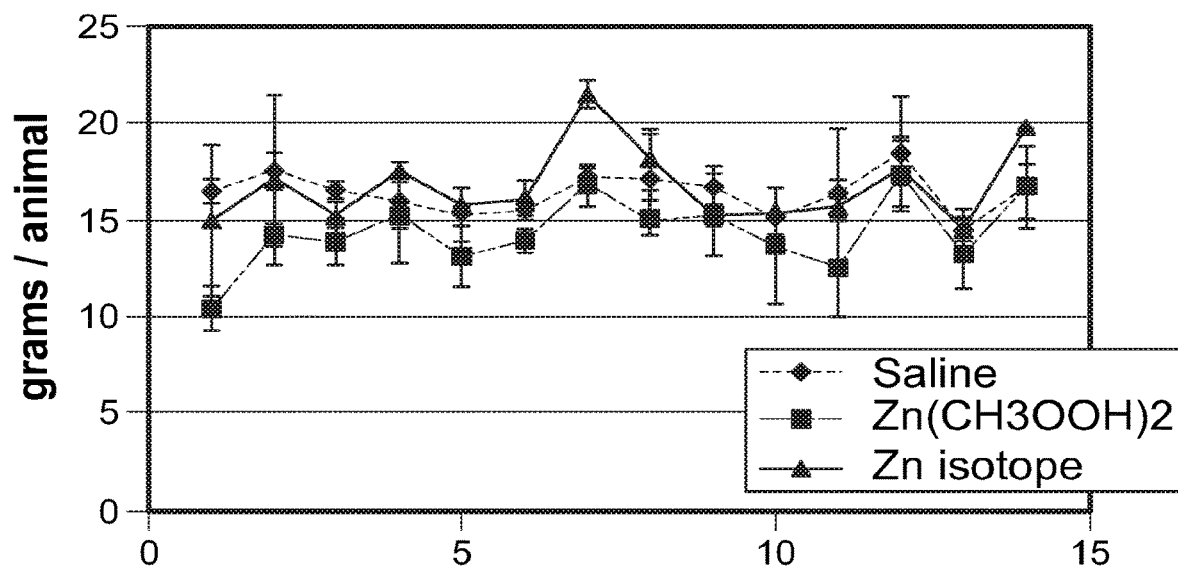
Figure 16B:
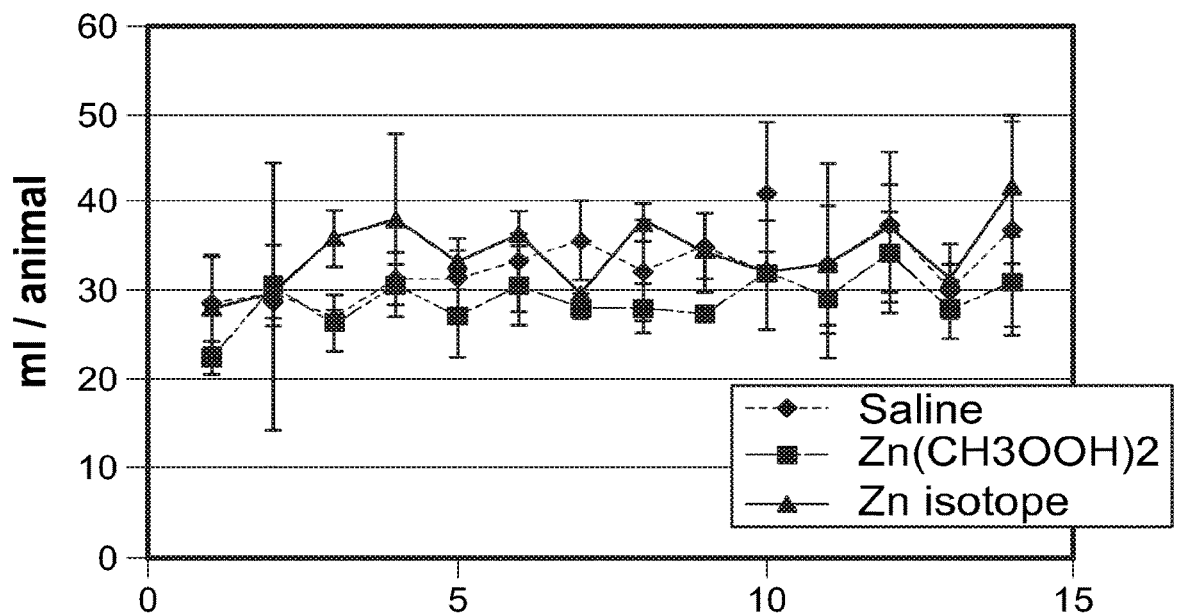
Figure 16C:
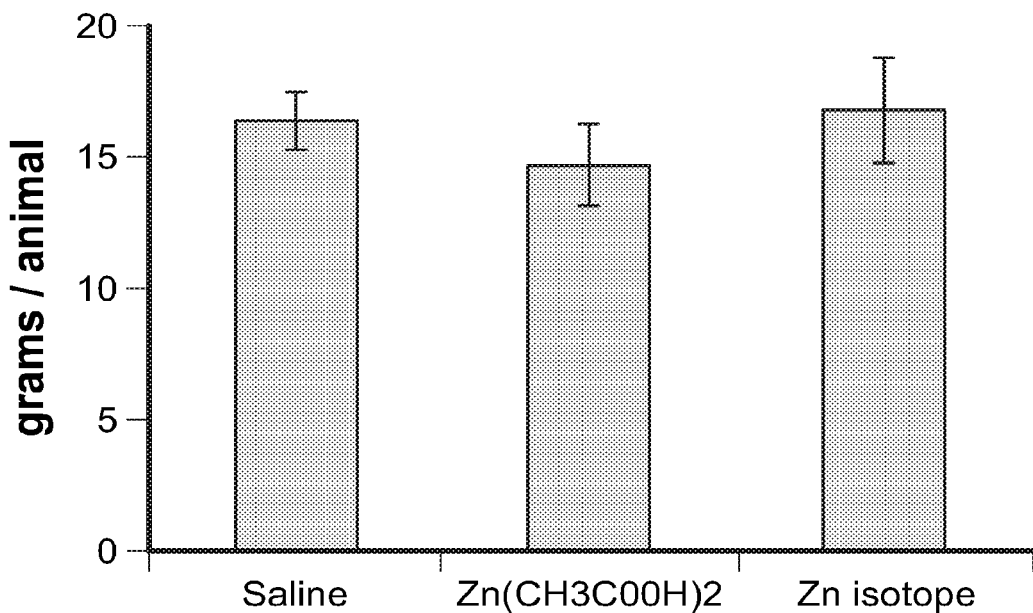
Figure 16D:
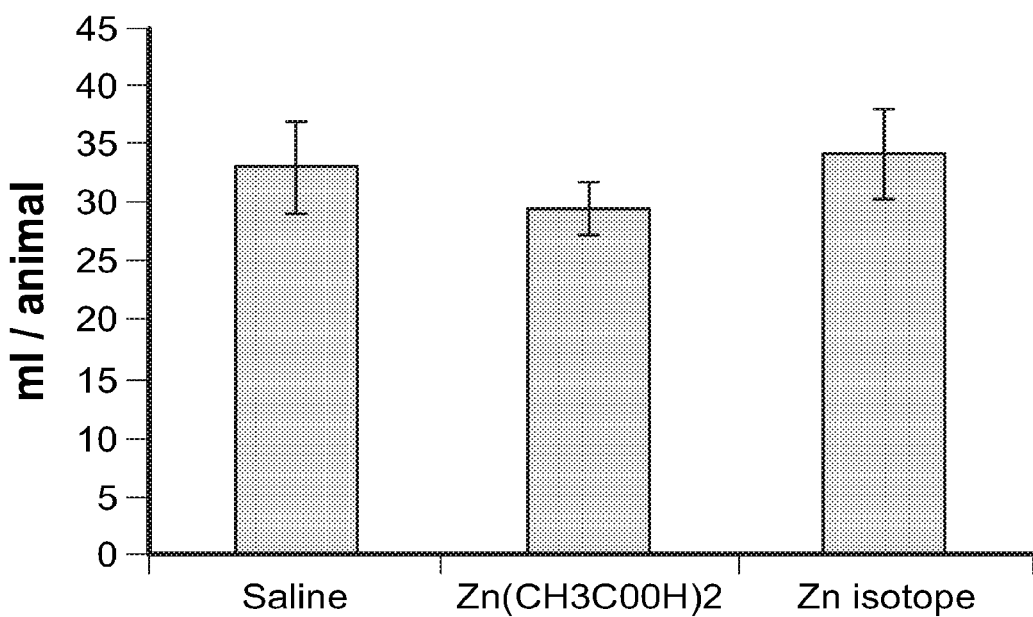
Figure 16E:
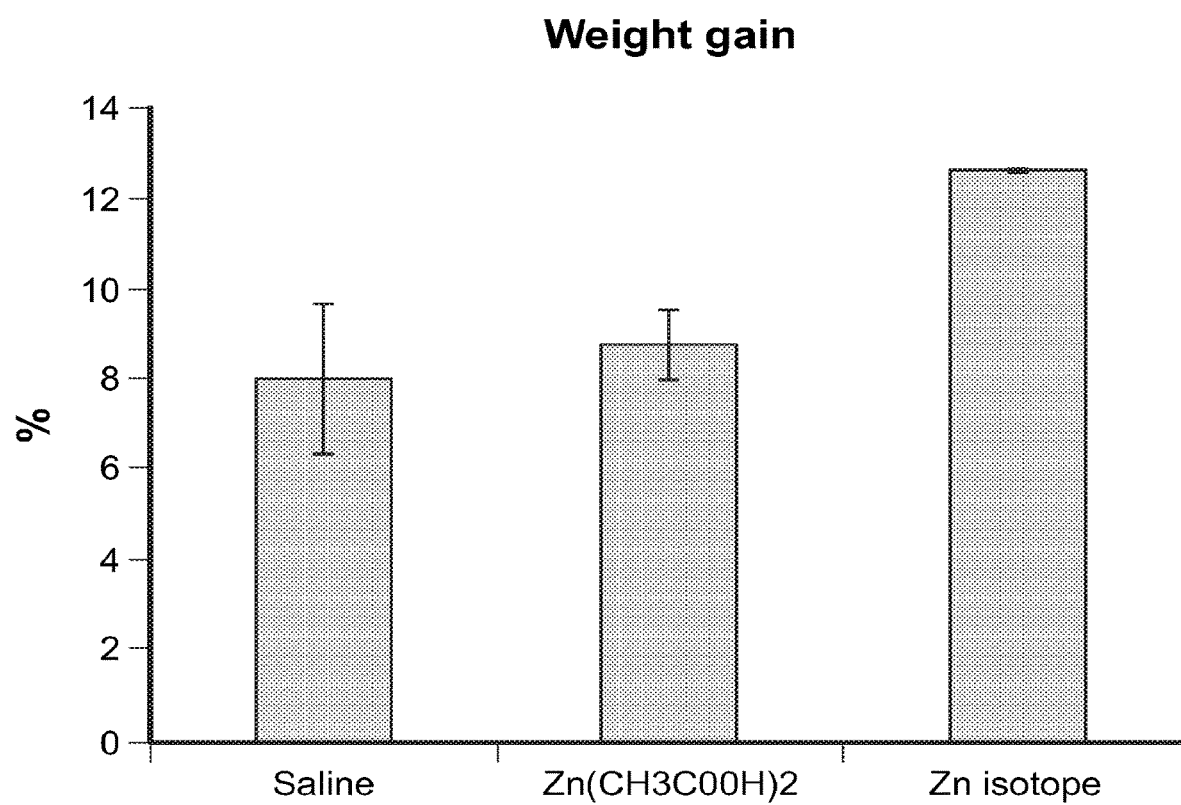

FIG. 16A-FIG. 16E show analysis of body weight, food and water consumption by experimental groups of animals. FIG. 16A Food consumption rates in grams per animal; FIG. 16B Water consumption rates in ml per 1 animal; FIG. 16C Average daily food consumption (during the experiment) per 1 animal; FIG. 16D Average daily water consumption (during the experiment) per 1 animal; FIG. 16E Weight gain in rats 2 weeks after drug administration.

Figure 17:
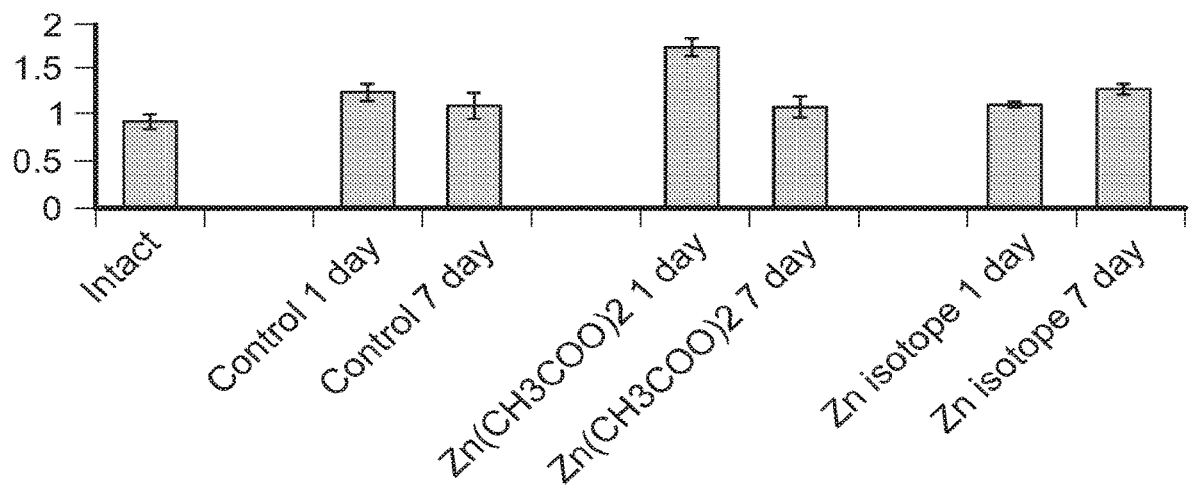

FIG. 17 is a graph showing serum insulin level (CU/mg of total protein).

Figure 18A:
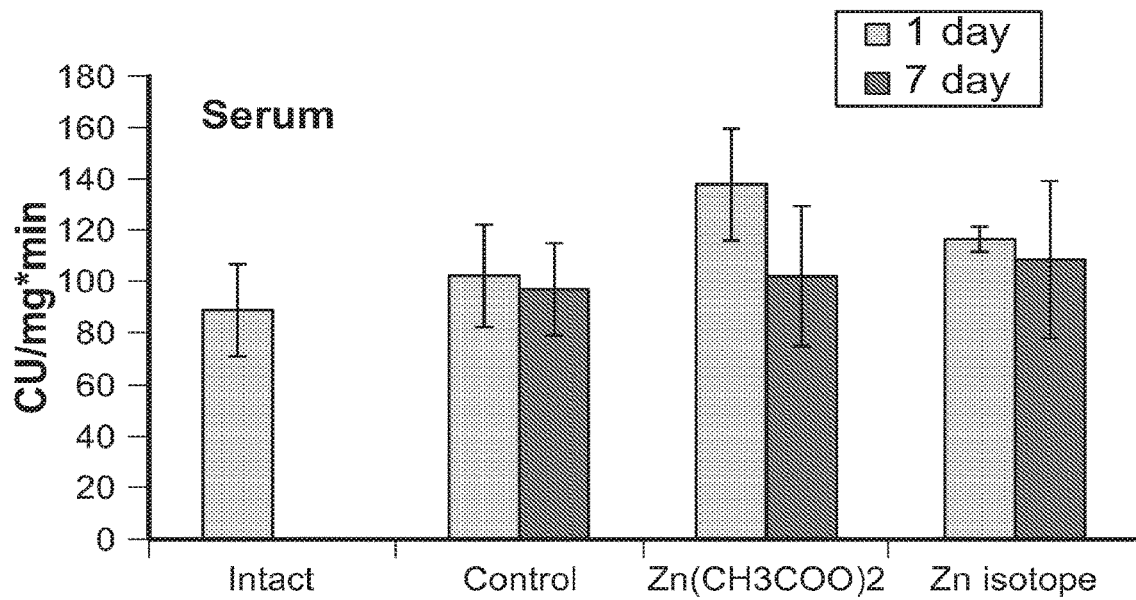
Figure 18B:
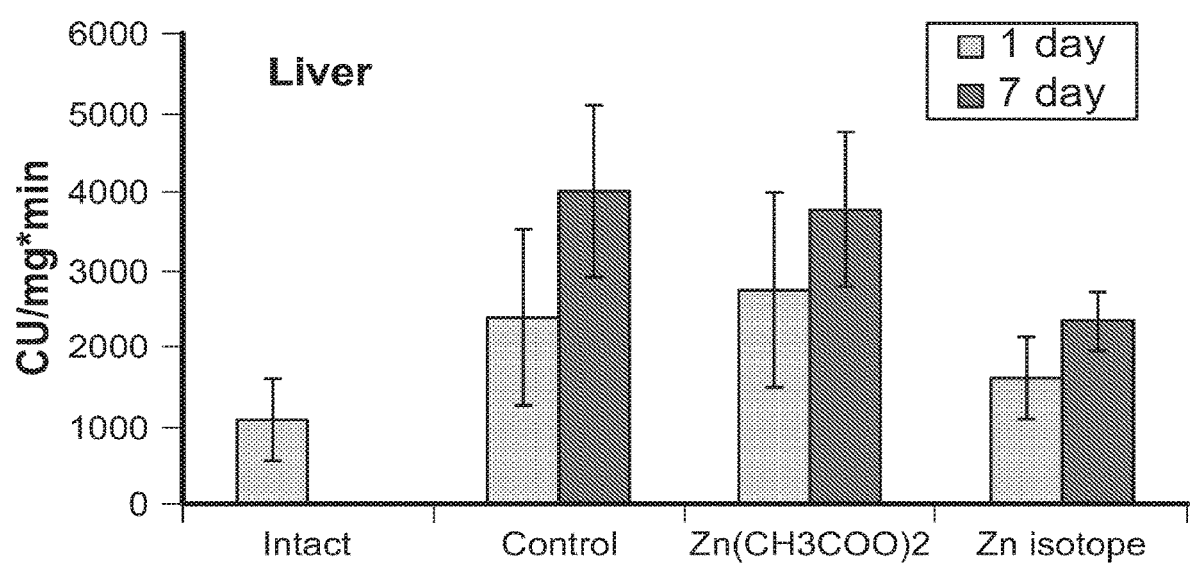

FIG. 18A (serum) and FIG. 18B (liver) are graphs showing superoxide dismutase activity (antioxidant Zn-dependent enzyme) CU/mg*min.

Figure 19:
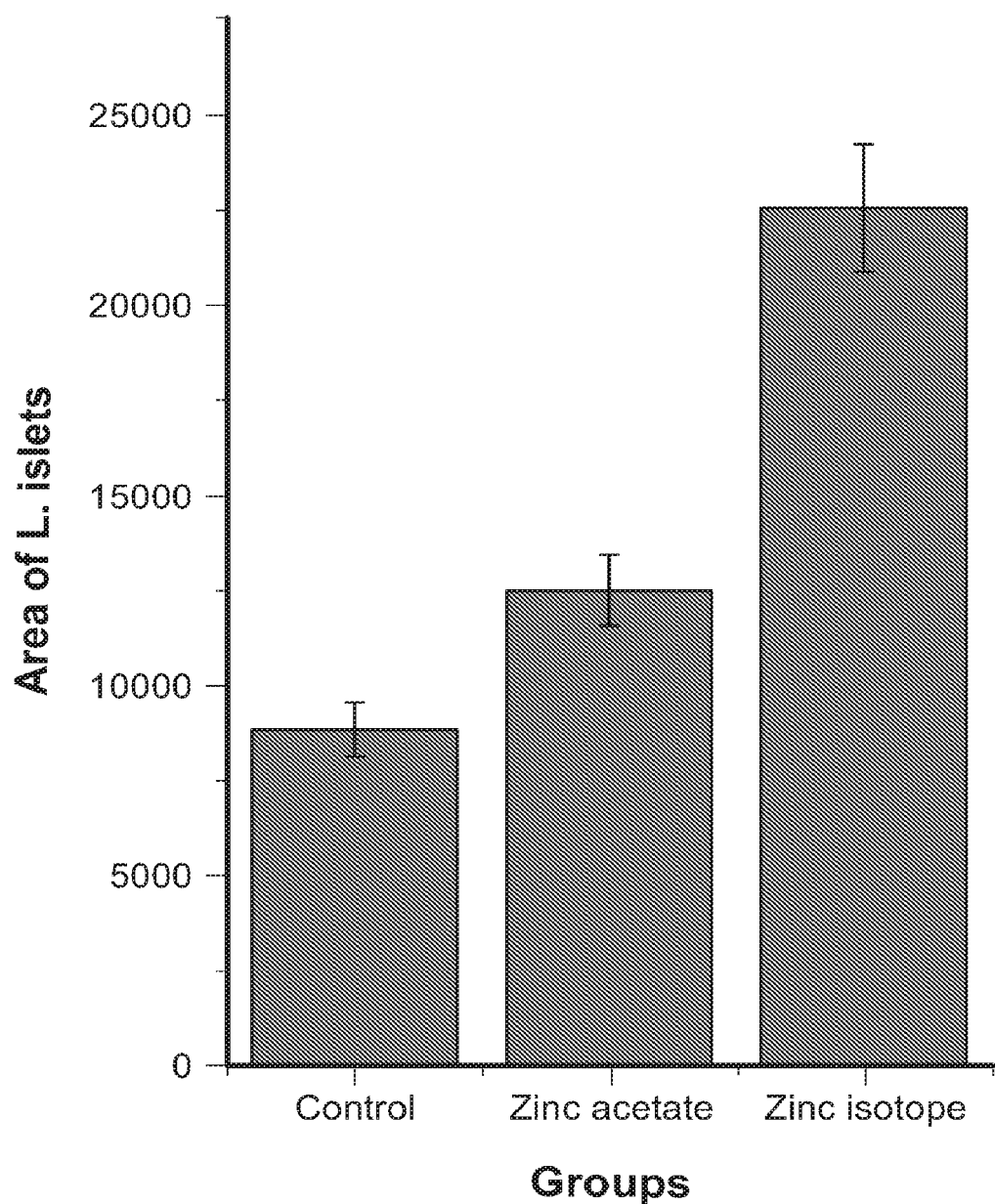

FIG. 19 is a graph showing measurement of the area of islets of Langerhans in the pancreas of laboratory animals (microscopically, at day 7 after the last administration of drugs).

Figure 20A:
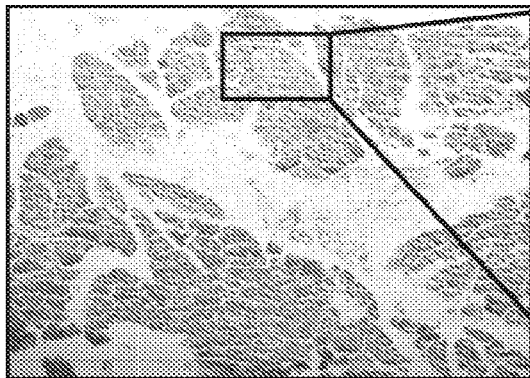
Figure 20B:
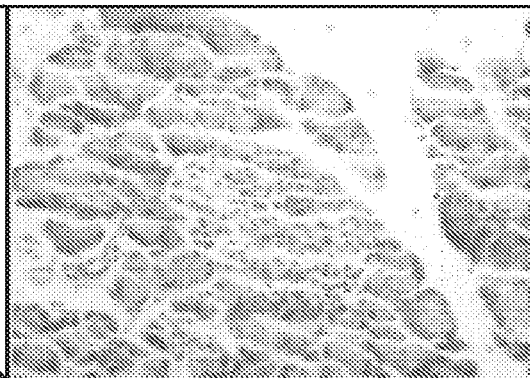
Figure 20C:
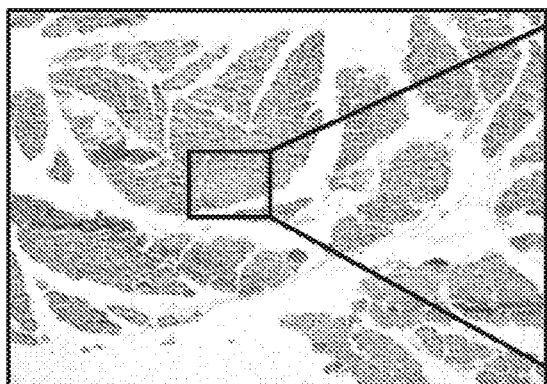
Figure 20D:
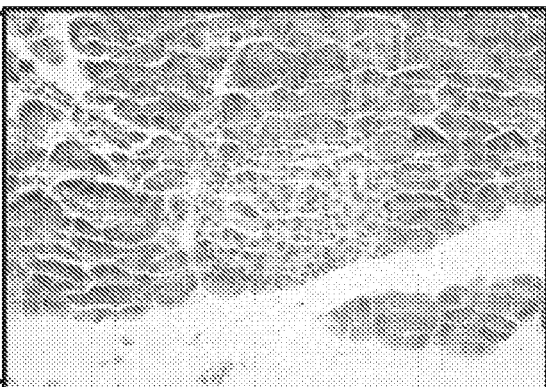
Figure 20E:
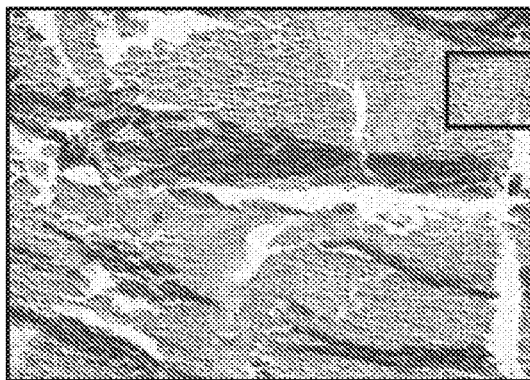
Figure 20F:
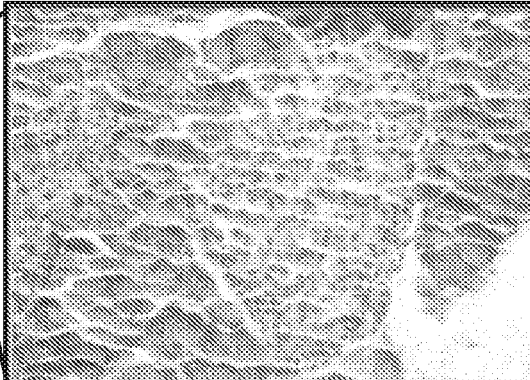

FIG. 20A-FIG. 20F are microscopic photos of the of islets of Langerhans. FIG. 20A and FIG. 20B—top panel; FIG. 20C and FIG. 20D—middle panel; FIG. 20E and FIG. 20F—bottom panel.

Figure 21A:
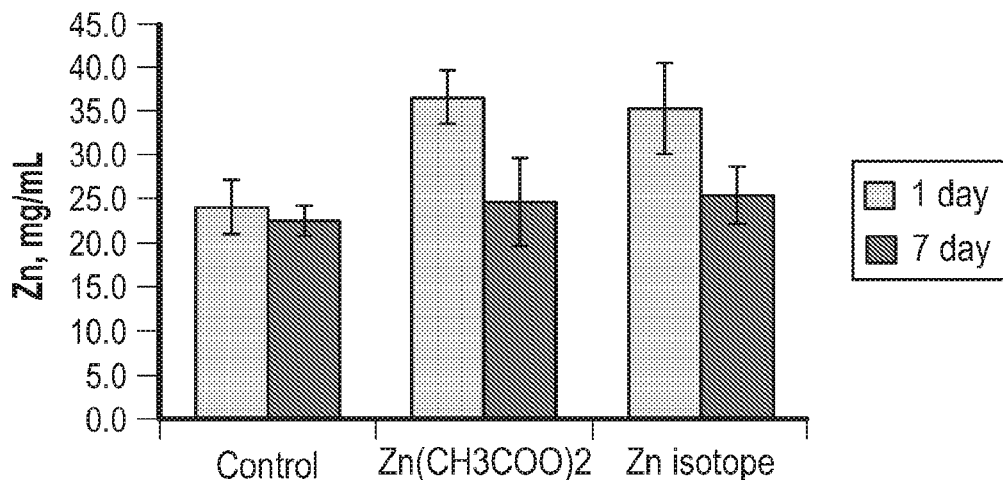
Figure 21B:
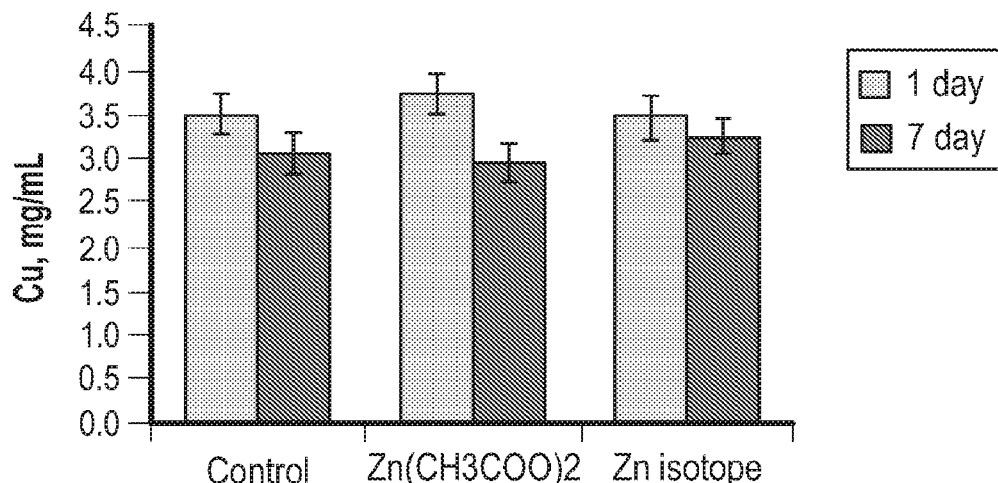
Figure 21C:
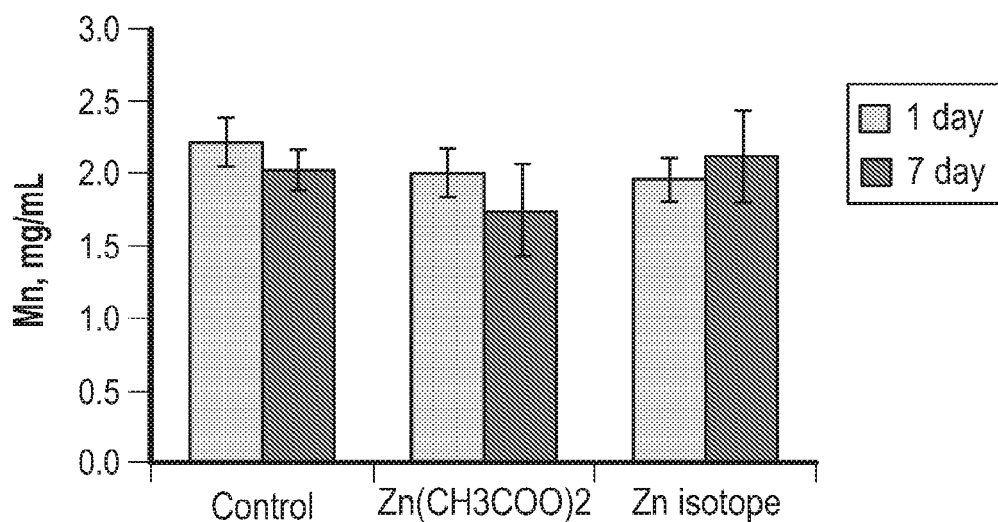

FIG. 21A-FIG. 21C shows accumulation of metals in liver tissues of laboratory animals.

Figure 22A:
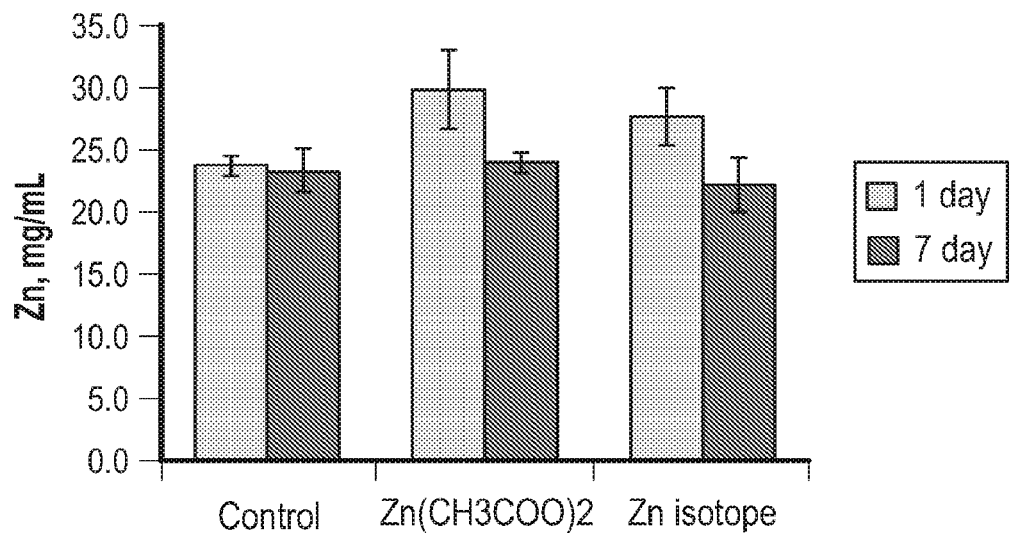
Figure 22B:
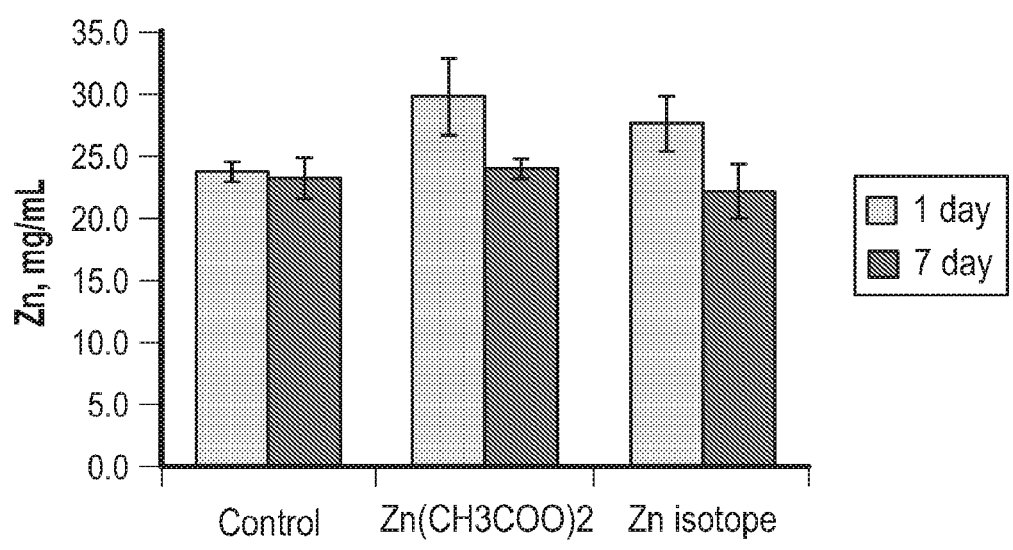
Figure 22C:
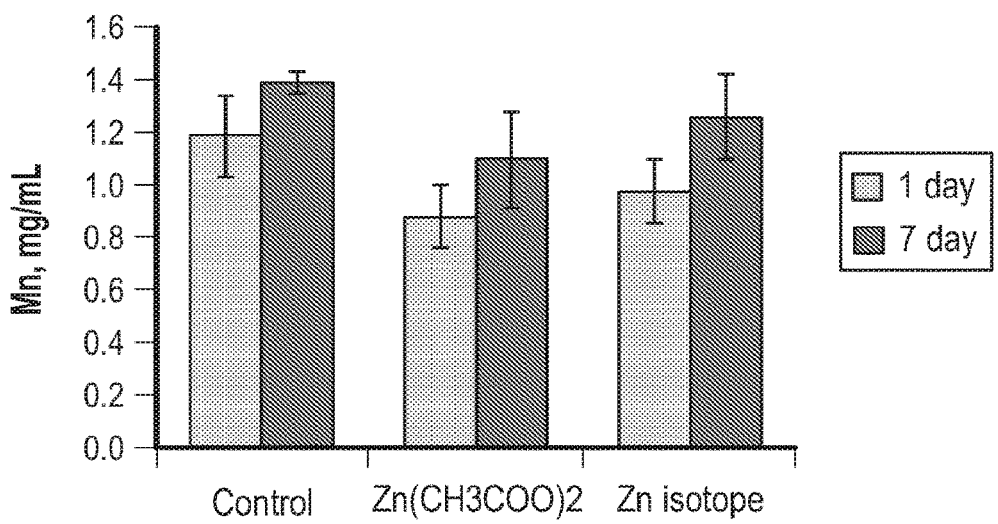

FIG. 22A-FIG. 22C shows accumulation of metals in kidney tissues of laboratory animals.

Figures 23A, 23B:
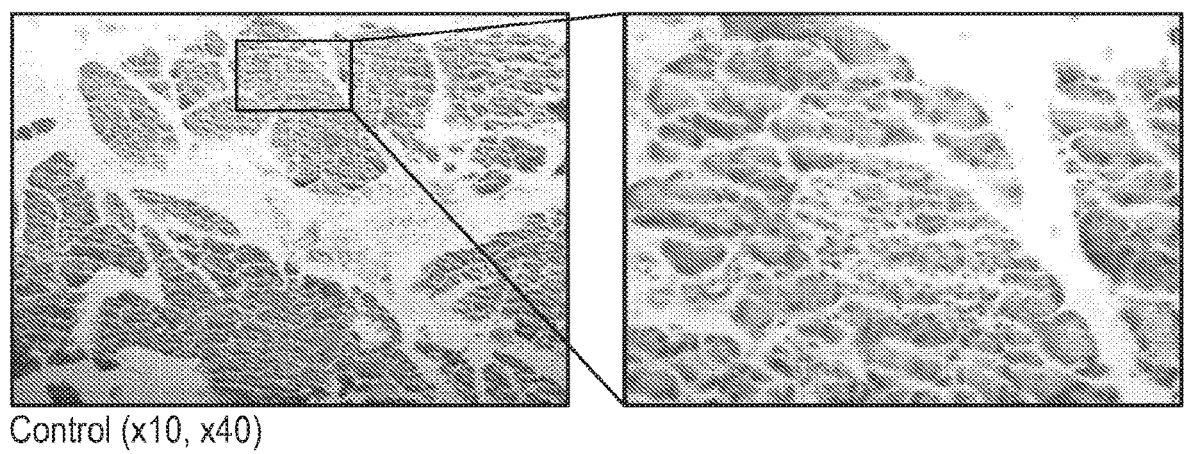
Figure 23C:
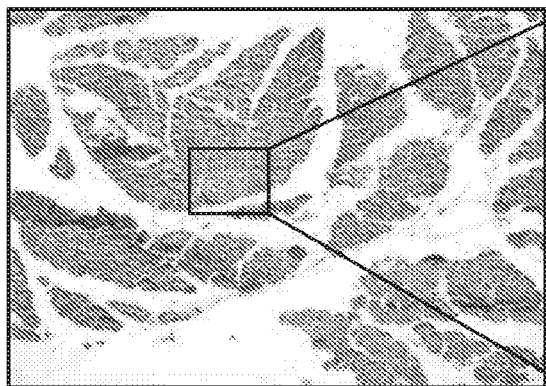
Figure 23D:
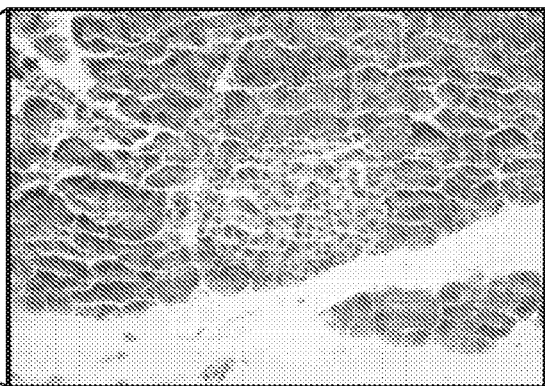
Figure 23E:
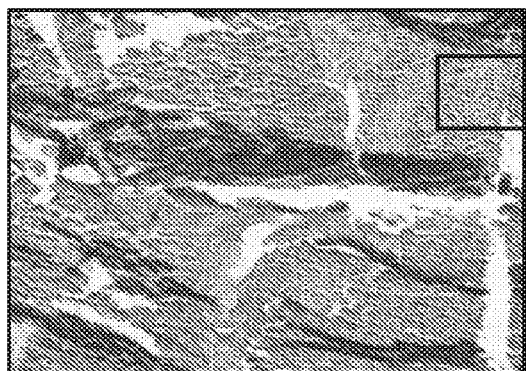
Figure 23F:
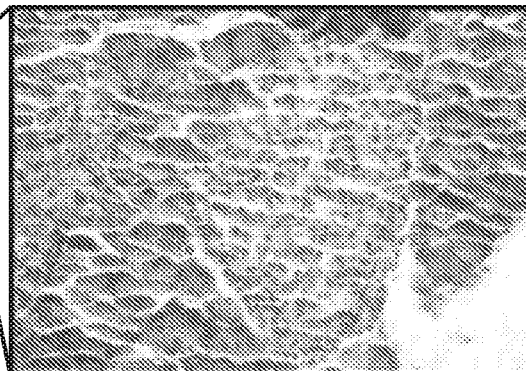

FIG. 23A-FIG. 23F are microscopic photos of the of islets of Langerhans, FIGS. 23A and 23B—control group, magnification ×10 and ×40, respectively, FIGS. 23C and 23D—zinc acetate, comparison group, magnification ×10 and ×40, respectively, FIGS. 23E and 23F—zinc isotope, therapeutic group, magnification ×10 and ×40, respectively.

DETAILED DESCRIPTION

As used herein, the word "a" or "plurality" before a noun represents one or more of the particular noun.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

"Effective amount," "prophylactically effective amount," or "therapeutically effective amount" refers to an amount of an agent or composition that provides a beneficial effect or favorable result to a subject, or alternatively, an amount of an agent or composition that exhibits the desired in vivo or in vitro activity. "Effective amount," "prophylactically effective amount," or "therapeutically effective amount" refers to an amount of an agent or composition that provides the desired biological, therapeutic, and/or prophylactic result. That result can be reduction, amelioration, palliation, lessening, delaying, and/or alleviation of one or more of the signs, symptoms, or causes of a disease, disorder or condition in a patient/subject, or any other desired alteration of a biological system. An effective amount can be administered in one or more administrations.

An "effective amount," "prophylactically effective amount," or "therapeutically effective amount" may be first estimated either in accordance with cell culture assays or using animal models, typically mice, rats, guinea pigs, rabbits, dogs or pigs. An animal model may be used to determine an appropriate concentration range and route of administration. Such information can then be used to determine appropriate doses and routes of administration for humans. When calculating a human equivalent dose, a conversion table such as that provided in *Guidance for Industry: Estimating the Maximum Safe Starting Dose in Initial Clinical Trials for Therapeutics in Adult Healthy Volunteers* (U.S. Department of Health and Human Services, Food and Drug Administration, Center for Drug Evaluation and Research (CDER), July 2005) may be used. The person of ordinary skill in the art is aware of additional guidance that may also be used to develop human therapeutic dosages based on non-human data. An effective dose is generally 0.01 mg/kg to 2000 mg/kg of an active agent, preferably 0.05 mg/kg to 500 mg/kg of an active agent. An exact effective dose will depend on the severity of the disease, patient's general state of health, age, body weight and sex, nutrition, time and frequency of administration, combination(s) of medicines, response sensitivity and tolerance/response to administration and other factors that will be taken into account by a person skilled in the art when determining the dosage and route of administration for a particular patient based on his/her knowledge of the art. Such dose may be determined by conducting routine experiments and at the physician's discretion. Effective doses will also vary depending on the possibility of their combined use with other therapeutic procedures, such as the use of other agents.

As used herein, a "patient" and a "subject" are interchangeable terms and may refer to a human patient/subject, a dog, a cat, a non-human primate, etc.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Type I Diabetes

Type I diabetes (previously called insulin-dependent or juvenile diabetes) is usually diagnosed in children, teens, and young adults, but it can develop at any age. Patients with type I diabetes, does not make insulin or makes very little, insufficient amount of insulin.

Type I diabetes is caused by an autoimmune reaction that destroys the cells in the pancreas that make insulin, called beta cells. There appears to be a genetic predisposition in some patients. Type I diabetes is treated with exogenous insulin.

Zinc

Zinc is attributed to the trace elements which are essential for ensuring a proper metabolic status of the human body. More than 200 enzymes throughout the body depend on zinc. This element is either a constituent of enzymes or a regulator of their activity covering all classes of enzymes: transferases (RNA and DNA polymerases, reverse transcriptase, thymidine kinase, nucleotidyl transferase, carboxypeptidase and other peptidases), hydrolases (alkaline phosphatase, 5-nucleotidase, aminopeptidase, etc.), lyases (aldolase, carbonic anhydrase, etc.), oxidoreductases (alcohol dehydrogenase, superoxide dismutase, etc.), ligases and isomerases. Without zinc, no protein, fat or carbohydrates metabolism is possible.

Zinc has also been proven to exhibit a mediated antioxidant effect. Zinc is an inhibitor of NADPH oxidase, an enzyme complex that catalyzes the production of highly aggressive superoxide anion radicals. In addition, it can have a direct effect on the oxidation of free radicals at the stage of initiation of chain reactions; it is a structural component of some enzymes of the antioxidant defense system, including Cu/Zn-containing superoxide dismutase. By joining the thiol groups of proteins, zinc protects them from oxidation by reactive oxygen species. This trace element induces the synthesis of metallothioneins, cysteine-rich proteins acting as free radical scavengers. Zinc suppresses the formation of reactive mixed valence metal oxides and is involved in stabilization of the membrane structure.

The metabolic and structural significance of zinc is determined by a broad spectrum of its biological activity. Thus zinc is necessary for the normal running of processes associated with cell division and differentiation (growth, tissue regeneration, spermatogenesis, and others), and is actively involved in metabolism of nucleic acids and protein synthesis. This trace element is important for metabolism of polyunsaturated fatty acids and reactions of prostaglandin transformations. It shows pronounced lipotropic activity and has hepatoprotective properties. Haase H., Rink L. Zinc Signaling. Zinc in Human Health//Amsterdam, Netherlands: IOS Press. 2011. 243.

In addition, zinc plays an extremely important role in immunological reactions as it is a regulator of the activity of phagocytes and lymphocytes and has an effect on chemotaxis of neutrophils. 5-nucleotidase, a zinc-containing enzyme, is of great importance in the functional state of T- and B-lymphocytes. Isolated zinc deficiency causes severe disturbances in various parameters of T-cell function, including thymus involution, inhibition of cell-mediated cytotoxicity and reduction in the total number of lymphocytes. Zinc is involved in metabolism and stimulation of the activity of pituitary hormones, adrenal glands, pancreas, prostate glands and testes. Zinc plays a clear role in the synthesis, storage and secretion of insulin. Haase H., Rink L. Zinc Signaling. Zinc in Human Health//Amsterdam, Netherlands: IOS Press. 2011. 243.

Zinc also acts as a synergist/antagonist to absorption of many trace elements and vitamins (iron, copper, magnesium, vitamins A, E, folic acid, and others) and has an effect on their metabolism.

In sum, zinc is involved in a variety of vital processes and functions in the human body. A detailed study of some of these functions is not yet fully completed, and many of the mechanisms of action of this trace element are still not fully understood or recognized. However, experimental and clinical studies presented in the literature show zinc as one of the key elements, the decrease in the levels of which in the body is associated with the onset and progression of a number of the most widespread non-epidemic diseases. Since the main metabolic processes in the body occur with the active participation of zinc-containing and zinc-dependent enzymes, its deficiency causes a violation of many vital processes.

The use of classical pharmacological forms of zinc—zinc salts and its chelates—does not always make it possible to achieve a proper effect of compensating for zinc deficiency due to the low bioavailability of this element.

Treatments Methods and Compositions

In one aspect, this disclosure provides a composition comprising $^{64}$Zn-enriched zinc at a therapeutically effective dose for treating type I diabetes. In some embodiments, $^{64}$Zn-enriched zinc is in the form of a $^{64}$Zn$_e$ compound or a $^{64}$Zn$_e$ salt. In some embodiments, the disclosed composition comprises $^{64}$Zn$_e$ is in a form of salt selected from the group consisting of aspartate (chemical formula—C$_4$H$_5$O$_4$N)$_2$$^{64}$Zn$_e$) with 2 aspartic acid molecules, sulfate, and citrate.

The term "$^{64}$Zn$_e$" is used herein to refer to $^{64}$Zn-enriched zinc. That is, zinc that is enriched for $^{64}$Zn such that $^{64}$Zn is enriched greater than its usual percentage in zinc in nature.

The disclosed compositions contain zinc that is enriched for $^{64}$Zn$_e$. Zinc in the form of the light isotope $^{64}$Zn$_e$ is absorbed in the body much better than naturally-occurring zinc. In certain embodiments, the disclosed compositions contain zinc that is at least 80% $^{64}$Zn$_e$, at least 90% $^{64}$Zn$_e$, at least 95% $^{64}$Zn$_e$, or at least 99% $^{64}$Zn$_e$, for example, zinc that is 80% 64Zn$_e$, 85% 64Zn$_e$, 90% $^{64}$Zn$_e$, 95% $^{64}$Zn$_e$, 99% $^{64}$Zn$_e$, or 99.9% $^{64}$Zn$_e$.

In another aspect, this disclosure provides a method of treating type I diabetes by administering a therapeutically effective amount of a disclosed composition to a subject in need thereof.

A method is provided of treating type I diabetes comprising administering to a subject in need thereof a therapeutically effective amount of a composition comprising a $^{64}$Zn$_e$ compound or a salt thereof. In some embodiments, the composition further comprises a diluent or an excipient. In some embodiments, the diluent is water. In further embodiments, the water diluent is deuterium-depleted water. In some embodiments, the $^{64}$Zn$_e$ compound or a salt thereof is between 20-100% $^{64}$Zn$_e$. In further embodiments, the $^{64}$Zn$_e$ compound or a salt thereof is at least 80% $^{64}$Zn$_e$. In further embodiments, the $^{64}$Zn$_e$ compound or a salt thereof is at least 95% $^{64}$Zn$_e$. In some embodiments, the composition contains between 0.05 mg and 110 mg of $^{64}$Zn$_e$. In some embodiments, wherein the composition contains between 1 and 10 mg of $^{64}$Zn$_e$. In some embodiments, the $^{64}$Zn$_e$ compound or a salt thereof is at least 90% $^{64}$Zn$_e$ and the composition is an aqueous solution in which $^{64}$Zn$_e$ is present at a concentration of between 0.1 mg/ml and 10 mg/ml. In some embodiments, the $^{64}$Zn$_e$ is in a form of salt selected from the group consisting of aspartate (chemical formula—C$_4$H$_5$O$_4$N)$_2$$^{64}$Zn$_e$) with 2 aspartic acid molecules, sulfate, and citrate. In some embodiments, the composition is administered by injection. In other embodiments, the composition is administered orally. In certain embodiments, the proinflammatory cytokines is one or more of IL-1, IL-6, IL-12, and IFN-γ.

Formulating and Administering Compositions

The disclosed composition may be administered to a subject in need thereof by any suitable mode of administration, any suitable frequency, and at any suitable, effective dosage.

In some embodiments, the total amount of $^{64}$Zn$_e$ administered is the same as the U.S. recommended daily allowance or intake of zinc. In some embodiments, the total amount of $^{64}$Zn$_e$ administered is ½, twice, three times, five times, or ten times the U.S. recommended daily allowance or intake of zinc. In some embodiments, the total amount of $^{64}$Zn$_e$ is between ½ and 10 times the U.S. recommended daily allowance or intake of zinc. A disclosed composition may comprise the prescribed daily amount to be administered once a day or some fraction thereof to be administered a corresponding number of times per day. A disclosed composition may also comprise an amount of $^{64}$Zn$_e$ to be administered once every two days, once every three days, once a week, or at any other suitable frequency.

The disclosed composition may be in any suitable form and may be formulated for any suitable means of delivery. In some embodiments, the disclosed composition is provided in a form suitable for oral administration, such as a tablet, pill, lozenge, capsule, liquid suspension, liquid solution, or any other conventional oral dosage form. The oral dosage forms may provide immediate release, delayed release, sustained release, or enteric release, and, if appropriate, comprise one or more coating. In some embodiments, the disclosed composition is provided in a form suitable for injection, such as subcutaneous, intramuscular, intravenous, intraperitoneal, or any other route of injection. In some embodiments, compositions for injection are provided in sterile and/or non-pyrogenic form and may contain preservatives and/or other suitable excipients, such as sucrose, sodium phosphate dibasic heptahydrate or other suitable buffer, a pH-adjusting agent such as hydrochloric acid or sodium hydroxide, and polysorbate 80 or other suitable detergent.

When provided in solution form, in some embodiments, the disclosed composition is provided in a glass or plastic bottle, vial or ampoule, any of which may be suitable for either single or multiple use. The bottle, vial or ampoule containing the disclosed composition may be provided in kit form together with one or more needles of suitable gauge and/or one or more syringes, all of which preferably are sterile. Thus, in certain embodiments, a kit is provided comprising a liquid solution as described above, which is packaged in a suitable glass or plastic bottle, vial or ampoule and may further comprising one or more needles and/or one or more syringes. The kit may further comprise instruction for use.

In certain embodiments, the dosage of $^{64}Zn_e$ is proportional to various authoritative daily ingestion guidances (e.g. recommended dietary allowance (USRDA), adequate intake (AI), recommended dietary intake (RDI)) of the corresponding element. In some embodiments, the light isotope dosage is between about ½ and about 20 times the guidance amount, more preferably between about 1 and about 10 times the guidance amount, even more preferably between about 1 and about 3 times the guidance amount. Thus, in certain embodiments, a single dose of a disclosed composition for daily administration would be formulated to comprise a quantity within these ranges, such as about ½, about 1, about 3, about 5, about 10, and about 20 times the guidance amount. These amounts generally are for oral intake or topical application. In some embodiments, the intravenous dosage is lower, such as from about 1/10 to about ½ the guidance amount. Doses at the low end of these ranges are appropriate for anyone with a heightened sensitivity to a specific element or class of elements (e.g., those with kidney problems). For zinc, the daily guidance amount ranges from 2 mg in infants to 8-11 mg (depending on sex) for ages 9 and up. Daily dosages discussed throughout this application may be subdivided into fractional dosages and the fractional dosages administered the appropriate number of times per day to provide the total daily dosage amount (e.g. ½ the daily dose administered twice daily, ⅓ the daily dose administered three times daily, etc.). See Table 1.

TABLE 1

| Element/Isotope | guidance amount, daily | |
| --- | --- | --- |
| Zinc/$^{64}Zn_e$ | Birth to 6 months | 2 mg |
| | 7 months-3 years | 3 mg |
| | Children 4-8 years | 5 mg |
| | Children 9-13 years | 8 mg |
| | 14-18 years (boys) | 11 mg |
| | 14-18 years (girls) | 9 mg |
| | Adults (men) | 11 mg |
| | Adults (women) | 8 mg |

The disclosed composition can be produced by methods employed in accordance with general practice in the pharmaceutical industry, such as, for example, the methods illustrated in Remington: The Science and Practice of Pharmacy (Pharmaceutical Press; 21st revised ed. (2011) (hereinafter "Remington").

In some embodiments, the disclosed compositions comprise at least one pharmaceutically acceptable vehicle or excipient. These include, for example, diluents, carriers, excipients, fillers, disintegrants, solubilizing agents, dispersing agents, preservatives, wetting agents, preservatives, stabilizers, buffering agents (e.g. phosphate, citrate, acetate, tartrate), suspending agents, emulsifiers, and penetration enhancing agents such as DMSO, as appropriate. The composition can also comprise suitable auxiliary substances, for example, solubilizing agents, dispersing agents, suspending agents and emulsifiers.

In certain embodiments, the composition further comprises suitable diluents, glidants, lubricants, acidulants, stabilizers, fillers, binders, plasticizers or release aids and other pharmaceutically acceptable excipients.

A complete description of pharmaceutically acceptable excipients can be found, for example, in *Remington's Pharmaceutical Sciences* (Mack Pub., Co., N.J. 1991) or other standard pharmaceutical science texts, such as the *Handbook of Pharmaceutical Excipients* (Shesky et al. eds., 8th ed. 2017).

In some embodiments, the disclosed composition can be administered intragastrically, orally, intravenously, intraperitoneally or intramuscularly, but other routes of administration are also possible.

Water may be used as a carrier and diluent in the composition. The use of other pharmaceutically acceptable solvents and diluents in addition to or instead of water is also acceptable. In certain embodiments, deuterium-depleted water is used as a diluent.

Large macromolecules that are slowly metabolized, such as proteins, polysaccharides, polylactic acids, polyglycolic acids, polymeric amino acids, copolymers of amino acids, can also be used as carrier compounds for the composition. Pharmaceutically acceptable carriers in therapeutic compositions may additionally contain liquids, such as water, saline, glycerol or ethanol. Moreover, the said compositions may further comprise excipients, such as wetting agents or emulsifiers, buffering substances, and the like. Such excipients include, among others, diluents and carriers conventional in the art, and/or substances that promote penetration of the active compound into the cell, for example, DMSO, as well as preservatives and stabilizers.

The disclosed composition may be presented in various dosage forms depending on the object of application; in particular, it may be formulated as a solution for injections.

The disclosed composition may be administered systemically. Suitable routes of administration includes, for example, oral or parenteral administration, such as intravenous, intraperitoneal, intragastric as well as via drinking water. However, depending on a dosage form, the disclosed composition may be administered by other routes.

In certain embodiments, the disclosed composition comprising $^{64}Zn_e$ is administered intragastrically at a concentration of 2.25 mg/ml for treating type I diabetes in an animal subject. In further embodiments, the disclosed composition is about 2 ml. In further embodiments, the level of enrichment of $^{64}Zn_e$ is about 99% or more. In other further embodiments, the $^{64}Zn_e$ of the 2 ml composition comprises or consists of zinc aspartate (chemical formula—$C_4H_5O_4N)_2{}^{64}Zn_e$) with 2 aspartic acid molecules. The dose of the disclosed composition may vary depending on the subject being treated, severity of the disease, the patient's condition and other factors that will be taken into account by a person skilled in the art when determining the dosage and route of administration for a particular patient based on his/her knowledge in the art.

Light isotopes may be purchased. Zn-64 oxide with the necessary degree of enrichment may be purchased from, for example, Oak Ridge National laboratory, Oak Ridge, Tenn., USA.

Zinc aspartate has a chemical formula—$C_4H_5O_4N)_2{}^{64}Zn_e$, with 2 aspartic acid molecules. The structure of aspartate is:

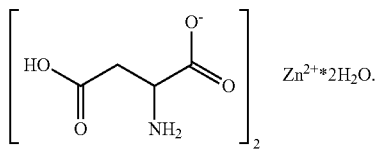

In certain embodiments, the disclosed composition comprises $^{64}Zn_e$ at about 20% to about 100% of the composition.

The disclosed composition comprising $^{64}Zn_e$ is metabolized in the body much better than compositions comprising natural zinc in a form of salts or chelates (which are not enriched for $^{64}Zn$) that are conventionally used in the art. In addition, the said composition helps reduce the toxic effects inherent in traditional medicines with a comparable level of efficacy in treating type I diabetes.

The disclosed composition can be co-administered with another agent or therapy.

EXAMPLES

For this invention to be better understood, the following examples are set forth. These examples are for purposes of illustration only and are not be construed as limiting the scope of the invention in any manner.

Example 1. Comparison Between $^{64}Zn_e$ and Naturally Occurring Zinc

Figure 1:
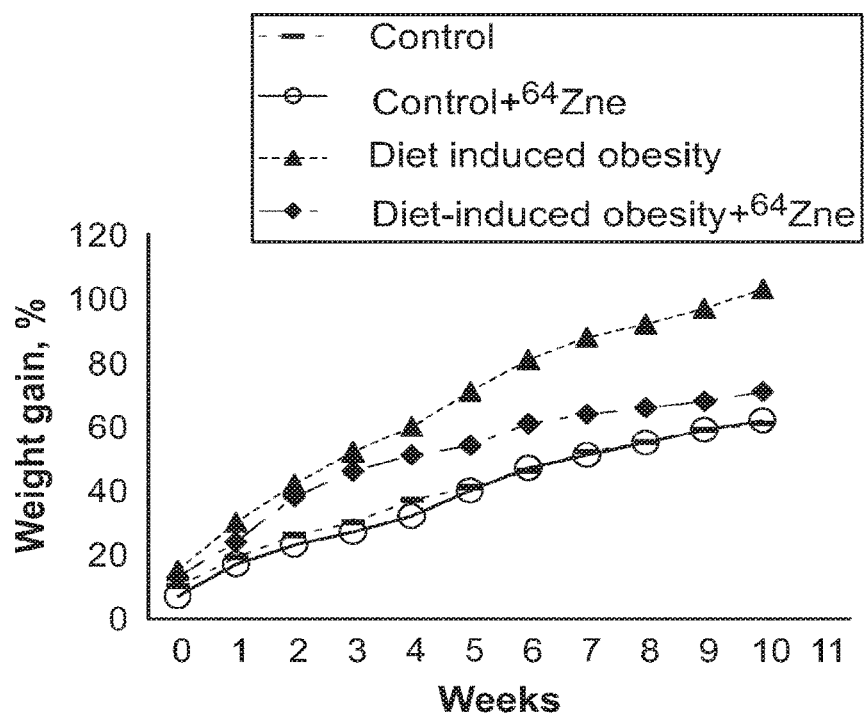
FIG. 1 shows the dynamics of body weight gain for animals in experimental groups (M±n, n=10).

A comparative study of the potential effects of $^{64}Zn_e$ and Zn acetate—$Zn(CH_3COO)_2$ on the absorption and utilization of glucose by the body showed that the zinc isotope had a better effect on the glucose absorption and utilization by the body on a number of parameters:

Positive dynamics of weight gain in control animals (vs the group of animals that were injected with Zn acetate ($Zn(CH_3COO)_2$) was recorded (FIG. 1).

On the seventh day after discontinuation of $^{64}Zn_e$ insulin levels in the blood of animals increased (vs the group of animals that were injected with Zn acetate ($Zn(CH_3COO)_2$) (FIG. 3).

A significant increase was observed in the area of pancreatic islets in experimental animals (microscopical examination on the $7^{th}$ day after the last administration of the substances) (vs the group of animals that were injected with Zn acetate ($Zn(CH_3COO)_2$) (FIG. 4). This is positive dynamics, as with the development of type I diabetes there is a significant lack of insulin due to problems with its synthesis by these islets. The obtained results correlate with the results on determining insulin levels in the bloodstream (FIG. 3).

The glucose tolerance test showed a decrease in glucose levels in the animals after administration of the zinc isotope compared with the control group and the group of animals injected with Zn acetate ($Zn(CH_3COO)_2$) whose glucose levels also dropped, though not so strongly. This may indicate that the zinc isotope has an effect on the insulin levels in blood, which in turn leads to the launch of mechanisms associated with the utilization of glucose from the bloodstream. Considering that insulin is a zinc-dependent protein, it can be assumed that the administration of zinc leads to an increase in either the activity of this protein in relation to its receptor in tissues, or to an increase in the amount of this hormone in the bloodstream.

TABLE 2

Glucose tolerance test
(fast overnight, glucose at the dose of 3
g/kg body weight in a volume of 2 ml)

| | Animal weight, g | 0 min (1 h after effector administration) | 60 min (1 h after glucose administration) |
|---|---|---|---|
| Control (2 ml saline) | | | |
| 1 | 190 | 4.7 | 7.9 |
| 2 | 196 | 5.8 | 8 |
| 3 | 217 | 5.1 | 8 |
| 4 | 206 | 5.4 | 8.2 |
| 5 | 190 | 4.8 | 7.6 |
| $^{64}Zn_e$ (dose: 5 mg/kg in a volume of 2 ml) | | | |
| 1 | 195 | 4.5 | 6 |
| 2 | 178 | 4.8 | 6.3 |
| 3 | 187 | 4.5 | 6.5 |
| 4 | 186 | 4.7 | 6.6 |
| 5 | 184 | 4.8 | 6.5 |
| Zn acetate (dose: 5 mg/kg in a volume of 2 ml) | | | |
| 1 | 193 | 4.6 | 7.2 |
| 2 | 186 | 5.2 | 6.9 |
| 3 | 192 | 5.2 | 7.3 |
| 4 | 188 | 4.9 | 7.2 |
| 5 | 195 | 5.1 | 6.8 |

Results obtained on type I diabetes model show that this substance has a more positive effect on the course of development of type I diabetes (vs. Zn acetate ($Zn(CH_3COO)_2$)) and can potentially be used to reduce toxic effects of increased glucose levels in the bloodstream during the development of this pathology.

Analysis of the accumulation of metals in the kidney and liver tissues (zinc, manganese and copper) showed that only zinc significantly increased in both groups of animals that were injected with zinc (Zn acetate ($Zn(CH_3COO)_2$) or $^{64}Zn_e$) both on day 1 and on day 7 after discontinuation of the substances. This indicates that zinc injected to animals accumulated and its utilization by the body did not increase. All other analyzed metals were within the same concentrations as in the control group of animals. The data obtained indicate the absence of any negative effects of the $^{64}Zn_e$ on the accumulation and utilization of zinc and associated metals by the body.

All these data suggest a more pronounced and higher quality effect of the $^{64}Zn_e$ on absorption and utilization of glucose by the body in comparison with Zn acetate ($Zn(CH_3COO)_2$).

In this Example, Zinc acetate (natural zinc) was administered to an experimental group of animals, at a dose of 3750 mcg of zinc (by metal) per 1 kg of body weight of the animal (rat). Zinc-64 in the form of zinc aspartate was also administered to the experimental group of animals, at a dose of 3750 mcg of zinc (by metal) per 1 kg of body weight of the animal (rat). The administration of these compositions was by intraperitoneal route.

Example 2: Anthropometric Effects of $^{64}Zn_e$-Based Composition in Animal Models of Obesity To assess the effects of the $^{64}Zn_e$-based composition on the development of obesity induced by high-fat diet, some anthropometric values in untreated animal models of obesity and animal models of obesity treated with $^{64}Zn_e$ solution were evaluated.

White non-pedigree rats with an initial weight of 195-205±10 g were used in the experiment. The animals were maintained in an accredited vivarium of the Academic and Research Center "Institute of Biology and Medicine" of Taras Shevchenko National University of Kyiv in accordance with the Standard rules on the arrangement, equipment and maintenance of experimental biological clinics (vivariums). The study was carried out in compliance with international standards and recommendations of the European Convention for the Protection of Vertebrate Animals used for Experimental and other Scientific Purposes (Strasbourg, 18 Mar. 1986) and approved by the Bioethics Commission of the Academic and Research Center "Institute of Biology and Medicine".

Statistical processing of the results was carried out using the methods of variation statistics and correlation analysis using OrginLab Orgin® Pro 9.1 and StatSoft STaStica® 10 software (Brandt, Z. Statistical methods for analysis of observations. M.: Mir, 1975.-312p.). The hypothesis of normal distribution of samples was tested using the Shapiro-Wilk test. If a sample met the criteria of normal distribution, significance of differences between samples was determined using the Student's t-test. If a sample did not meet the criteria of normal distribution, significance of differences between samples was determined using the Mann-Whitney U test. Differences were considered statistically significant when $p<0.05$.

Before the start of the experiment, animals were maintained on a standard diet of the vivarium. To induce obesity in experimental animals, they were fed high-fat diet which consisted of standard feed (60%), lard (10%), chicken eggs (10%), sucrose (9%), peanuts (5%), dry milk (5%) and sunflower oil (1%) (1%) (see X. H. Shen et al., Exp. Biol. and Med. 235: 47-51 (2010)). The feed was prepared by the present inventors. The first 4 weeks of the experiment, all animals were maintained on a high-fat diet after which they were randomly divided into two experimental groups:

animals in the first group (obesity) continued eating their high-fat diet and had free access to water for the next 6 weeks of the experiment;

animals in the second group (obesity+$^{64}Zn_e$ solution) also followed their high-fat diet and had free access to water for the next 6 weeks of the experiment but every third day and until the end of the experiment they were administered a solution of $^{64}Zn_e$ intragastrically at a concentration of 2.25 mg/ml in a volume of 2 ml. This solution contained 2.25 mg/ml of a pharmaceutically acceptable zinc salt, particularly zinc aspartate, wherein the level of enrichment by $^{64}Zn$ was not less than 80 percent. For the preparation of composition claimed standard Dulbecco's phosphate-buffered saline from (specified a manufacturer) (based on deuterium-depleted water Langway) as a diluent (liquid vehicle) was used.

There was also a group of animals (control) that received standard diet prepared by the vivarium and had free access to water during the entire experiment.

Animals in all groups were weighed once a week after an overnight fast. The amount of feed to be consumed by the animals was determined daily. At the end of a 10-week period of the development of obesity models, 24 hours after the last administration of the zinc isotope solution, animals were removed from their cages and decapitated.

The body mass index (BMI) (the ratio of body weight (g) to the square of body length ($cm^2$)) was calculated at the end of the experiment. An increase in BMI is a characteristic morphological sign of obesity developing as a result of accumulation and redistribution of adipose tissue in the body. BMI makes it possible to assess the ratio of body weight to height (body length) and thereby indirectly assess whether the weight is insufficient, normal or excessive. In addition, BMI is used as an integral value that characterizes a composition of the body and a degree of fat deposits, because the distribution of adipose tissue in the body determines the risk of metabolic complications associated with obesity, which must be considered when examining patients that develop obesity. BMI is not only a diagnostic criterion for obesity, but also a good measure of a patient's risk for diseases that can occur with overweight and obesity.

The data obtained during the experiment (Table 3) show that on the $10^{th}$ week of the experiment, the mean body mass index of control animals was 0.60 $g/cm^2$ which value is within a reference range for animals of this age group. BMI of animals eating high-fat diet was 1.14 times higher than BMI of animals of the control group (0.71 $g/cm^2$). The body mass index of rats receiving the $^{64}Zn_e$ solution during the experiment was lower than that of untreated animal models of obesity but slightly higher than the control value (0.65 $g/cm^2$), which indicates that the $^{64}Zn_e$ solution has a positive effect on the general metabolic status of animals.

TABLE 3

Some anthropometric values, the amount and calorie content of food (M ± m, n = 10)

| | Experimental groups | | | |
|---|---|---|---|---|
| | C | C + zinc | DIO | DIO + zinc |
| BMI (g/cm$^2$) | 0.60 | 0.59 | 0.71 | 0.65 |
| Weight gain as of the end of the experiment (%) | 59 | 59 | 103 | 62 |
| Amount of food consumed (g/day) | 34 | 32 | 35 | 29 |
| Calorie content of food (kJ/day) | 525 | 490 | 1001 | 823 |

Note:
C—control;
C + zinc—control on the background of $^{64}Zn_e$ administration;
DIO—diet-induced obesity;
DIO + zinc—diet-induced obesity on the background of $^{64}Zn_e$ administration.

Since BMI is calculated based on weight, a decrease in BMI value may be directly related to the lower weight of animals that received the $^{64}Zn_e$ solution. Therefore, it was further investigated whether administration of the $^{64}Zn_e$ solution had an effect on the weight and weight gain of animal models of obesity. The data obtained (FIG. 1) show that the dynamics of weight gain by animals of the experimental groups differed significantly. Thus, animals that were maintained on a high-fat diet and received the $^{64}Zn_e$ solution gained less weight than animals that were only fed a high-fat diet. Particularly noticeable difference in the weight gain of animals of both groups was observed starting from the 4th week of the experiment. An increase in the body weight of animals eating a high-fat diet reached 103% by the end of the experiment, while animals that received intragastric injections of the $^{64}Zn_e$ solution gained not much more weight than animals in the control group (62% vs. 59%).

It is known that the development of obesity, due to disruption of the coordinated work of a number of neurotransmitter and hormonal systems in the body, leads to disturbances at the level of appetite control and regulation of a feeling of satiety. These disturbances promote excessive food intake and are often accompanied by the development of hyperphagia, a state of an abnormally great desire for food energy the equivalent of which exceeds the energy needs of the body (L. Zhou et al., Cell Metabolism 6: 398 (2007)).

To define possible mechanisms of decrease in the body weight gain of animals treated with the $^{64}Zn_e$ solution, the amount of food consumed by the animals was analyzed. The data obtained are presented in Table 3.

When the data calculated for all experimental groups were compared, there are no particular differences in the amount of food the animals ate on average per day. Thus, animals of the control group and the group of obesity models consumed about 35 g of food per day. However, it should be noted that animals in the control group were maintained on a standard diet while animals in the group of diet-induced obesity models consumed specially prepared high-fat diet the calorie content of which was significantly higher.

Analysis of the results obtained, with due consideration of the calorie content of the food consumed by animals, shows a significant difference in values. Despite the same amount of food eaten by animals, the calorie content of food consumed by the group of diet-induced obesity models that were administrated the composition claimed, was lower than the calorie content for the control group of animals with diet-induced obesity (without administration of the disclosed composition). Furthermore, on week 10, the caloric content for the group of diet-induced obesity models that were administrated the disclosed composition, was almost the same as for the control group which consumed standard food, and for the group, which consumed standard food with simultaneous administration of the disclosed composition.

Figure 2:
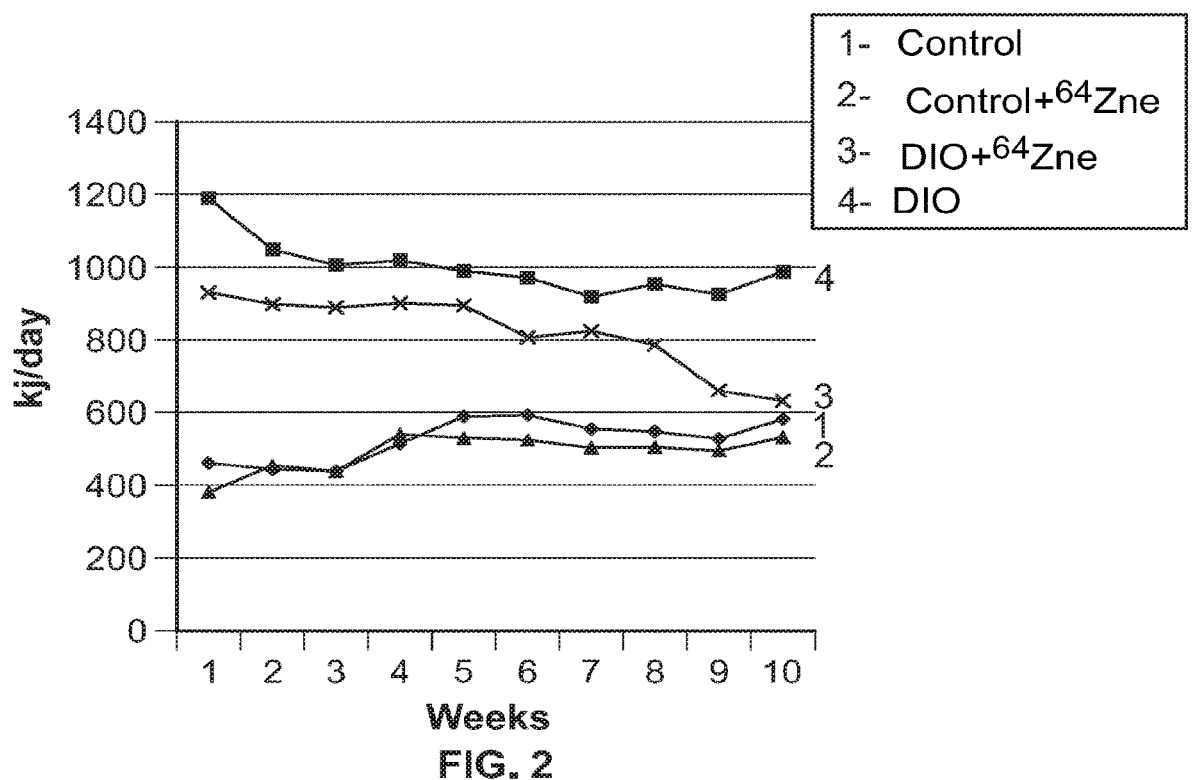
FIG. 2 shows the calorie content of food consumed by animals of the experimental groups (M±n, n=10).

The dynamics of calorie content of food consumed by animals during 10 weeks of the experiment is shown in FIG. 2.

The data obtained suggest that the $^{64}Zn_e$-based composition has an effect on the feeling of satiety because, having free access to food, animals treated with the disclosed composition of a disclosed method consumed significantly less food compared with untreated animals that were only maintained on a high-fat diet. In other words, the animals that received the $^{64}Zn_e$ solution ate less and gained less weight than the animals that did not receive the $^{64}Zn_e$ solution. This difference can be explained by both direct and indirect effects of zinc on energy homeostasis.

Thus it was demonstrated that administration of the $^{64}Zn_e$-based composition caused a decrease in the amount of food consumed per day, which, accordingly, was accompanied by a less pronounced weight gain in animals and normalization of their body mass index in comparison with similar values in untreated animal models of obesity.

Example 3: Biochemical Effects of $^{64}Zn_e$-Based Composition in Animal Models of Obesity An experiment to study the effects of light zinc isotope $^{64}Zn_e$ on blood biochemical variables which undergo pathological changes in obesity, particularly the lipid profile, was carried out. To this end, high-fat diet obesity was induced in experimental animals as described in Example 2. For the experiment, the following animals were used: control animals that consumed standard diet; animals that received high-fat diet for the next 6 weeks; and animals that were fed high-fat diet but were also administered the $^{64}Zn_e$-based composition (zinc aspartate with $^{64}Zn_e$ with an enrichment of 80% or more at a concentration of 2.25 mg/ml was administered intragastrally in a volume of 2 ml) during all 6 weeks of the experiment. The results of the experiment are shown in Table 4.

TABLE 4

Serum biochemical variables in animals from experimental groups (M ± m, n = 10)

| Variables | Group | | |
|---|---|---|---|
| | C | DIO | DIO + $^{64}Zn_e$ |
| Alkaline phosphatase activity, RU | 74.3 ± 12.1 | 37.2 ± 15.4* | 87.6 ± 18.7# |
| Triglycerides, g/L | 2.55 ± 0.20 | 4.39 ± 0.73* | 2.79 ± 0.30# |
| Cholesterol, mmol/L | 2.42 ± 0.19 | 5.76 ± 0.87* | 2.83 ± 0.23# |
| Free fatty acids, mg/L | 23.60 ± 4.67 | 74.50 ± 9.23* | 31.62 ± 7.92# |

*the difference is significant compared to the control group of animals;
the difference is significant compared to the group of animal models of obesity
Note:
C—control;;
DIO—diet induced obesity;
DIO—$^{64}Zn_e$: diet induced obesity on the background of $^{64}Zn_e$ administration.

It was found that the $^{64}Zn_e$-based composition had a positive effect on lipid metabolism in the body. A decrease in the levels of triglycerides, cholesterol and free fatty acids in the serum of animals that were fed a high-fat diet and treated with $^{64}Zn_e$ was almost at the same level as in the control group of animals.

Example 4: Effects of $^{64}Zn_e$ on the Redox State in Experimental Animals A number of studies have shown that obesity is closely associated with an altered redox state and an increased metabolic risk. It is oxidative stress that is one of the factors causing adipocyte dysfunction. Oxidative stress and the resulting tissue damage and cell death are the basis for the development of many chronic pathological conditions. Excessive production of free radicals and/or depletion of their detoxification system lead to the prooxidant-antioxidant imbalance, which in turn affects the structures of cellular membrane lipids and proteins and nucleic acids. Lipid peroxidation (LPO) mediated by free radicals is one of the important causes of the destruction of cellular membranes and further cell damage. Degradation of membrane lipids induces an increase in the membrane's fluidity and its permeability to ions, which disrupts cellular homeostasis as a whole. Products of free radical oxidation (4-hydroxyalkenes, malonic dialdehyde, etc.) are highly mutagenic and cytotoxic.

In addition, oxidative stress activates preadipocyte differentiation and stimulates hypertrophy of mature adipose cells. Excessive production of ROS in the accumulated adipose tissue further leads to the induction of oxidative stress in the bloodstream, which contributes to the spread of oxidative stress to organs distant from the fat depot.

The prooxidant-antioxidant balance in animals was assessed using the obesity models as described in Example 2. The control group, the group of untreated animal models of obesity and the group of animals that were fed a high-fat diet and treated with $^{64}Zn_e$ were used in the experiment.

Concentrations of lipid peroxidation products serve as an informative criterion making it possible to draw a conclusion about intensity of oxidative processes. There are primary lipid peroxidation products (such as conjugated dienes) and secondary lipid peroxidation products (such as aldehydes, malonic aldehyde in particular), which are formed as a result of breakdown of carbon-carbon double bonds in the carbon skeletons of oxidized molecules. Subsequently, the LPO initiation leads to the formation of conjugated Schiff bases of phospholipids and malonaldehyde-like products, which cause disturbances in the ordered orientation of phospholipid molecules and affect lipoprotein intermolecular interactions and configuration of the basement membrane.

Considering the above, concentrations of primary LPO products (conjugated dienes (CD)), secondary LPO products (TBA-reactive substances (TBARSs)) and end LPO products (Schiff bases (SB)) in animals treated with $^{64}Zn_e$ were determined. Taking into account that obesity is accompanied by the development of systemic oxidative stress which covers most tissues to various extents and leads to the disruption of integrity of cellular membranes and admission of lipid peroxidation products to the bloodstream, values characterizing the state of the prooxidant-antioxidant system were determined in the blood serum of animals.

It was found that the obesity models had elevated serum levels of primary products of free radical lipid oxidation (1.86 times as high as in the control) (Table 5). Such result can be explained from the standpoint of disturbed lipid metabolism, impairment of the processes of transportation of fatty acids in particular, and, accordingly, an increase in the plasma levels of free and esterified fatty acids, which are direct substrates for the action of reactive oxygen species.

On the other hand, accumulation of lipid peroxidation products in serum may be a direct result of violation of the integrity of cellular membranes due to oxidative destruction of their lipid component and admission of lipid peroxidation products to the bloodstream.

TABLE 5

Serum levels of lipid peroxidation products in animals from experimental groups (M ± m, n= 10)

| Experimental groups | Conjugated dienes, nmol/mg protein | TBA-reactive substances, nmol/mg protein | | Schiff bases, RU/mg protein |
|---|---|---|---|---|
| | | Spontaneous accumulation | $Fe^{2+}$-ascorbate-induced accumulation | |
| C | 0.021 ± 0.001 | 0.006 ± 0.0003 | 0.033 ± 0.005 | 41.31 ± 2.47 |
| DIO | 0.039 ± 0.002 * | 0.029 ± 0.002 * | 0.61 ± 0.003 * | 168.86 ± 8.15 * |
| DIO + $^{64}Zn_e$ | 0.025 ± 0.008 | 0.005 ± 0.0003 # | 0.15 ± 0.008 *,# | 56.27 ± 4.33 *,# |

* the difference is significant compared to the control group of animals;
the difference is significant compared to the group of animal models of obesity
Note:
C—control;
DIO—diet induced obesity;
DIO + $^{64}Zn_e$—diet induced obesity on the background of $^{64}Zn_e$ administration.

Thus, elevated levels of lipid peroxidation products on the $10^{th}$ week of obesity development clearly indicate that oxidative stress has a systemic nature and that this process is chronic, which is an unfavorable prognostic marker as these metabolites are extremely toxic compounds and their negative impact is exhibited at different levels and leads to DNA molecule damage, destruction of protein molecules and glycosaminoglycans, changes in the lipid composition of cellular membranes and disruption of membrane-associated processes.

Administration of $^{64}Zn_e$-based composition to animals helped normalize the levels of primary, secondary and end LPO products, which serves as additional evidence of the ability of $^{64}Zn_e$ to influence an overall prooxidant-antioxidant status of the body.

According to modern concepts, reactive oxygen species not only activate lipid peroxidation processes but also cause oxidative destruction of protein molecules, causing disruption of conformation of both soluble and membrane-bound enzymes, receptors and ion channels, which ultimately leads to the loss of their biological activity (enzymatic, receptor, transport, for example). Protein oxidation results in the formation of aldehyde and ketone groups of amino acid residues (carbonyl groups) in proteins.

Thus, an increase in the number of oxidatively modified proteins may be considered as an early criterion of free radical tissue damage and a marker of the depletion of antioxidant defense system in the body. This study revealed increased serum levels of oxidatively modified proteins in animal models of obesity (Table 6).

TABLE 6

Serum levels of products of oxidative modification of proteins in animals from experimental groups (M ± m, n = 10)

| Groups | Aldehyde-dinitrophenyl-hydrazones, nmol/mg protein | Ketone-dinitrophenyl-hydrazones, nmol/mg protein |
|---|---|---|
| C | 0.187 ± 0.009 | 0.255 ± 0.023 |
| DIO | 0.698 ± 0.041 * | 0.571 ± 0.035 * |
| DIO + $^{64}Zn_e$ | 0.253 ± 0.012 *,# | 0.200 ± 0.024 *,# |

* the difference is significant compared to the control group of animals;
the difference is significant compared to the group of animal models of obesity
Note:
C—control;
DIO—diet-induced obesity;
DIO + $^{64}Zn_e$—diet-induced obesity on the background of $^{64}Zn_e$ administration.

The experimental data showed that in animals that were fed a high-fat diet during the entire experiment and received injections of the $^{64}Zn_e$ solutions, the levels of aldehyde-dinitrophenyl-hydrazones exceeded the benchmark but were lower compared to the values in untreated animals having obesity. As for ketone-dinitrophenyl-hydrazones, their concentration remained within the control value. Such results correlate with the data showing a decrease in the levels of LPO products and suggest a decrease in the intensity of free radical oxidation reactions.

Example 5: Effects of $^{64}Zn_e$-Based Composition on Cytokine Profile in Animal Models of Obesity The cytokine profile in animals was assessed using the obesity models as described in Example 2. The control group, the group of untreated animal models of obesity and the group of animals that were fed a high-fat diet and treated with $^{64}Zn_e$ were used in the experiment.

Obesity pathogenesis is accompanied by a systemic chronic inflammatory process, the degree of intensity of which can be assessed by the serum levels of pro- and anti-inflammatory cytokines.

Analysis of the serum cytokine profile in animal models of obesity showed an increase in the levels of pro-inflammatory cytokines (Table 7). In animals fed a high-fat diet and administered the $^{64}Zn_e$ solution, there was a decrease in the serum levels of pro-inflammatory cytokines against the background of an increase in the levels of anti-inflammatory cytokines, which were even higher than in the animals from the control group.

TABLE 7

Serum cytokine profile in animals from experimental groups
(M ± m, n = 10)

| Groups | Levels, RU/mg protein Pro-inflammatory cytokines | | | |
|---|---|---|---|---|
| | IL-1 | IL-6 | IL-12 | IFN-γ |
| C | 3.4 ± 0.3 | 4.5 ± 0.3 | 0.5 ± 0.05 | 3.6 ± 0.8 |
| C + $^{64}$Zn$_e$ | 3.5 ± 0.7 | 4.3 ± 0.2 | 0.3 ± 0.04 | 4.6 ± 0.6 |
| DIO | 11.1 ± 2.0 * | 7.9 ± 0.5 * | 3.7 ± 0.07 * | 6.5 ± 0.8 * |
| DIO + $^{64}$Zn$_e$ | 4.2 ± 0.4 # | 5.1 ± 0.4 # | 2.4 ± 0.06 *,# | 4.1 ± 1.2 |

| Groups | Levels, RU/mg protein Anti-inflammatory cytokines | | |
|---|---|---|---|
| | IL-4 | IL-10 | TGF |
| C | 5.1 ± 0.2 | 3.9 ± 0.4 | 3.8 ± 0.8 |
| C + $^{64}$Zn$_e$ | 4.6 ± 0.8 | 4.1 ± 0.5 | 4.1 ± 0.4 |
| DIO | 4.4 ± 0.9 | 4.1 ± 1.5 | 3.5 ± 1.3 |
| DIO + $^{64}$Zn$_e$ | 5.6 ± 1.6 | 6.8 ± 1.1*, # | 5.7 ± 0.3 *, # |

* the difference is significant compared to the control group of animals;
the difference is significant compared to the group of animal models of obesity
Note:
C—control;
C + $^{64}$Zn$_e$—control on the background of $^{64}$Zn$_e$ administration;
DIO—diet-induced obesity; DIO + $^{64}$Zn$_e$: diet-induced obesity on the background of $^{64}$Zn$_e$ administration.

One of the basic mechanisms of the effects of zinc enriched for the isotope $Zn_e$ on the cytokine profile may be its inhibition of transcription factors sensitive to oxidative stress. A certain normalizing effect of the $^{64}Zn_e$-based composition on the cytokine profile in animal models of obesity may serve as evidence of a possible anti-inflammatory potential of the claimed composition in obesity.

Thus, the experimental data confirmed positive effects of the $^{64}Zn_e$ based composition on a number of pathological variables in animal models of obesity. In particular, it was demonstrated that administration of the $^{64}Zn_e$-based composition to experimental animals caused a decrease in the body mass index and a reduction in the body weight gain and the amount of food consumed; $^{64}Zn_e$ was found to have a positive effect on lipid metabolism in the bodies of animals; normalization of prooxidant-antioxidant homeostasis due to a decrease in the intensity of free radical processes was demonstrated; the ability of $^{64}Zn_e$ to influence the serum cytokine profile in animals was revealed. The effects observed in this study support the efficacy of the claimed $^{64}Zn_e$-based composition for the prevention and treatment of obesity.

For Example 2-5, the zinc-64 enriched disclosed composition has a zinc salt/compound with the following structural formula:

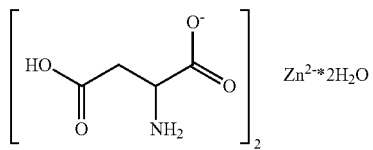

The compound is a crystalline hydrate, which contains 2 water molecules. The molar mass is 364 g/mol. 2.2H$_2$O should be considered as .2H$_2$O, Because the 0.2H$_2$O is unbound water that can evaporate when drying the powder. .2H$_2$O is crystalline hydrate and is a part of the molecule. 4.5 mg of zinc aspartate (which was in a solution volume of 2 ml) was used, which contained 17.8% pure zinc-64 (by metal). Thus, each dose, which was 4.5 mg zinc aspartate, contained 800 ug zinc-64 (by metal).

Example 6: Zn64 Stable Isotope in Aspartate Form on Obesity and Type 2 Pre-Diabetes in Experimental Animals (Rats) Fed High-Fat Diets Over a Specified Time List of Abbreviations
ROS—reactive oxygen species
AOD—antioxidant defense
FFA—free fatty acids
GI tract—gastrointestinal tract
BMI—body mass index
IDO—indoleamine-2,3-dioxygenase
IR—insulin resistance
MAO—monoamine oxidase
OMP—oxidative modification of proteins
OS—oxidative stress
SOD—superoxide dismutase
IL—interleukin This study assesses the effects of Zn-64 stable isotope in aspartate form on the development of obesity induced by high-fat diet in experimental animals. The following tasks were set:

To investigate the effects of Zn-64 stable isotope in aspartate form on a number of anthropometric (body mass index, weight, weight gain) and biochemical (glucose concentration, insulin level, alkaline phosphatase activity, albumin content) values in animal models of obesity.

To investigate the effects of Zn-64 stable isotope in aspartate form on morphofunctional properties of the pancreas and liver of animals fed a high-fat diet.

To assess the effects of Zn-64 stable isotope in aspartate form on the functions of central and peripheral serotoninergic systems (tryptophan and serotonin levels, tryptophan hydroxylase, tryptophan decarboxylase, monoamine oxidase and indoleamine 2,3-dioxygenase activity) in animal models of obesity.

To assess the effects of Zn-64 stable isotope in aspartate form on free radical processes (levels of primary, secondary and end products of lipid peroxidation, levels of products of oxidative modification of proteins) and the activity of key antioxidant enzymes (superoxide dismutase, catalase) in serum and adipose tissue in animal models of obesity.

To assess the effects of Zn-64 stable isotope in aspartate form on the cytokine profile (levels of pro- and anti-inflammatory cytokines) in serum and adipose tissue, as well as resistin and ghrelin levels in animal models of obesity.

To investigate the effects of Zn-64 stable isotope in aspartate form on the distribution of divalent metals (zinc, copper, manganese, etc.) between different organs in animal models of obesity.

Materials and Methods
Development of Obesity Models

White non-pedigree rats were used in the studies. The animals were maintained in an accredited vivarium of the Academic and Research Center Institute of Biology and Medicine of Taras Shevchenko National University of Kyiv in accordance with the Standard rules on the arrangement, equipment and maintenance of experimental biological clinics (vivariums). The study was carried out in compliance with international standards and recommendations of the European Convention for the Protection of Vertebrate Animals used for Experimental and other Scientific Purposes (Strasbourg, 18 Mar. 1986) and approved by the Bioethics Commission of the Academic and Research Center Institute of Biology and Medicine. Murzin, O. B., European Convention for the Protection of Vertebrate Animals Used for Experimental and Other Scientific Purposes/O. B. Murzin,//Practical workbook on human physiology.-Dnipropetrovsk: Publishing House of Dnipropetrovsk University, 2004.-P. 135-148.

Animals with an initial weight of 195-205±10 g maintained on the standard diet of the vivarium before performing obesity models were used in the experiments. To induce obesity in experimental animals, they were fed high-fat diet which consisted of standard feed (60%), lard (10%), chicken eggs (10%), sucrose (9%), peanuts (5%), dry milk (5%) and sunflower oil (1%), Shen X. et al., Experimental Biology and Medicine.-2010.-No 235.-P. 47-51. The first 4 weeks of the experiment, all animals were maintained on a high-fat diet, after which they were randomly divided into two experimental groups:

- animals in the first group (obesity) continued to eat their high-fat diet and had free access to water for the next 6 weeks of the experiment.
- animals in the second group (obesity+solution of Zn-64 stable isotope in aspartate form) also followed their high-fat diet and had free access to water for the next 6 weeks of the experiment. But every third day and until the end of the experiment they were intragastrically administered a solution of Zn-64 stable isotope in aspartate form. The dose of zinc aspartate administered to each animal was 4.5 mg (substance per animal), which were administered with a gavage in a volume of 2 ml of solution.

There was also a group of animals (control) that received standard diet prepared by the vivarium and had free access to water during the entire experiment.

To check the presence or absence of the effect of Zn-64 stable isotope in aspartate form on the studied anthropometric and biochemical parameters, a group of animals was formed (control+solution of Zn-64 stable isotope in aspartate form) which ate standard vivarium diet and had free access to water over the entire period of the experiment but every third day and until the end of the experiment the animals were intragastrically administered Zn-64 stable isotope in aspartate form. The dose of zinc aspartate administered to each animal was 4.5 mg (substance per animal), which were administered with a gavage in a volume of 2 ml of solution.

Animals in all groups were weighed once a week after an overnight fast. The amount of feed to be consumed by the animals was determined daily. At the end of a 10-week period of the development of obesity models, 24 hours after the last administration of Zn-64 stable isotope in aspartate form, animals were removed from their cages and decapitated.

The body mass index (BMI) (the ratio of body weight (g) to the square of body length ($cm_2$)) was calculated at the end of the experiment.

Preparation of Blood Serum

Animal serum was prepared from whole blood. To remove fibrinogen-related proteins, the blood was incubated at 37° C. for 30 minutes, after which a blood clot was carefully separated from the walls of the tube with a clean, dry glass rod to accelerate the production of serum. Samples were centrifuged for 15 min at 2500 g. The resulting supernatant (serum) was immediately separated from blood cells and frozen and stored at −20° C. until the experiments.

Preparation of Adipose Tissue Homogenate

At the end of the experiment, the animals were euthanized by decapitation. All manipulations during the tissue removal were carried out at a temperature of 1-4° C.

Adipose tissue was crushed using cold scissors then transferred to a homogenizer with a loose-fitting Teflon pestle. The tissue was homogenized using approximately 30 strokes of the pestle in cold homogenization buffer (50 mM Tris-HCl (pH 7.4) containing 130 mM NaCl). Primary homogenate thus obtained was centrifuged at 600 g for 15 minutes. The supernatant was carefully collected and re-centrifuged at 15,000 g for 15 minutes. The supernatant was then frozen and stored at −80° C. until the experiments.

Preparation of Brain Tissue Homogenate

At the end of the experiment, the animals were euthanized by decapitation. All manipulations during the organ removal were carried out at a temperature of 1-4° C.

The animal's head was separated from the body and the skull was carefully cut. The brain was carefully lifted with a scalpel from the bony vault, all cranial nerves were amputated and the brain was removed from the skull. The brain was divided into two parts with a longitudinal incision made between the hemispheres.

Brain tissue was crushed using cold scissors then transferred to a homogenizer with a loose-fitting Teflon pestle. The tissue was homogenized using approximately 30 strokes of the pestle in cold homogenization buffer (50 mM Tris-acetate, pH 7.4, containing 5 mM EDTA and 10% sucrose). The tissue: buffer ratio was 1:10. The homogenate thus obtained was centrifuged at 1500 g for 20 minutes. The supernatant was then carefully collected and frozen and stored at −80° C. until the experiments.

Preparation of Duodenal Tissue Homogenate

At the end of the experiment, the animals were euthanized by decapitation. All manipulations during the organ removal were carried out at a temperature of 1-4° C.

After opening the abdomen, the duodenum was removed from the body of the animal and washed in a Petri dish in 0.9% sodium chloride solution. The duodenal mucosa was isolated mechanically using a scalpel and then homogenized in 10 mM Tris-HCl buffer, pH 7.4, containing 1 mM EDTA and 0.25 M sucrose. The tissue: buffer ratio was 1:10. The homogenate thus obtained was centrifuged at 1500 g for 10 minutes. The supernatant was then carefully collected and frozen and stored at −80° C. until the experiments.

Determination of Glucose Concentration in Serum

The glucose concentration was measured in the blood of animals that had fasted for at least 2 hours. Blood was collected from the tail vein using a catheter. The glucose concentration was determined using a GLUTOFOT-II glucose meter (Ukraine) according to the manufacturer's instructions. Medical test "Glyukofot-II": [user's manual for "Glyukofot-II—Hemoglan].—Kiev: Norma, 2008.-12 p. The test strip contained all the necessary reagent components to determine the glucose concentration by glucose oxidase method, including absorption of glucose oxidase and peroxidase enzymes into a porous hydrophilic membrane. Formation of a colored complex was the result of the reaction. A drop of whole blood was applied to the strip and left at room temperature for 30 seconds. The strip was then washed with distilled water and placed in a blood glucose meter. The glucose concentration was expressed in mmol/L.

Determination of the Levels of Insulin, Interleukins and Adipokines in Serum and Adipose Tissue Homogenate The levels of insulin, interleukins and adipokines were determined using immunoenzyme method (Halenova T I et al. RSC Adv. 2016; 6: 100046-55), which was carried out in microplates with a sorption capacity in accordance with the soluble protein test procedure. The antigen solution, previously diluted with 0.1 M $NaHCO_3$ buffer, pH 9.6, to a concentration of 10 µg/ml, was incubated in the plate wells for 12 hours at 4° C. Unbound material was removed by washing the wells three times with TBS buffer, first with 0.05% Tween-20, then without Tween-20. Non-specific binding sites were blocked by adding a solution of 5% skim milk or a solution of 1% bovine serum albumin to the plate wells and incubating them for 60 minutes at 37° C. After incubation, the wells were washed three times with TBS, first with 0.05% Tween-20, then without Tween-20. Primary antibodies were diluted in TBS in accordance with the manufacturer's instructions and incubated with the antigen for 60 min at 37° C. After washing with TBS working buffer, first with the addition of 0.05% Tween-20, then without Tween-20, the conjugate of secondary antibodies was added to the wells and incubated for 60 min at 37° C. As with the primary antibodies, secondary antibodies were diluted in TBS in accordance with the manufacturer's instructions. After the washing procedure, phenyldiamine dihydrochloride as substrate in 0.05M phosphate-citrate buffer was added to each well, followed by the addition of 0.3% hydrogen peroxide. After 10 minutes, the reaction time needed for development, 2.5 n $H_2SO_4$ was added.

The absorbance at a wavelength of 492 nm was measured using a µQuant microplate spectrophotometer (BioTek Instruments).

Determination of Serum Alkaline Phosphatase Activity

Serum alkaline phosphatase activity in the animals was measured spectrophotometrically using a Microlab 300 biochemical analyzer and standard PLIVA-Lachema Diagnostika test kits (Czech Republic). Test kit//Pliva-Lachema Diagnostika.-2008.

As a result of hydrolytic cleavage of p-nitrophenyl phosphate catalyzed by alkaline phosphatase, p-nitrophenol is formed, which gives an intense yellow color in alkaline medium. The optical density of samples was measured at a wavelength of 405 nm. The alkaline phosphatase activity was expressed in relative units.

Determination of Serum Albumin

The levels of serum albumin in the animals were determined spectrophotometrically using a Microlab 300 biochemistry analyzer and standard PLIVA-Lachema Diagnostika test kits (Czech Republic). Test kit//Pliva-Lachema Diagnostika.-2008.

Determination of Serum Superoxide Dismutase Activity

To measure superoxide dismutase activity, a method based on the ability of this enzyme to inhibit auto-oxidation of adrenaline was used. Syrota T. V. Questions of med. clin.—1999.-V. 5, No. 3.-P. 263-272.

Serum aliquots were added to microplate wells containing 0.2M bicarbonate buffer, pH 10. The reaction was initiated by adding 0.1% adrenaline solution in each well. A relevant volume of buffer was added to the "blank" wells to which no test sample was added. The optical density was measured at a wavelength of 347 nm using a µQuant microplate spectrophotometer (BioTek Instruments) at the $4^{th}$ and $8^{th}$ minute after adrenaline was added to the wells. The enzyme activity was expressed in relative units/min/mg.

Determination of Catalase Activity

To determine catalase activity, a spectrophotometric method was used which depends on the ability of hydrogen peroxide to form a stable colored complex with molybdenum salts. Korolyuk M. A. et al., Lab. Business.-1988.-No. 1.-P. 44-67. During incubation, the concentration of hydrogen peroxide decreased due to the enzymatic activity mediated by catalase in the test sample. 4% ammonium molybdate solution and 0.03% hydrogen peroxide were used. The reaction was started by adding the test sample to 0.03% hydrogen peroxide. Instead of protein, an appropriate volume of distilled water was added to the blank sample. The reaction was stopped after 10 minutes by addition of 4% ammonium molybdate solution to the incubation medium. The optical density was measured at a wavelength of 410 nm using a µQuant microplate spectrophotometer (BioTek Instruments). Catalase activity was calculated using a calibration curve and quoted as µmol $H_2O_2$/mg protein×min.

Determination of the Levels of Diene Conjugates and Schiff Bases in Serum and Adipose Tissue Homogenates An aliquot of the test sample containing 0.1-0.5 mg of protein was placed in a tight-fitting glass homogenizer, to which heptane/isopropyl alcohol mixture was added at a 1:1 ratio, and homogenized for 10 minutes. The samples then were centrifuged at 1000 g for 15 minutes in test tubes closed with a tight-fitting stopper. The supernatant fraction was carefully collected and distilled water was added to separate the phases of heptane and isopropyl alcohol. Levels of Schiff bases were determined in the upper heptane phase by measuring the optical density of samples at an excitation wavelength of 360 nm and an emission wavelength of 420 nm using a spectrophotometer. The levels of Schiff bases represented the number of units per 1 mg of protein.

To determine the levels of diene conjugates, an aliquot of the heptane phase was taken to which 96% ethanol was added and the samples were thoroughly mixed. The optical density of the samples was measured at a wavelength of 233 nm using a spectrophotometer. The levels of diene conjugates were calculated using a molar extinction coefficient $(2.2 \times 10^5$ $cm^{-1} \times M^{-1})$ for conjugated dienes occurring when polyunsaturated higher fatty acids were oxidized and quoted in nmol per mg protein. Nedzvetsky V et al., J Diabetes Metab. 2012; 3(8): 1-9.

Determination of Serum Levels of TBA-Active Products and Adipose Tissue Homogenates An aliquot of the test sample was added to the sample and an equal volume of 17% trichloroacetic acid (TCA) was added. The samples were centrifuged at 1000 g for 15 min. Nedzvetsky V et al., J Diabetes Metab. 2012; 3(8): 1-9. A solution of 0.8% thiobarbituric acid was added to the supernatant and incubated in a boiling water bath for 10 minutes before the color developed. The optical density of the samples was measured at a wavelength of 532 nm using a spectrophotometer. The concentration of TBA-active products was expressed in nmol per 1 mg of protein and was calculated using a molar extinction coefficient $(1.56 \times 10^5$ $cm^{-1} \times M^{-1})$.

Determination of the Levels of Products of Oxidative Modification of Proteins

Estimation of the intensity of oxidative modification of proteins is based on the reaction between protein carbonyls and Schiff bases and 2,4-dinitrophenylhydrazine (DNPH) with the formation of 2,4-dinitrophenylhydrazons of a neutral and basic nature. Vartanyan L. S, Gurevich S. M. Biochemistry.-1989.-Vol. 54, No. 6.-P. 1020-1025.

An aliquot of the test sample (0.2 mg of protein) was added to the test tubes containing 0.15M potassium phosphate buffer, pH 7.4. Proteins were precipitated by adding a 20% TCA solution. After the samples were centrifuged at 1000 g for 15 minutes, a 0.1M solution of 2,4-DNPH in 2 M HCl was added to the precipitate of denatured proteins. After an hour incubation at room temperature, the precipitate was washed three times with ethanol: ethyl acetate (1:1) mixture to remove lipids and 2,4-DNPH, which were not bound to carbonyls. The so washed precipitate was dried and dissolved in 8M urea in a boiling water bath for 10 minutes.

To determine the aldehyde and ketone products of the oxidative modification of proteins, the optical density was measured at a wavelength of 356 nm and 370 nm, respectively. The obtained values were recalculated using an appropriate molar extinction coefficient.

Determination of the Levels of Serotonin and Tryptophan in the Brain and Duodenal Homogenates and Serum Aliquots of serum and tissue homogenates were mixed with 0.4M perchloric acid at the ratio of 1:5 to precipitate proteins. The samples were incubated at 4° C. for 60 minutes and then centrifuged at 800 g for 5 min in a refrigerated centrifuge at 4° C. After the phase separation, the supernatant was collected and pH was adjusted to 5-6 with 2 M KOH. The samples were reprecipitated by centrifugation. The supernatant was applied to a KM-Sepharose column previously equilibrated with 0.01M sodium phosphate buffer, pH 6.2. The bound material was eluted at room temperature using buffer 1 (0.01M sodium phosphate buffer, pH 6.2) and buffer 2 (0.03M sodium phosphate buffer, pH 6.2). Tryptophan was eluted using buffer 1, and serotonin was eluted using buffer 2.

Tryptophan levels were measured with a spectrofluorometer at an excitation wavelength of 295 nm and an absorption wavelength of 550 nm, versus a blank sample which, instead of the test sample, contained a corresponding volume of distilled water.

Serotonin levels were measured with a spectrofluorometer at an excitation wavelength of 359 nm and an absorption wavelength of 485 nm, versus a blank sample which, instead of the test sample, contained a corresponding volume of distilled water. Gaitonde M. K.//Biochem. S.-1974.-Vol. 139.-P. 625-631. Maksymenko E. G., Savchenko V. N.// Visnyk of V. N. Karazin Kharkiv Nat. University. Medicine.-2000.-1, No. 494.-P. 40-43. H. Weissbach et al.,/J Biol Chem//—1957.-Vol. 230, No 2.-P. 865-71.

Determination of Tryptophan Hydroxylase Activity in Brain and Duodenal Homogenates Tryptophan hydroxylase activity was determined as described by Donald M. Kuhn, at al., Biochemistry.-1980.-Vol. 77.-P. 4688-4691. Tissue homogenates were thawed at room temperature and centrifuged at 12000 g for 30 min. The supernatant was used in further studies.

An incubation medium was prepared in Ependorf microcentrifuge tubes that contained 500 mM Tris-HCl, pH 7.4, 20 mM dithiotrietol, 1 mM $CaCl_2$), 4 mM L-tryptophan and 50 μg catalase, to which an aliquot of the supernatant was then added. The samples were incubated in a thermostat at 37° C. for 15 min. The reaction was stopped by precipitating proteins with 6M $HClO_4$. To separate the precipitated proteins, the samples were centrifuged at 600 g for 5 minutes.

The optical density of the samples was measured at 295/540 nm with a spectrofluorometer. A blank sample containing the incubation medium and distilled water was used as a control.

Determination of Indolamine-2,3-Dioxigenase Activity in Brain and Duodenal Homogenates Indolamine-2,3-dioxigenase activity was determined as described by Y. Kudo, C. A. R. Boyd, I. L. Sargent et al.//Mol. Human reproduction.-2000.-Vol. 6, N 4.-P. 369-374. Tissue homogenates were thawed at room temperature and centrifuged at 12000 g for 30 min. The supernatant was used in further studies.

An incubation medium was prepared in Ependorf microcentrifuge tubes that contained 100 mM potassium-phosphate buffer, pH 7.5, 5 mM L-tryptophan, 10 mM ascorbate, 0.2 mM methylene blue, 50 μg catalase, to which an aliquot of the supernatant was then added. The samples were incubated in a thermostat at 37° C. for 30 min. The reaction was stopped by precipitating proteins with 10% trichloroacetic acid. To separate the precipitated proteins, the samples were centrifuged at 600 g for 5 minutes. Then 1M Tris-HCl, pH 7.0 was added to the aliquot of the supernatant.

The optical density of the samples was measured at 360 nm using a spectrofluorometer versus a blank sample that contained the incubation medium and distilled water.

Determination of Serum Monoamine Oxidase Activity

Serum monoamine oxidase activity was determined using a method described by Balakleevsky A. I.//Lab. business.-1976.-3.-P. 151-152. The method consists in the formation of benzaldehyde from benzylamine hydrochloride under the action of MAO. Benzaldehyde interacts with 2,3-dinitrophenylhydrazine and forms insoluble hydrazone which can be precipitated by centrifugation. The hydrazone precipitate, in turn, forms a stable compound of raspberry color in an alkaline medium, the content of which can be determined spectrophotometrically.

An incubation medium was prepared in Ependorf microcentrifuge tubes that contained 0.2M phosphate buffer, pH 7.4, distilled water, and a 1% solution of benzylamine hydrochloride. A blank sample did not contain benzylamine hydrochloride. The reaction was started by addition of an aliquot of serum. The samples were incubated in a thermostat at 37° C. for 3 hours. The reaction was stopped by precipitating proteins with 10% trichloroacetic acid. To separate the precipitated proteins, the samples were centrifuged at 600 g for 5 minutes. A 0.1% solution of 2,3-dinitrophenylhydrazine prepared in 2M HCl was added to the resulting supernatant. The samples were stirred and incubated for 25 minutes at room temperature. After that, hydrazone was precipitated by centrifugation of the samples at 600 g for 25 minutes. 3M NaOH and 96% ethanol were sequentially added to the hydrazone precipitate, and the development of a raspberry color was observed.

The optical density of the samples was measured using a spectrofluorometer with excitation at 460 nm versus ethanol.

Morpho-Functional Analysis of Pancreatic and Liver Tissues

At the end of the experiment, the animals were euthanized by decapitation. Prepared liver and pancreas 0.5-0.5 cm in size were immediately placed in a fixative. The organs were fixed in a 4% solution of paraformaldehyde at a temperature of 25° C. for 72 hours. After fixation, the pieces were rinsed in tap water. Then the material was dehydrated. This was achieved by passing the pieces of organs through increasing concentrations of alcohol (70%>80%>90%>96%) leaving them for a day in each concentration. Finally, once the water was replaced by 96% alcohol, the material was placed in dioxane for 15 minutes, and then in xylene for 15 minutes. After complete clearing, the material was placed in a paraffin bath (paraffin and xylene mixture at a 1:1 ratio) in a thermostat for 30 minutes at 37° C. The material was then submerged in two changes of paraffin (30-35 minutes) in a thermostat at 56° C., and paraffin blocks were produced.

A series of 5 μm thick histological sections of tissue were cut using an MS-2 sliding microtome and placed on glass slides treated with a 1:1 mixture of protein and glycerol.

Dried preparations were stained with hematoxylin and eosin. Prior to staining, the sections were dewaxed in 2 changes of xylene for 5 minutes and passed through decreasing strengths of alcohol (96%>90%>80%>70% for 3 minutes in each) and finally distilled water for 5 minutes. The sections were stained with Bonier's hematoxylin for 1.5 minutes then washed in running water for 15-20 minutes and stained with eosin for 1 minute. Once stained, the sections were dehydrated once again in 70% and 96% alcohols (30 seconds in each) and cleared in dioxane and xylene for 2.5 minutes. The stained sections were enclosed in Canada Balsam and covered with coverslips. The nuclei of cells had a blue-violet color and the cytoplasm was pink.

To carry out a histochemical reaction to determine the level of liver fibrosis, Van Gieson's picro-fuchsin method of staining was used. To do this, the sections were first soaked with water and then re-stained with Bomer's hematoxylin for 3-4 minutes. The sections were then rinsed in distilled water and stained with Van Gierson's picro-fuchsin for 3 minutes. Once stained, the sections were rinsed in distilled water, dehydrated in 96% alcohol, cleared in dioxane and xylene, and enclosed in a balsam under a coverslip. As a result, hepatocyte nuclei had a dark brown color, collagen fibers were red and the cytoplasm was yellow. All parameters were measured using ImageJ software.

Determination of Protein Concentration

The protein concentration was measured using the Bradford protein assay. Bradford MM. Anal Biochem. 1976; 86: 193-200. To measure the protein concentration, 10% NaOH, distilled water, and Bradford reagent were added to the sample. Bradford reagent was prepared by mixing the initial solution (95% ethanol, 85% $H_3PO_4$ and Coomassie Brilliant Blue dye) with 95% ethanol and 85% $H_3PO_4$, and adjusting the resulting mixture to the desired volume with distilled water.

The absorbance was measured spectrophotometrically at 595 nm versus a control sample that contained distilled water instead of the test sample. The protein concentration was determined using a calibration curve and was expressed in mg/ml.

Statistical Processing of the Results

Statistical processing of the obtained results was carried out using the methods of variation statistics and correlation analysis using OrginLab Orgin® Pro 9.1 and StatSoft STaStica® 10 software. Brandt Z. Statistical methods for observations.-M.: Mir, 1975.-312 p. The hypothesis of normal distribution of samples was tested using the Shapiro-Wilk test. If a sample met the criteria of normal distribution, significance of differences between samples was determined using the Student's t-test. If a sample did not meet the criteria of normal distribution, significance of differences between samples was determined using the Mann-Whitney U test. Differences were considered statistically significant when $p<0.05$.

Results and Discussion

Biochemical and Anthropometric Effects of Zn-64 Stable Isotope in Aspartate Form in Animals Models of Obesity According to modern concepts, adipose tissue, producing a wide range of biologically active substances, is actively involved in the pathogenesis of obesity. Therefore, overweight occurring due to an increase in fat deposits is considered not only as a consequence of metabolic disorders during the development of obesity but also as an important factor that provokes and greatly complicates the course of the disease, contributing to the development of a number of obesity-related disorders.

To assess the effects of Zn-64 stable isotope in aspartate form on the development of obesity induced by the consumption of high-fat foods, some anthropometric values were evaluated in animal models of obesity and animals treated with Zn-64 stable isotope in aspartate form.

A characteristic morphological sign of the development of obesity is a significant increase in body weight due to accumulation and redistribution of adipose tissue. To confirm the development of obesity, the body mass index (BMI) or Quetelet index, which is body weight in kilograms divided by the square of the height in meters, was first determined. Novelli E., Diniz Y., Galhardi C. Anthropometrical parameters and markers of obesity in rats//Laboratory Animals.-2007.-No 41.-P. 111-119. BMI makes it possible to assess the body mass relationship to height and thereby indirectly assess whether the mass is insufficient, normal or excessive. In addition, BMI is used as an integral value, which allows us to characterize body composition and a degree of fat deposits because the character of distribution of adipose tissue in the body determines the risk of developing metabolic complications associated with obesity, which must be considered when examining obese patients. BMI is not only used to classify obesity but also to determine risks of developing obesity-related diseases.

The data obtained during the experiment show (Table 8) that on the $10^{th}$ week of the experiment, the mean body mass index of control animals was 0.60 $g/cm^2$ which value was within a reference range for animals of this age group. Novelli E., Diniz Y., Galhardi C. Anthropometrical parameters and markers of obesity in rats//Laboratory Animals.-2007.-No 41.-P. 111-119. BMI of animals eating high-fat diet was 1.14 times higher than BMI of animals of the control group (0.71 $g/cm^2$). It should be noted that the body mass index of rats receiving Zn-64 stable isotope in aspartate form during the experiment was lower than that of obese animals but slightly higher than the control values (0.65 $g/cm^2$). The obtained result indicates that Zn-64 stable isotope in aspartate form has a positive effect on the general metabolic status of animals and lays the groundwork for further studies aimed at finding out mechanisms of effects of Zn-64 stable isotope in aspartate form on obesity.

Since BMI is calculated based on weight, a decrease in BMI value may be directly related to the lower weight of animals that received Zn-64 stable isotope in aspartate form. Therefore, it was further investigated whether administration of Zn-64 stable isotope in aspartate form affected the weight and weight gain of animal models of obesity. The data obtained in the experiment show (FIG. 5) that the dynamics of weight gain by animals of the experimental groups differed significantly. Thus, animals that were maintained on a high-fat diet and received Zn-64 stable isotope in aspartate form gained less weight than animals that were only fed a high-fat diet. Particularly noticeable difference in the weight gain of animals of both groups was observed starting from the $4^{th}$ week of the experiment. An increase in body weight of animals eating a high-fat diet reached 103% by the end of the experiment, while animals that received intragastric injections of Zn-64 stable isotope in aspartate form gained almost as much weight as animals in the control group (62%).

It is known that the development of obesity, due to disruption of the coordinated work of a number of neurotransmitter and hormonal systems of the body, leads to disturbances at the level of appetite control and regulation of a feeling of satiety, which promotes excessive food intake and is often accompanied by the development of hyperphagia, a state of an abnormally great desire for food energy equivalent of which exceeds the energy needs of the body. L. Zhou, G. Sutton, J. Rochford.//Cell Metabolism.-2007.-Vol. 6, No 5.-P. 398-405.

To figure out possible mechanisms of the effect of decrease in the body weight of animals receiving Zn-64 stable isotope in aspartate form, the amount of food that animals consumed was analyzed. Table 8.

Comparing the data calculated for all experimental groups, it can be seen that there are no particular differences in the amount of food the animals ate on average per day. Thus, animals of the control group and the group of obese animals consumed about 35 g of food per day. But here it should be noted that animals in the control group were maintained on a standard diet while animals in the group of diet-induced obesity models consumed specially prepared high-fat diet the caloric content of which was significantly higher.

TABLE 8

Some anthropometric values, the amount and caloric content food (M ± m, n = 10)

| | Experimental groups | | | |
|---|---|---|---|---|
| | C | C + zinc | DIO | DIO + zinc |
| BMI (g/cm$^2$) | 0.60 | 0.59 | 0.71 | 0.65 |
| Weight gain as of the end of the experiment (%) | 59 | 59 | 103 | 62 |
| Amount of food consumed (g/day) | 34 | 32 | 35 | 29 |
| Caloric content of food (kJ/day) | 525 | 490 | 1001 | 823 |

C—control;
C + zinc—control on the background of administration of Zn-64 stable isotope in aspartate form;
DIO—diet induced obesity;
DIO + zinc—diet induced obesity on the background of administration of Zn-64 stable isotope in aspartate form.

Analysis of the results obtained, with due consideration of the caloric content of food consumed by animals, shows a significant difference in values. Despite the same amount of food eaten by animals of the control group and the group of diet-induced obesity models, the caloric content of food differed almost twice. A result obtained from the group administered with Zn-64 stable isotope in aspartate form seems quite interesting. Thus, animals of the control group and the group of diet-induced obesity models ate smaller amounts of standard and high-fat diets, respectively.

The dynamics of caloric content of food consumed by animals during 10 weeks of the experiment is shown in FIG. 6.

The data obtained suggest that Zn-64 stable isotope in aspartate form has an effect on the feeling of satiety because, having free access to food, animals injected with Zn-64 stable isotope in aspartate form consumed significantly less food compared to animals that were maintained only on a high-fat diet. A decrease in the amount of food consumed and, consequently, insignificant weight gain in animals that received Zn-64 stable isotope in aspartate form compared with animals in the group of diet-induced models can be explained by both direct and indirect effects of zinc on energy homeostasis.

Thus, summarizing the results of this phase of the study, administering Zn-64 stable isotope in aspartate form caused a decrease in the amount of food consumed per day, which, accordingly, was accompanied by a less pronounced weight gain in animals and normalization of their body mass index in comparison with similar values in obese animals that were not treated with Zn-64 stable isotope in aspartate form.

An early detection of Zn deficiency states is of paramount importance to prevent the onset and development of metabolic disorders. A laboratory sign of zinc deficiency is a decrease in its levels in the blood plasma (serum), but plasma zinc levels are labile and are influenced by many factors.

There are other approaches to determining zinc status. They, in particular, are based on the measurement of concentration of zinc-dependent proteins and, first of all, such enzymes as carbonic anhydrase, superoxide dismutase, lactate dehydrogenase and alkaline phosphatase, as well as metallothionein, a serum retinol-binding protein, in plasma (serum). One of the earliest markers of zinc deficiency is a decrease in the activity of serum alkaline phosphatase and carbonic anhydrase. As a result, stress ulcers caused by a high content of such zinc-containing enzyme as carbonic anhydrase in the mucosa are developed in the gastrointestinal tract. Therefore, to indirectly determine whether the development of obesity is accompanied by changes in zinc status, alkaline phosphatase activity in the blood serum of obese animals and animals treated with Zn-64 stable isotope in aspartate form was studied.

A significant decrease in the activity of this enzyme in animals maintained on a high-fat diet was observed (Table 9). Thus, the enzyme activity in these animals was 1.5 times lower than in animals of the control group. In animals treated with Zn-64 stable isotope in aspartate form, alkaline phosphatase activity was higher than both in the group of diet-induced obesity models and in the control group.

Thus, the obtained results indirectly confirm zinc deficiency in animal models of obesity and normal serum zinc levels in animals receiving Zn-64 stable isotope in aspartate form.

The gastrointestinal tract maintains whole-body zinc homeostasis. There are no true depots of this trace element in the human body. Zinc absorbed from the intestine enters the bloodstream. The whole blood contains about 7-8 mg/L of zinc, what is more, about ⅔ of this amount is transported by red blood cells. In plasma, about 80% of zinc is bound to albumin and the other 20% is bound to β2-macroglobulin and transferrin. Published data confirm dependence of the levels of this trace element on the concentration of albumin in the blood plasma. Brown, K. H. International Zinc Nutrition Consultative Group (IZiNCG) technical document #1. Assessment of the risk of zinc deficiency in populations and options for its control/K. H. Brown, J. A. Rivera, Z. Bhutta [et al.]//Food Nutr. Bull.-2004.-Vol. 25.-P. 99-203.

Therefore, albumin levels in untreated animal models of obesity and obese animals treated with Zn-64 stable isotope in aspartate form was further investigated. The data available from the experiment show that the pathogenesis of obesity is accompanied by a decrease in the serum albumin levels in animals. At the same time, administration of Zn-64 stable isotope in aspartate form had no effect on albumin values which remained similar to values in untreated obese animals (Table 9).

TABLE 9

Serum biochemistry of experimental animals (M ± m, n = 10)

| | groups | | |
|---|---|---|---|
| parameters | Control | DIO | DIO + zinc |
| Alkaline phosphatase activity, RU | 74.3 ± 12.1 | 37.2 ± 15.4* | 87.6 ± 18.7# |
| Albumin levels, RU | 219.2 ± 14.6 | 168.8 ± 16.8* | 166.2 ± 15.8* |
| Triglycerides, g/L | 2.55 ± 0.20 | 4.39 ± 0.73* | 2.79 ± 0.30# |
| Cholesterol, mmol/L | 2.42 ± 0.19 | 5.76 ± 0.87* | 2.83 ± 0.23# |
| Free fatty acids, mg/L | 23.60 ± 4.67 | 74.50 ± 9.23* | 31.62 ± 7.92# |

*the difference is significant versus the control group of animals;
the difference is significant versus the group of animal models of obesity
C—control;
C + zinc—control on the background of administration of Zn-64 stable isotope in aspartate form;
DIO—diet induced obesity;
DIO + zinc—diet induced obesity on the background of administration of Zn-64 stable isotope in aspartate form.

Considering that albumin acts as the major transport protein for zinc, a decrease in its concentration will cause a disruption in timely delivery of zinc to the organs, including liver, where synthesis of the main zinc-containing proteins occurs.

In general, this result is fully consistent with a decrease in alkaline phosphatase activity established above.

It has also been found that Zn-64 stable isotope in aspartate form has a positive effect on lipid metabolism in the body. A decrease in the levels of triglycerides, cholesterol and free fatty acids in the serum of animals that were fed a high-fat diet and treated with Zn-64 stable isotope in aspartate form was almost at the same level as in the control group of animals.

The pathogenesis of obesity due to metabolic disorders, mostly due to disturbances in hydrocarbon metabolism, is usually accompanied by an increase in glucose levels, which, if remain high for a long time, launch a number of pathological processes and become a significant factor that induces the development of insulin resistance and diabetes. Today, it is a proven fact that there is a relation between changes in the levels of trace elements, zinc in particular, and the onset of prediabetes and, in the absence of proper pharmacological correction, the development of diabetes. According to research results, concentrations of most trace elements in the body are constant, but in the case of zinc, a decrease in its levels in the blood serum of women with pre-diabetes has been shown. It is known that this element plays an important role in insulin synthesis in beta cells in the pancreas, and it also enhances susceptibility of tissues to this hormone. Chausmer, A. B. Zinc, insulin and diabetes. J. Am. Coll. Nutr. 1998, 17, 109-115.

In view of the above, the effects of Zn-64 stable isotope in aspartate form on glucose concentrations and insulin levels in the blood serum of animals eating a high-fat diet were investigated.

Based on the literature, fasting blood glucose levels within the range of 3.5-5.5 mmol/L are considered normal. An increase in this value over a certain time period to 7.0 mmol/L and above is regarded as a state of hyperglycemia and may be a predictor of the development of diabetes mellitus.

Serum glucose levels in animals from the control group and animals from the control group that received Zn-64 stable isotope in aspartate form were within the reference values (Table 10). The development of obesity was accompanied by a slight increase in the glucose levels which were normalized by the administration of Zn-64 stable isotope in aspartate form.

The effect of Zn-64 stable isotope in aspartate form on glucose levels may be directly related to its ability to stimulate the movement of the glucose transporter from inner cell compartments to adipocyte membranes, which contributes to the enhancement of intracellular glucose transport. It has also been found that Zn-64 stable isotope in aspartate form increases tyrosine phosphorylation of the insulin receptor β-subunit, thus improving glucose transport in the absence of insulin. The data indicate that Zn-64 stable isotope in aspartate form can act as an inhibitor of tyrosine-1B-phosphatase, an enzyme involved in the suppression of insulin signaling.

TABLE 10

Serum glucose concentrations and insulin levels in experimental animals (M ± m, n = 10)

| Experimental groups | Insulin levels, RU | Glucose levels, mmol/L |
|---|---|---|
| C | 0.133 ± 0.024 | 4.4 ± 0.3 |
| C + zinc | 0.145 ± 0.013 | 4.7 ± 0.2 |
| DIO | 0.216 ± 0.035* | 7.1 ± 0.1* |
| DIO + zinc | 0.149 ± 0.018# | 4.9 ± 0.2# |

*the difference is significant versus the control group of animals;
the difference is significant versus the group of animal models of obesity
C—control;
C + zinc—control on the background of administration of Zn-64 stable isotope in aspartate form;
DIO—diet induced obesity;
DIO + zinc—diet induced obesity on the background of administration of Zn-64 stable isotope in aspartate form.

An increase in glucose concentrations in obesity may be a consequence of a decrease in insulin secretion in β cells in the pancreas or its inadequate utilization by the tissues of the body. High glucose levels in the blood and other body fluids causes an increase in osmotic pressure resulting in the development of osmotic diuresis (increased loss of water and salts through the kidneys), which leads to dehydration of the body and deficiencies in sodium, potassium, calcium and magnesium cations, chlorine anions, phosphates and hydrocarbonates. In addition, elevated glucose levels cause non-enzymatic glycosylation of proteins and lipids, the intensity of which is directly proportional to glucose concentrations. As a consequence of this, the functions of many vital proteins are impaired resulting in various pathological changes in the body. Skybchyk V.//Ukrainian medical newspaper.-2006.-No 6.-P. 61-68. Campos. II Postgraduate Medicine.-2012.-No 126.-P. 90-97.

Considering changes in the serum glucose levels in animals, the next phase of this study was to determine the levels of insulin. In addition, a serum insulin level is an important parameter in diagnosing the development of insulin resistance and prediabetes. In obesity and metabolic syndrome, hyperinsulinemia is often caused by excessive production and secretion of insulin in β-cells in the pancreas, which is a compensatory response to a decrease in the sensitivity of peripheral tissues to insulin action. However, in later stages of the development of type 2 diabetes mellitus, serum insulin levels are significantly reduced, which is directly related to impaired ability of β-cells to produce insulin, impaired proinsulin processing and secretion of mature insulin, as well as a reduction in the number of secreting cells and deposition of amyloid in the islets of Langerhans. At the same time, the developing β-cell dysfunction causes further progression of diabetes mellitus. Boden.//Diabetes.-1997.-Vol. 46, No 3.-P. 3-10. Robertson R. P. et al.//Diabetes Mellitus.-2000.-P. 125-132.

An increase in the serum insulin levels was found in obese animals and a normalizing effect of Zn-64 stable isotope in aspartate form on the studied parameter in the group of animals maintained on a high-fat diet and receiving Zn-64 stable isotope in aspartate form. It should be emphasized that administering Zn-64 stable isotope in aspartate form to animals of the control group caused a slight increase in the insulin levels.

The effect of Zn-64 stable isotope in aspartate form on insulin levels may be associated with the direct involvement of this trace element in the processes of synthesis, deposition and release of insulin from β-cells in the islets of Langerhans as well as its ability to inhibit the action of insulinase. It is known that zinc is involved in the formation of hexameric proinsulin and contributes to the crystallization of insulin. It has been proven that zinc ions contribute to incorporation of insulin into the transport complex which ensures its delivery to target cells. Another possible mechanism was established in 1980 by Caulston and Dandona, who demonstrated that zinc has a powerful and stimulating, independent and complementary to insulin action, effect on lipogenesis in rat adipocytes. This discovery confirmed the involvement of zinc in controlling the effects of insulin, as this cation is secreted along with insulin in response to high glucose levels.

In addition, zinc plays an important role in protecting insulin and pancreatic beta cells from free radicals, as it is a structural component of antioxidant enzymes, such as superoxide dismutase, and a competitor to redox metals, such as iron. Zinc stimulates the expression of metallothioneins in the pancreatic cells known to be involved in the neutralization of a number of active oxygen metabolites and be able to prevent the destruction of beta cells.

Given the importance of maintaining physiological levels of zinc in the body to ensure the synthesis and secretion of insulin as well as its important role in the pancreas function, the effects of Zn-64 stable isotope in aspartate form on the overall morphofunctional properties of pancreas were further investigated.

Effects of Zn-64 Stable Isotope in Aspartate Form on the Morphofunctional Properties of Pancreas and Liver of Animal Models of Obesity The pancreas is a mixed gland, having both exocrine and endocrine function. The bulk of pancreas is composed of exocrine cells arranged in acini. Secretions from acini flow out of the pancreas through intercalated, intralobular and interlobular ducts and the main pancreatic duct. Clusters of exocrine cells, the acini, in animals from the control group (FIG. 7A-FIG. 7F) have a typical structure: cytoplasm in the apical pole is granular and brightly acidophilic, while the basal pole contains nuclei which are strongly basophilic.

In the animal models of DIO (obesity group) (FIG. 7A-FIG. 7F), there were acini with not very noticeably eosinophilic apical cytoplasm (FIG. 7A-FIG. 7F, arrows), which may be due to the accumulation of lipid inclusions, pancreatic fatty degeneration.

Administration of Zn-64 stable isotope in aspartate form to rats that were fed a standard diet did not change morphology of exocrine cells (FIG. 8A-FIG. 8F). After administration of Zn-64 stable isotope in aspartate form to rats having obesity (FIG. 8A-FIG. 8F), no fatty degeneration was found.

The endocrine part of the pancreas is composed of diffusely located islets of Langerhans. A morphometric study of the functional state of the endocrine pancreas during the development of induced obesity showed clear differences between the values obtained from all groups (FIG. 9). A cross-sectional surface area of the islets of Langerhans was significantly reduced in the animals from the obesity group (by 60%), which indicates a significant decrease in the functional activity of their endocrine pancreas. After administration of Zn-64 stable isotope in aspartate form to rats having obesity, the cross-sectional surface area of the islets of Langerhans increased by 43% compared with the obesity group, but still did not reach the control level (lower than the control value by 29%). Administration of Zn-64 stable isotope in aspartate form to rats that ate a standard diet caused a noticeable decrease in this value by 39% compared with the control group.

Since there is a direct relationship between the morphological and functional indicators of the state of pancreas, the data obtained show that the hormone-synthesizing activity of the pancreas in diet-induced obesity rat models is significantly reduced but it increases markedly with the administration of Zn-64 stable isotope in aspartate form, though it does not fully restore to the levels observed in the control group. In addition, an improvement in the state of the exocrine part of the pancreas after administration of the test substance against the background of the development of obesity was recorded, which is evidenced by disappearance of fatty degeneration, without a noticeable effect on exocrine cells in rats fed a standard diet.

The liver of control rats (FIG. 10A-FIG. 10D) has a classical lobular organization with a central vein running along the axis of each lobule. Hepatocytes of polygonal morphology with clearly defined nuclei, which contain several nucleoli each, are arranged into ordered hepatic cords spreading from the central vein. Binuclear hepatocytes are also found.

In animals from the obesity group (FIG. 10A-FIG. 10D), the hepatocyte shape changes from polygonal to rounded due to the deposition of lipid inclusions, which is a sign of fatty degeneration of the liver. The structure of the hepatic cords is disarranged and the number of binucleate cells in the field of view is reduced.

As a result of administration of Zn-64 stable isotope in aspartate form to rats having obesity (FIG. 11A-FIG. 11D) the structure of hepatic cords was restored, most hepatocytes of polygonal morphology showed no signs of fatty degeneration, binucleate cells were often found. Administration of Zn-64 stable isotope in aspartate form to rats eating a standard diet (FIG. 11A-FIG. 11D) did not cause any changes in the morphology of hepatocytes and the structure of hepatic lobules.

With the development of diet-induced obesity, significant morphometric changes in hepatocytes occurred (FIG. 12A-FIG. 12C). Thus, in animals from the obesity group, the nucleus area decreased by 25% (which is evidence of a decrease in transcriptional activity of the nucleus, also confirmed by its dark color and homogeneous structure with no nucleoli in the field of view), but the area of hepatocytes increased by 48% due to the deposit of a large number of lipid inclusions. At the same time, the nucleus-to-cytoplasm ratio significantly reduced (by 45%), a low level of which indicates that the functional activity of the cells decreased.

Administration of the test substance to obese rats improved their morphometric parameters. Thus, the area of hepatocytes in animals treated with Zn-64 stable isotope in aspartate form decreased by 41% versus untreated animal models of obesity (only a 13% increase compared to the control values, which is a sign of a decrease in the deposition of lipid inclusions by hepatocytes) and their nucleus-to-cytoplasm ratio increased by 31% compared to the obesity group (a decrease by 30% compared to the control group). However, the nucleus area is reduced versus the control values by 35% (i.e. decreased in relation to the values in the obesity group by 14%, which may be the result of a combined effect of two factors—a high-fat diet and Zn-64 stable isotope in aspartate form—on the nuclear activity).

The effect of Zn-64 stable isotope in aspartate form on the morphometric parameters in rats that were maintained on a standard diet consisted in the reduction of the nucleus area by 26%, the area of hepatocytes by 12% and the nucleus-to-cytoplasm ratio by 17%.

Liver fibrosis is characterized by excessive growth of connective tissue, an increased synthesis and deposition of collagen in the extracellular substance. In the samples taken from animals from the control group (FIG. 13A-FIG. 13D), most of the collagen fibers were in the region of triads formed by small interlobular vessels.

Samples taken from the animals from the obesity group (FIG. 13A-FIG. 13D) showed a noticeable increase in the number of collagen fibers in the triad region formed, as in the control group, by small perilobular capillary plexuses and larger interlobular vessels.

Samples taken from obese rats injected with Zn-64 stable isotope in aspartate form (FIG. 14) show similar levels of deposition of collagen fibers in the indicated places when compared to samples from the untreated obesity group. Administration of the test substance to rats that were fed a standard diet (FIG. 14A-FIG. 14D) caused no significant changes in the amount of collagen fibers in the perilobular and interlobular capillary plexuses.

Analysis of the area occupied by collagen fibers (FIG. 15) shows significant changes with the development of induced obesity. The area of collagen fiber deposits in the obesity group and in the group treated with Zn-64 stable isotope in aspartate form increased by a factor of 6.25 and by a factor of 6, respectively, versus the control group. No significant differences between the untreated obesity group and the obesity group treated with Zn-64 stable isotope in aspartate form were found. Administration of the test substance to rats eating a standard diet caused a significant increase in the area of deposition of collagen fibers (2-fold).

Thus, summarizing the results obtained, it can be said that Zn-64 stable isotope in aspartate form has a positive effect on the morphofunctional properties of the pancreas and liver of animal models of obesity.

Effects of Zn-64 Stable Isotope in Aspartate Form on the Serotoninergic System in Animal Models of Obesity Despite a proven fact that the development of obesity is primarily the result of an increased caloric intake and inadequate energy expenditure, a search for new pathogenetic mechanisms of weight gain is still relevant.

According to modern concepts, obesity, regardless of its etiology, leads to a disruption in the central regulatory mechanisms that affect behavioral responses, eating behavior, in particular. In the hypothalamus, mainly in the region of its paraventricular nuclei and lateral perifornical area, an integration of a multitude of impulses coming from the cerebral cortex and subcortical structures to the sympathetic and parasympathetic nervous systems takes place. A disruption in any link of this complex regulatory cascade can lead to changes in food intake, fat deposition and mobilization and, ultimately, to the development of obesity.

Important neurotransmitters involved in the regulation of eating behavior, appetite in particular, and affecting the feeling of satiety, include a number of biogenic amines, among which serotonin plays a decisive role. C. Portas et al., Progress in Neurobiology.-2000.-Vol. 60, No 1.-P. 13-35.

According to the theory of neurochemical imbalance of the central and peripheral nervous systems, overeating is a compensatory mechanism for obtaining pleasure due to insufficient production or sensitivity of neurotransmitters.

It is the central serotonergic system that is fundamental in regulating the feeling of hunger and satiety. Experiments demonstrated that an increase in serotonergic transmission in the brain caused a decrease in food intake. Injections of 5-HT into the paraventricular nucleus of the rat hypothalamus led to satiation of the animal, whereas, with food consumption, an increased yield of serotonin in the lateral hypothalamus was noted. These two sections of the hypothalamus are believed to perform the opposite function in regulating appetite: insufficient inhibition of serotonergic transmission in the lateral hypothalamus may be a cause of excessive food intake during obesity, and enhanced release of serotonin in the paraventricular nucleus of the hypothalamus may contribute to stress induced hypophagia.

The brain and intestines are the main organs producing serotonin in animals. Since serotonin does not cross the blood-brain barrier, the serotonin synthesis system is divided into central and peripheral, which operate separately from each other. A small amount of the hormone is in the plasma.

Several enzyme systems are involved in metabolic transformations of serotonin. These systems include enzymes for the serotonin synthesis and degradation, as well as an enzyme which determines how much tryptophan enters the kynurenine pathway. A. Meneses, G. Liy-Salmeron.//Annual Review of Neuroscience.-2012.-No 23.-P. 543-553. M. Donovan, L. Tecott.//Frontiers in Neuroscience.-2013.-No 7.-doi: 10.3389/fnins.2013.00036.

Tryptophan, an essential amino acid naturally produced by the body, is the immediate precursor of serotonin. Tryptophan is transported from the extracellular fluid to serotonergic neurons by a non-specific membrane transporter, which is believed to be involved in the transport of other neutral amino acids (valine, leucine, isoleucine). Therefore, levels of tryptophan in neurons and the intensity of its transport depend not only on the concentration of tryptophan, but also on the ratio of concentrations of competing neutral amino acids and the concentration of tryptophan.

Serotonin is synthesized through a two-step process catalyzed by two enzymatic systems. First, as a result of hydroxylation in the fifth position of the indole ring, tryptophan is converted to 5-hydroxytryptophan, a direct precursor of serotonin synthesis. The reaction of tryptophan hydroxylation is catalyzed by the rate-limiting enzyme tryptophan hydroxylase (tryptophan-5-monooxygenase, EC 1.14.16.4) in the presence of both molecular oxygen and pterin (tetrahydrobiopterin) as coenzymes. The rate of tryptophan hydroxylation directly depends on the availability of the substrate. The second step in the synthesis of serotonin is decarboxylation catalyzed by DOPA decarboxylase (also known as aromatic L-amino acid decarboxylase, EC 4.1.1.28).

In addition to participation of these enzymes in the synthesis of serotonin and other biologically active amines, both enzymes are actively involved in the regulation of circadian rhythms, bone remodeling, cell differentiation processes, immune response mechanisms and inflammation.

Inactivation of serotonin occurs by enzymatic degradation, which is mainly served by monoamine oxidase (EC 1.4.3.4). Under the action of MAO, serotonin is converted to 5-hydroxyindaldehyde, which, in turn, may reversibly convert to 5-hydroxytryptophol under the action of alcohol dehydrogenase. Under the action of acetaldehyde dehydrogenase, 5-hydroxyindaldehyde is irreversibly converted into 5-hydroxyindole acetic acid, which is then excreted with urine and feces. Sandler M. et al, Clinical Pathology.-1981.-No 34.-P. 292-302. S. Nilsson, N. et al, Acta medica Scandinavica.-1968.-No 184.-P. 105-108.

When released, serotonin influences various biological processes by binding to serotonin receptors (HTR). Its action is then terminated by uptake in cells through the serotonin transporter (SERT, Slc6a4).

In addition to oxidative deamination of serotonin, other pathways of serotonin metabolism are possible, for example, the pathways of acetylation and glucuronic acid and sulphate ester conjugations. There is a pathway for serotonin metabolism, which is accompanied by the formation of melatonin.

Medical studies have shown that a disorder in metabolic transformations of serotonin is often not only a consequence, but also one of the main factors that trigger the development of overweight and obesity. Molecular and biochemical disorders at the level of different phases of serotonin metabolism, its transport through cell membranes and deposition mechanisms leading to changes in serotonin concentrations both in the central nervous system and in the periphery may be one of the defining pathological bases for the formation of immune neuroendocrine imbalance and maintaining proinflammatory reactions. Imbalance of the serotoninergic system is an underlying cause of the development of a number of pathological conditions of the body and mental disorders, including schizophrenia, various psychoses, depression and anxiety. Depressive states are often accompanied by an increased appetite, which causes excessive food intake, especially carbohydrate-rich foods.

Recent research data have shown that zinc can modulate serotonergic function via the 5-HT1A receptors (5-HT1AR); however, the exact mechanisms of its action are unknown. Considering the above, as well as the importance of zinc for proper functioning of the neurohormonal system of the brain, its involvement in the metabolism of tryptophan, a key molecule of serotonin synthesis, and a modulating effect of zinc on the serotonergic system, the main indicators that would allow a general assessment of serotonin metabolism in experimental animals were further analyzed. For this purpose, serotonin and tryptophan levels were determined, as well as the activity of key enzymes involved in the serotonin metabolism (tryptophan hydroxylase, tryptophan decarboxylase, indole amide dehydrogenase and monoamine oxidase) in the blood serum, brain and duodenum of animals which were fed a high-fat diet and injected with Zn-64 stable isotope in aspartate form.

In general, the results of this study show a significant imbalance of the serotonergic system in obese animals occurring both in the peripheral and in central serotonergic systems, which can be one of the trigger mechanisms for the development and progression of obesity.

In the peripheral system, serotonin is localized in enterochromaffin cells of the gastrointestinal mucosa. It is there that about 80% to 95% of the total amount of this hormone in the body is synthesized. Serotonin is also synthesized in the pineal gland. Cote F. et al, PNAS USA.-2003.-Vol. 100.-P. 13525-13530. Eddahibi S. The serotonin pathway in pulmonary hypertension./Eddahibi S., Adnot S.//Arch. Mai. Coeur. Vaiss.-2006.-Vol. 99—P. 621-625.

Serotonin synthesized in the intestine is stored in platelets; it is also present in other peripheral tissues, such as the mammary gland, liver, bones, as well as in β-cells in the pancreas. Peripheral serotonin is involved in the regulation of intestinal movements, vasoconstriction processes and blood pressure. Serotonin also regulates the levels of glucose in the blood plasma, thrombogenesis, cardiac rhythm and the strength of heart contractions.

Significant inhibition of the peripheral serotoninergic system has been established, evident in a decreased activity of all key enzymes against the background of depletion of the tryptophan pool. Despite the identified changes, serotonin levels in the duodenum of animal models of obesity significantly exceeded the values in the control group (Table 11).

These results are generally consistent with the current concept that the intestinal serotonin correlates with the development of obesity and that the levels of serotonin in the intestines in obese people are increased significantly. The accumulation of serotonin causes an increase in serum glucose concentrations, thus contributing to the development of diabetes and obesity.

TABLE 11

Main indicators of functioning of the peripheral serotonergic system (duodenum) in animals from experimental groups (M ± m, n = 10)

| Experimental variable | C | C + zinc | DIO | DIO + zinc |
|---|---|---|---|---|
| Tryptophan, µg/g | 169.2 ± 12.6 | 154.7 ± 13.6 | 76.3 ± 9.74 * | 89.4 ± 8.99 * |
| Serotonin, µg/g | 6.56 ± 0.98 | 7.41 ± 0.54 | 14.6 ± 1.64 * | 9.73 ± 0.82 *,# |
| Tryptophan hydroxylase activity, RU/mg protein | 398 ± 78 | 375 ± 61 | 210 ± 69 * | 253 ± 58 * |
| Tryptophan decarboxylase activity, RU/mg protein | 0.81 ± 0.25 | 0.79 ± 0.22 | 0.65 ± 0.23 | 0.78 ± 0.19 |
| Monoamine oxidase activity, RU/mg protein | 3.33 ± 0.04 | 3.82 ± 0.07 | 1.55 ± 0.07 | 1.72 ± 0.03 |
| Indoleamine dioxygenase activity, µmol/mg protein | 2348 ± 301 | 2150 ± 231 | 1378 ± 305* | 1768 ± 274 * |

* the difference is significant versus the control group of animals;
the difference is significant versus the group of animal models of obesity
Note:
C—control;
C + zinc—control on the background of administration of Zn-64 stable isotope in aspartate form;
DIO—diet induced obesity;
DIO + zinc—diet induced obesity on the background of administration of Zn-64 stable isotope in aspartate form.

Analysis of the serum serotonin and tryptophan levels in animals having obesity showed a significant decrease in the concentrations of both substances, which may be a direct consequence of inhibition of the reactions of serotonin synthesis in enterochromaffin cells of the gastrointestinal mucosa (Table 12).

An additional factor contributing to low serotonin levels in the blood is the activation of monoamine oxidase.

Modulation of the peripheral serotoninergic system can be a good anti-obesity treatment strategy, as it can reduce obesity and increase insulin sensitivity.

Despite the importance of maintaining physiological levels of peripheral serotonin, it is central serotonin that plays a key role in the regulation of energy homeostasis. An inverse relationship between central serotonin level and food intake was established. In the CNS, serotonin is synthesized in the hypothalamus and brainstem. It helps regulate mood, sleep-wake cycles and diet.

Inhibiting serotonin synthesis in the brain via intraventricular injection of p-chlorophenylalanine, an irreversible inhibitor of tryptophan hydroxylase, induces hyperphagia and weight gain in rats. Serotonin reuptake inhibitors and monoamine oxidase inhibitors reduce food intake. Thus, serotonin in the central nervous system functions as an anorexigenic neurotransmitter.

TABLE 12

Serum levels of tryptophan and serotonin and monoamine oxidase activity in animals from experimental groups (M ± m, n = 10)

| Experimental variable | Experimental groups | | | |
|---|---|---|---|---|
| | C | C + zinc | DIO | DIO + zinc |
| Tryptophan, µg/g | 57.38 ± 5.73 | 56.12 ± 7.58 | 38.3 ± 6.72 * | 66.65 ± 9.62 |
| Serotonin, µg/g | 9.53 ± 0.72 | 10.16 ± 0.62 | 3.88 ± 0.34 * | 6.33 ± 0.51 *,# |
| Monoamine oxylase activity, RU/mg protein | 2.69 ± 0.06 | 2.52 ± 0.03 | 3.91 ± 0.04 * | 3.11 ± 0.08 *,# |

\* the difference is significant versus the control group of animals;
the difference is significant versus the group of animal models of obesity
Note:
C—control;
C + zinc —control on the background of administration of Zn-64 stable isotope in aspartate form;
DIO—diet induced obesity;
DIO + zinc—diet induced obesity on the background of administration of Zn-64 stable isotope in aspartate form.

The pathogenesis of obesity in rats was accompanied by a significant drop in the tryptophan levels in the brain of animals, which may be caused by impaired transport of this amino acid across the blood-brain barrier (Table 13).

It is known that the transport of aromatic amino acids and branched-chain amino acids across the blood-brain barrier occurs with the involvement of a specific carrier and is competitive, therefore elevated serum concentrations of branched-chain amino acids, typical for obesity, will affect transport of tryptophan across the blood-brain barrier. C. Newgard, J. An, J. Bain.//Cell Metabolism.-2009.-Vol. 9, No 4.-P. 311-326. E. del Amo et al.,//european journal of pharmaceutical sciences.-2008.-No 35.-P. 161-174.

TABLE 13

Main indicators of functioning of the central serotonergic system (brain) in animals from experimental groups (M ± m, n = 10)

| Experimental variable | Experimental groups | | | |
|---|---|---|---|---|
| | C | C + zinc | DIO | DIO + zinc |
| Tryptophan, µg/g | 99.24 ± 8.53 | 87.71 ± 3.41 | 6.66 ± 1.08 * | 31.56 ± 2.14 *,# |
| Serotonin, µg/g | 27.26 ± 2.76 | 25.51 ± 2.71 | 7.4 ± 1.63 * | 20.1 ± 3.21 *,# |
| Tryptophan hydroxylase activity, RU/mg protein | 281 ± 27 | 291 ± 29 | 245 ± 18 | 286 ± 17 |
| Tryptophan decarboxylase activity, RU/mg protein | 1.32 ± 0.43 | 1.63 ± 0.41 | 2.19 ± 0.67 | 1.86 ± 0.37 |
| Monoamine oxidase activity, RU/mg protein | 0.84 ± 0.08 | 0.91 ± 0.06 | 1.19 ± 0.07 | 0.99 ± 0.08 |
| Indoleamine dioxygenase activity, µmol/mg protein | 1097 ± 285 | 1178 ± 267 | 2438 ± 290 * | 2007 ± 175 * |

\* the difference is significant versus the control group of animals;
the difference is significant versus the group of animal models of obesity
Note:
C—control;
C + zinc—control on the background of administration of Zn-64 stable isotope in aspartate form;
DIO—diet induced obesity;
DIO + zinc—diet induced obesity on the background of administration of Zn-64 stable isotope in aspartate form.

Given a close metabolic connection between serotonin and tryptophan, a natural consequence of the lack of the latter will be a decrease in serotonin levels.

Impairment of serotoninergic transmission is one of the factors contributing to the occurrence of depressive states and can be considered as one of the key causes of obesity. It is known that people with congenital or acquired defects of the central serotonergic system develop subjective negative reactions to starvation, which is accompanied by a decrease in the production of serotonin. In such cases, even minor starvation may trigger the development of depressive states. Therefore, such people consume food in quantities that exceed their physiological needs.

Thus, low serotonin levels in the ventromedial and paraventricular nuclei of hypothalamus induce excessive food intake and cause insulin hypersecretion, which leads to a decrease in sensitivity of peripheral tissues to the action of this hormone and the development of insulin resistance.

Changes in the activity of enzymes involved in the serotonin metabolic pathway that were identified during this study contribute to further depletion of serotonin reserves in the brain. Thus, a decrease in the activity of tryptophanhydroxilase, an enzyme limiting the process of serotonin synthesis, occurring on the background of activation of monoamine oxidase, an enzyme that ensures the degradation of serotonin, was observed.

Increased activity of indolamine-2,3-dioxygenase is indicative of the activation of an alternative tryptophan metabolic pathway, which not only contributes to further depletion of the pool of this amino acid, but also serves as a source of formation of a number of neurotoxic compounds.

Administration of Zn-64 stable isotope in aspartate form to animals that were fed a high-fat diet led to normalization of most of the experimental variables. Thus an increase in serotonin levels in the brain due to an increase in tryptophan levels is observed and, accordingly, activation of serotonin synthesis against the background of inhibition of an alternative way of its transformation and reduction in the rate of serotonin degradation by monoamine oxidase. A similar effect was found in the duodenum and serum.

Thus, the effect of zinc is complex and is implemented at the level of functioning of both the central and peripheral serotonergic systems. These results substantiate the advisability of therapeutic use of zinc preparations as monotherapy or in combination with other drugs for the improvement of overall metabolic status in the development of obesity and prevention of the obesity-related disorders.

Effects of Zn-64 Stable Isotope in Aspartate Form on Prooxidant-Antioxidant Balance in Animal Models of Obesity Free radical reactions that are necessary for the formation of enzymes, activation of transcription factors, oxidation of xenobiotics and bactericidal protection are the basis of normal functioning of the cell. In addition, they are involved in the expression of genes, transduce hormonal and cellular signals and regulate the processes of cell reproduction. Thus, reactive oxygen species and reactive nitrogen species are produced naturally in the human body and are key by-products in the metabolic process. Antioxidants maintain levels of free radicals within physiological limits. A balance between antioxidant defense and free radical oxidation is necessary for proper function of cells. When the amount of free radicals exceeds the activity of antioxidant defense, a phenomenon called oxidative stress is generated.

Oxidative stress and the resulting tissue damage and cell death contribute to many pathological conditions. Excess production of free radicals and/or depletion of the defense systems leads to the prooxidant-antioxidant imbalance, which in turn causes damage to the protein structures in cells, lipid bilayer of cell membranes and nucleic acids. Since the lipid bilayer is a component of all cell membranes, lipid peroxidation mediated by free radicals is one of the important reasons for the cell membrane damage followed by the cell death. Degradation of membrane lipids causes an increased fluidity of the cell membrane and its permeability to ions, disrupting cellular homeostasis as a whole. Products of free radical oxidation (4-hydroxyalkene, malonic dialdehyde, etc.) are highly mutagenic and cytotoxic.

Epidemiological, clinical and animal studies have shown that obesity is associated with an altered redox state and an increased metabolic risk. In this case, oxidative stress may be not only a consequence, but also a trigger for the development of disorders in obese people. It is oxidative stress that is one of the factors that cause adipocyte dysfunction. Excess oxidants, initially produced by a growing mass of adipose tissue, stimulate sensitive to oxidative stress signaling pathways, which are mediated by the transcription factor NF-kB and JNK and p38-MAPK kinases, and activate a number of protein kinases (PKB, PKC, etc.).

In addition, oxidative stress activates preadipocyte differentiation and stimulates hypertrophy of mature adipose cells. Increased production of ROS in the accumulated adipose tissue further leads to the induction of oxidative stress in the bloodstream, which contributes to the spread of oxidative stress to organs distant from the fat depot.

Increased glucose levels, along with disorders of lipid metabolism and elevated concentrations of free fatty acid, determine the mechanisms of formation and progression of oxidative stress specific for obesity. It is believed that hyperglycemia-induced oxidative stress occurs both as a result of direct activation of ROS formation reactions and as a result of disturbance of cell redox homeostasis.

The next phase of this study aimed to assess the prooxidant-antioxidant balance in animal models of obesity treated with Zn-64 stable isotope in aspartate form.

The concentrations of lipid peroxidation products (LOPs) serve as an informative criterion making it possible to draw a conclusion about intensity of oxidative processes. There are primary lipid peroxidation products (such as conjugated dienes) and secondary lipid peroxidation products (such as aldehydes, malonic aldehyde in particular), which are formed as a result of breakdown of carbon-carbon double bonds in the carbon skeletons of oxidized molecules. Subsequently, the initiation of lipid peroxidation leads to the formation of conjugated Schiff bases of phospholipids and malonaldehyde-like products, which cause disturbances in the ordered orientation of phospholipid molecules and affect lipoprotein intermolecular interactions and configuration of the basement membrane.

Considering the above, the concentrations of primary LOPs—conjugated dienes (CD), secondary products—TBA-reactive substances (TBARSs) and end products—Schiff bases (SB) were determined in animals treated with Zn-64 stable isotope in aspartate form. Taking into account that obesity is accompanied by the development of systemic oxidative stress which covers most tissues to various extents and leads to the disruption of integrity of cell membranes and admission of lipid peroxidation products to the bloodstream, values characterizing the state of the prooxidant-antioxidant system were determined in the blood serum of animals and analyzed.

Elevated serum levels of primary products of free radical lipid oxidation (by 1.86 times) suggest that the initial phase of lipid peroxidation actively occurs even after ten weeks of experimental obesity (Table 14). This result can be explained from the standpoint of disturbed lipid metabolism, namely impairment of the processes of transportation of fatty acids and, accordingly, an increase in the plasma levels of free and esterified fatty acids, direct substrates for the action of active oxygen species. On the other hand, accumulation of lipid peroxidation products in serum may be a direct result of violation of the integrity of cell membranes due to oxidative destruction of their lipid component and permeability of lipid oxidation products into the bloodstream.

An additional factor that may contribute to increased oxidative stress in the development of obesity is a significant activation of MAO (demonstrated at the previous phase of this study), an enzyme involved in the ROS production.

TABLE 14

Serum levels of lipid peroxidation products in animals from experimental groups (M ± m, n = 10)

| Experimental groups | Conjugated dienes, nmol/mg protein | TBA-reactive substances, nmol/mg protein | | Schiff bases, RU/mg protein |
|---|---|---|---|---|
| | | Spontaneous accumulation | $Fe^{2+}$-ascorbate-induced accumulation | |
| C | 0.021 ± 0.001 | 0.006 ± 0.0003 | 0.033 ± 0.005 | 41.31 ± 2.47 |
| DIO | 0.039 ± 0.002 * | 0.029 ± 0.002 * | 0.61 ± 0.003 * | 168.86 ± 8.15 * |
| DIO + zinc | 0.025 ± 0.008 | 0.005 ± 0.0003 # | 0.15 ± 0.008 *,# | 56.27 ± 4.33 *,# |

* the difference is significant versus the control group of animals;
the difference is significant versus the group of animal models of obesity
Note:
C—control;
C + zinc—control on the background of administration of Zn-64 stable isotope in aspartate form;
DIO—diet induced obesity;
DIO + zinc—diet induced obesity on the background of administration of Zn-64 stable isotope in aspartate form.

An increase in the levels of CD was accompanied by accumulation of secondary POLs, namely TBA-reactive substances. Thus, the serum levels of TBA-reactive substances in animals having obesity were 4.8 times higher in comparison with the control value. In the case of Fe+2-ascorbate-dependent accumulation of TBA-reactive substances, this value exceeded the result obtained in the group of control animals 20-fold, which suggests a significant contribution of non-enzymatic reactions of initiation of lipid peroxidation processes to prooxidant-antioxidant imbalance in obese animals.

Such a significant increase in the concentrations of aldehyde POLs is regarded as an unfavorable marker, since these substances can bind to proteins to form stable adducts. Their formation may affect protein function. In addition, proteins modified in this way have immunological properties and may cause autoantibody production.

Changes in the levels of primary and secondary products were accompanied by accumulation of the end products of lipid peroxidation, Schiff bases, which are formed as a result of condensation of aldehydes, including malondialdehyde, or ketones with amino groups of proteins and lead to impairment of the structural and functional characteristics of the latter. According to the obtained data (table), a significant increase in the levels of Schiff bases was observed in the serum of animals having obesity. Thus, this value was 4 times higher than in the group of control animals. The levels of the end products of lipid peroxidation characterizes the duration of oxidative homeostasis disorders, therefore, given a significant growth of this value in this study, the long-term activation of free radical reactions may be discussed.

Thus, elevated levels of lipid peroxidation products on the 10th week of obesity development clearly indicate that oxidative stress has a systemic nature and that this process is chronic, which is an unfavorable prognostic marker, as these metabolites are extremely toxic compounds and their negative impact is exhibited at different levels and leads to DNA molecule damage, destruction of protein molecules and glycosaminoglycans, changes in the lipid composition of cell membranes and disruption of membrane-associated processes.

Activation of lipid peroxidation processes may indirectly indicate an increase in the concentrations of ROS. An excess of ROS may directly activate a number of serine-threonine kinases, such as, PKC, AKT/PKB, mTOR, GSK-3 and p38 MAPK. These synergistically acting protein kinases reduce insulin sensitivity of cells by selective phosphorylation of serine and threonine residues in IRS molecules and contribute to the development of resistance of insulin-dependent cells to this hormone.

Administration of Zn-64 stable isotope in aspartate form to animals helped normalize the levels of primary, secondary and end LOPs, which serves as additional evidence of the ability of Zn-64 stable isotope in aspartate form to influence an overall prooxidant-antioxidant status of the body.

According to modern concepts, reactive oxygen species not only activate lipid peroxidation processes but also cause oxidative destruction of protein molecules, causing disruption of conformation of soluble and membrane-bound enzymes, receptors and ion channels, which ultimately leads to the loss of their biological activity (enzymatic, receptor, transport, etc.). Oxidative modification of proteins and accumulation of structurally modified molecules is an important factor that may potentially contribute to the production of new antibodies, thus provoking an autoimmune reaction. Berlett B. S., Stadtman E. R. J. Biol. Chem.—1997.-V.272, No 33.-P. 20313-20316.

Under the action of ROS, the native conformation of proteins is disturbed resulting in the formation of large protein aggregates, or vice versa, fragmentation of protein molecules. Hydroxyl radicals most often cause protein aggregation and—in combination with superoxide anion—fragmentation with the formation of low molecular weight fragments. Lipid radicals may also cause fragmentation of protein molecules. The formation of carbonyl groups (aldehyde or ketone groups of amino acid residues) may serve as a marker of oxidative protein damage.

According to modern concepts, all amino acid residues in proteins may be modified, but tryptophan, tyrosine, histidine and cysteine residues are the most sensitive. ROS attack functional groups of amino acids that make up proteins, leading to the formation of primary amino acid radicals capable of interacting with neighboring amino acid residues. In general, a complex picture of the damaging effect of ROS on protein macromolecules is faced. Radicals, formed as a result of tyrosine oxidation, may interact with each other, forming bityrosine cross-links in proteins. Bityrosine cross-links increase resistance of proteins to the action of proteases, creating prerequisites for the accumulation of functionally inactive proteins in the body. Oxidation of tryptophan is also associated with the formation of covalent cross-links, which is an additional factor that causes aggregation of protein molecules. Rojas V. C. et al., Arch. Med. Res.-1996.-V.27, No 1.-P.1-6. Archakov A. I., Mokhosoev I. M. Modification of proteins with active oxygen and their decomposition//Biochemistry.-1989.-Vol. 54, No 2.-P. 179-185.

Oxidative modification of proteins plays an important role in protein metabolism in the body. Accumulation of oxidized proteins is regarded as one of the factors regulating the synthesis and breakdown of proteins and activation of multicatalytic proteases that selectively destroy oxidized proteins. A degree of oxidative damage to protein molecules may be assessed by the accumulation of carbonyl derivatives, aldehyde- and ketone-dinitrophenyl-hydrazones of a neutral nature in particular. Aldehyde-dinitrophenyl-hydrazones, detected at a wavelength of 356 nm, are early markers of oxidative degradation of proteins and indicate the initial stages of damage to protein molecules under the action of free radicals, while ketone-dinitrophenyl-hydrazones, which are detected at 370 nm, are considered late markers of oxidative damage to proteins.

Since, unlike lipid peroxidation products, carbonyl derivatives are much more stable, this makes it possible to consider products of oxidative modification of proteins as markers of oxidative damage in tissues.

Thus, an increase in the number of modified proteins may be considered as an early criterion for the damage of tissues by free radicals and a marker of the depletion of antioxidant defense system in the body.

These studies revealed an increase in the serum levels of oxidatively modified proteins in animal models of obesity (Table 15) with more pronounced changes in the levels of aldehyde-dinitrophenyl-hydrazones that indicate an active stage of the development of oxidative stress and metabolic disorders accompanied by enhanced formation of free radicals. In general, elevated concentrations of carbonyl derivatives in oxidatively modified proteins in the serum of animals having obesity against the backdrop of intensification of lipid peroxidation processes can be regarded as indisputable evidence of prolonged oxidative stress. Thus, taking into account the data obtained, it can be said that the development of obesity is accompanied by activation of free radical oxidation of proteins, which makes itself evident in the increased amounts of carbonyl derivatives formed by oxidative modification of proteins with absorption peaks at 356 and 370 nm.

TABLE 15

Serum levels of products of oxidative modification of proteins in animals from experimental groups (M ± m, n = 10)

| Groups | Aldehyde-dinitrophenyl-hydrazones, nmol/mg protein | ketone-dinitrophenyl-hydrazones, nmol/mg protein |
|---|---|---|
| C | 0.187 ± 0.009 | 0.255 ± 0.023 |
| DIO | 0.698 ± 0.041 * | 0.571 ± 0.035 * |
| DIO + zinc | 0.253 ± 0.012 *,# | 0.200 ± 0.024 *,# |

* the difference is significant versus the control group of animals;
the difference is significant versus the group of animal models of obesity
Note:
C—control;
C + zinc—control on the background of administration of Zn-64 stable isotope in aspartate form;
DIO—diet induced obesity;
DIO + zinc—diet induced obesity ont he background of administration of Zn-64 stable isotope in aspartate form.

The processes of modification of protein molecules by active oxygen species occur not only in pathological conditions. Thus, in physiological conditions, there is a certain level of oxidatively modified proteins in cells, reflecting the balance between the rate of proteolytic degradation of these damaged, "used" molecules and the rate of their synthesis. In some cases, oxidative inactivation is a marker stage that increases sensitivity of proteins to the action of proteases, since proteolytic enzymes break down modified protein molecules much faster than native ones. Therefore, elevated levels of carbonyl derivatives in animals having obesity may not only indicate the development of oxidative stress, but also give evidence of significant impairments in the mechanisms of control and regulation of degradation of structurally modified proteins and, peculiarly, proteolytic enzymes that ensure implementation of this process.

In animals that were fed a high-fat diet during the entire experiment and received injections of Zn-64 stable isotope in aspartate form, the levels of aldehyde-dinitrophenyl-hydrazones exceeded the benchmark but were lower compared to the values in untreated animals having obesity. As for keton-dinitrophenyl-hydrazones, their concentration remained within the control value. Such results correlate with the data showing a decrease in the levels of LOPs and may suggest a decrease in the intensity of free radical oxidation reactions.

According to modern concepts, in cells, along with modification of proteins by ROS, there is a so-called non-oxidative pathway for the formation of carbonyl derivatives, which consists in modifying protein molecules by aldehydes. Thus, the experiments of Burcham P.C. et al. showed that incubation of proteins with various aldehydes, including MDA, induced an increase in the number of oxidatively modified proteins in a concentration-dependent manner. Since administration of Zn-64 stable isotope in aspartate form to obese animals resulted in a decrease in the levels of LOPs, it appears that the observed decrease in the degree of oxidative modification of proteins may partly be associated with inhibition of the non-oxidative formation of carbonyl derivatives.

The basis of the positive effect of zinc on the overall oxidative status that was identified may be both its direct influence on the processes of free radical oxidation at the stage of initiation of chain reactions and its inclusion in the active centers of antioxidant enzymes. It is also important to mention a membrane stabilizing effect of this trace element, which may be one of the mechanisms of its antioxidant action as well. The role of zinc as an antioxidant is confirmed by its ability to act as an intramolecular stabilizer that prevents formation of disulfide structures. In addition, zinc competitively replaces copper and iron ions which trigger the formation of free radicals.

The free radical processes are controlled and regulated by antioxidant defense (AOD), a complex multicomponent and multi-level system. In physiologically normal state, equilibrium between the levels of free radical oxidation reactions and the activity of this system is maintained, which ensures maintenance of lipid peroxidation processes at a stationary, rather low level.

The antioxidant defense system consists of non-enzymatic and enzymatic units. Non-enzymatic antioxidants provide mainly rapid inactivation of free radicals of oxygen and nitrogen, while enzymatic antioxidants are referred to the terminal system of long-term defense of the body.

Superoxide dismutase (EC1.15.1.1) is one of the key enzymes of AOD. This enzyme catalyzes a reaction of neutralization of superoxide anion radicals by their dismutation into less reactive molecules of hydrogen peroxide and triplet oxygen. SOD is the only among the most active antioxidant enzymes that breaks the chains of oxygen-dependent free-radical reactions in the cells of aerobic. Poberezkina N. B., Osinskaya L. F. Biological role of superoxide dismutase//Ukr. biohim journal.-1989.-Vol. 61, No 2.-P. 14-27. Dudochnik L. B., Tikhaze A. K., Alesenko A. V. et al. Change in the activity of superoxide dismutase and glutathione peroxidase in the process of lipid peroxidation intensification in liver ischemia//Bul. exp. biol. Med.-1981.-Vol.XCI, No 4.-P. 451-453.

Given the leading role of SOD in reactive oxygen species metabolism and a significant contribution of superoxide anion radicals to the induction and development of oxidative stress, the activity of Cu—Zn-dependent SOD in the serum of animal models of obesity treated and untreated with Zn-64 stable isotope in aspartate form was investigated.

In this experiment, a statistically significant decrease in SOD activity was found in animals that ate a high-fat diet. Administration of Zn-64 stable isotope in aspartate form to experimental animals caused an increase in SOD activity not only in comparison with the values in untreated animal models of obesity, but also relative to the control (Table 16).

TABLE 16

Serum superoxide dismutase and catalase activities in animals from experimental groups (M ± m, n = 10)

| | Experimental groups | | |
|---|---|---|---|
| | C | DIO | DIO + zinc |
| Superoxide dismutase activity, RU/ min per mg protein | 3.36 ± 0.36 | 2.65 ± 0.41 * | 4.5 ± 0.43 *,# |
| Catalase activity, µmol $H_2O_2$/min per mg protein | 0.52 ± 0.05 | 0.43 ± 0.02 * | 0.48 ± 0.02 # |

* the difference is significant versus the control group of animals;
the difference is significant versus the group of animal models of obesity
Note:
C—control;
C + zinc—control on the background of administration of Zn-64 stable isotope in aspartate form;
DIO—diet induced obesity;
DIO + zinc—diet induced obesity on the background of administration of Zn-64 stable isotope in aspartate form.

Taking into account a certain zinc deficiency characteristic of the pathogenesis of obesity, restoration of the activity of this enzyme following the administration of the solution of Zn-64 stable isotope in aspartate form may be a consequence of normalization of its levels in the body and its active involvement in the regulation and synthesis of zinc-dependent enzymes, SOD in particular.

A decrease in SOD activity can be viewed as a consequence of a certain depletion of the antioxidant defense system due to gradual damage of its components by free radicals and LOPs. Thus, according to modern concepts, activity of this enzyme is closely related to the intensity of LOP processes since excessive accumulation of toxic secondary products of lipid oxidation causes inhibition of the activity of SOD and other enzymes of the antioxidant system. Literature review and data analysis on the involvement of ROS in the oxidative degradation of proteins suggest that a decrease in the enzymatic activity of SOD may be due to an oxidative modification of the enzyme molecule. Since SOD is a metal-containing enzyme, protein-damaging oxygen radicals can be formed directly in the active center of the enzyme. In this case, the hydroxyl radical, OH$^-$, formed in the reactions of Fenton and Haber-Weiss from hydrogen and superoxide, acts as a direct agent that inactivates the enzyme. Thus, the experiments of Salo D.C. et al. show that incubation of superoxide dismutase in a medium containing oxygen radicals leads to the cleavage of an enzyme molecule resulting in the formation of additional protein fractions. The authors explain the result by oxidative inactivation of superoxide dismutase when exposed to H2O2. Such a view is consistent with the ability of copper atoms in the active center of the enzyme to accelerate formation of free radicals. Another argument in favor of the involvement of metals with several common oxidation states in SOD inactivation is the fact that Mn2+-containing superoxide dismutase is not susceptible to oxidative degradation when incubated with $H_2O_2$.

Since an important antioxidant enzyme in the system is catalase, which neutralizes hydrogen peroxide formed as a result of dismutation of the superoxide anion radical by superoxide dismutase, the activity of this enzyme in animal models of obesity treated and untreated with Zn-64 stable isotope in aspartate form was assessed. Similar to a decrease in SOD activity, an inhibition of catalase activity in untreated obese animals was observed.

A decrease in the activity of both enzymes against the background of activation of lipid peroxidation processes is regarded as a negative prognostic event contributing to further escalation of free radical processes.

Administration of Zn-64 stable isotope in aspartate form caused a slight increase in the activity of catalase when compared with the results obtained from the group of untreated animal models of obesity, which generally correlated with the previously established normalization of prooxidant-antioxidant balance.

Normalization of the activities of the studied antioxidant enzymes following administration of the test substance is consistent with the literature data on other forms of this ion. Thus, it was shown that the preliminary administration of Zn-64 stable isotope in aspartate form led to an increase in the activity of SOD and catalase in rat hepatocytes in ethanol intoxication.

A positive effect of Zn-64 stable isotope in aspartate form on the activity of key antioxidant enzymes that was revealed may be explained, first of all, by an increase in their synthesis due to an increase in the concentrations of zinc, a necessary structural element ensuring a proper functional activity of these enzymes.

The results obtained regarding the normalizing effect of Zn-64 stable isotope in aspartate form on the prooxidant-antioxidant balance confirm a significant antioxidant potential of this isotope. Although zinc does not belong to typical antioxidants that can directly interrupt free radical reactions, it has an indirect effect on the overall prooxidant-antioxidant balance. Thus, zinc is an inhibitor of NADPH oxidases, a group of enzymes involved in the formation of the aggressive superoxide anion radical.

Directly interacting with the sulfhydryl groups of proteins, zinc protects them from oxidation by active oxygen species, induces the synthesis of metallothioneins, cysteine-rich metal-binding proteins that act as a trap for radicals, helps to inhibit the formation of reactive mixed valence metal oxides and exhibits a membrane stabilizing effect. It has been found that dietary zinc deficiency decreases concentrations of vitamin E in plasma and some other organs, which affects the general antioxidant reserve of the body.

Another mechanism for the implementation of antioxidant properties of Zn-64 stable isotope in aspartate form is associated with its ability to stabilize cell membranes, which is especially important in progressive oxidative stress. A possible cause of the membrane-protective effect of zinc may be explained by its mediating role in the induction of synthesis of metallothioneins directly involved in the detoxification of heavy metals and stabilization of membranes. Elevated levels of metallothioneins may maintain the integrity of membranes and protect cells from the action of alkylating agents.

It has been found that zinc can stabilize the cell membrane by influencing the synthesis of phospholipids (activation of PS synthase, PS decarboxylase, PEA methyltransferase and phospholipid methyltransferase with a simultaneous decrease in the activity of PHI synthetase) and their asymmetric distribution.

Thus, given the importance of controlling intensity of free radical reactions and maintaining a proper antioxidant status of the body, especially for patients with systemic chronic diseases pathogenesis of which is closely associated with the development of oxidative stress, the use of Zn-64 stable isotope in aspartate form as an additional means in the basic therapy of the disease may contribute to the improvement of an overall metabolic status.

Effects of Zn-64 Stable Isotope in Aspartate Form on Cytokine Profile, Resistin and Ghrelin Levels in Animal Models of Obesity There is no doubt that adipose tissue is not only an energy depot of the body, but also an organ that is actively involved in the regulation of metabolism through a complex of endocrine, paracrine and autocrine signals modulating responses of many tissues and organs, including the hypothalamus, hypophysis, pancreas, liver, skeletal muscles, kidneys, endothelium, the immune system, etc. Thus, adipose tissue secretes more than 50 protein factors, hormones and growth factors, including cytokines. There are pro-inflammatory cytokines, such as IL-1, IL-6, IL-8, IL-12, TNF-α, IFN-γ and anti-inflammatory cytokines, such as IL-4, IL-10, IL-13, TGF Mohamed-Ali V., Pinkney J., Coppacf S. Adipose tissue as endocrine and paracrine organ//Int J Obes Relat Meabol Disord 1998; 22: 1145-1158.

One of the consequences of excessive production of reactive oxygen species in adipocytes is the initiation of signaling cascades, leading to an increase in the production of pro-inflammatory cytokines by macrophages which infiltrate in adipose tissue increasing in its mass. The result of such disorders is the formation of systemic chronic inflammation in the body of a person that develops obesity. According to the actively discussed modern concept, it is subclinical chronic inflammation in adipose tissue that is thought to be one of the key links in the pathogenesis of obesity and obesity-related diseases. Chronic inflammation of adipose tissue is characterized by cellular infiltration, fibrosis, microcirculation changes, impaired adipokine secretion and adipose tissue metabolism disorders, as well as increased blood levels of such non-specific inflammatory markers as C-reactive protein, fibrinogen, and leukocytes Rajala M., Scherer E.//Endocrinology 2003; 144: 3765-3773.

An increase in the levels of pro-inflammatory cytokines not only in adipose tissue, but also in blood serum occurs a result of the inflammatory process in adipose tissue.

Cytokines, as endogenous biologically active mediators that regulate intercellular and intersystem interactions, have an effect on the survival of cells by regulating their growth, differentiation, functional activity, and apoptosis. They ensure coordination of actions of the immune, endocrine and nervous systems under physiological conditions and in response to pathological effects. It was previously believed that cytokines were produced by lymphocytes, monocytes and tissue macrophages. However, the results from recent research show that, in obesity, as in any inflammatory process, infiltration of neutrophils, T-lymphocytes, and then resident macrophages into adipose tissue occurs at an early stage, which determines the initial mechanisms of inflammation. It has been shown that macrophages contribute to hypertrophy of adipocytes, which is accompanied by an increase in their functional activity and increased synthesis of cytokines and leads to further intensification of the inflammatory response. Hypertrophied adipocytes intensely secrete chemokines and their receptors, which stimulate the influx of new neutrophils, macrophages and lymphocytes, thus contributing to a further increase in adipocyte hypertrophy, preservation and intensification of the inflammatory response. Adipocytes increase the secretion of cytokines by macrophages, which in turn act on adipocytes, causing hypertrophy and activation of adipose tissue cells. It has been found that hypertrophied adipocytes, like lymphocytes and macrophages, produce cytokines and activate the complement, triggering a chain of inflammatory processes. As a result, the inflammation becomes steady and systemic. In addition, lipid peroxidation products, such as trans-4-oxy-2-nonenal and malonic dialdehyde, are chemoattractants for monocytes and macrophages. Strengthening of the processes of lipid peroxidation in accumulated adipose tissue contributes to the attraction and infiltration of macrophages into adipose tissue in obesity, thus actively contributing to the launch of inflammation reactions.

Consequently, an increasing adipose tissue mass is a constant source of pro-inflammatory cytokines synthesized both by adipocytes and macrophages incorporated into adipose tissue, which leads to the formation of a chronic inflammatory process and maintenance of inflammation in the body. Its low intensity does not give direct clinical symptoms, but at the same time, this process is systemic in nature, which means that it affects a wide range of organs and tissues causing changes in their metabolism and impairing their function and immune system reactions.

Given the above, the next phase of the study was to find out whether the administration of Zn-64 stable isotope in aspartate form has an effect on the cytokine profile in obese animals. For this purpose, concentrations of the main pro-inflammatory (IL-1, IL-6, IL-12, IFN-$\gamma$) and anti-inflammatory (IL-4, IL-10, TGF) cytokines in adipose tissue and serum of experimental animals were determined, which allowed us to make a conclusion about the intensity of the inflammatory process in adipose tissue and assess whether such inflammatory process is systemic.

According to the obtained results, the development of obesity was accompanied by an increase in the levels of all analyzed pro-inflammatory cytokines (Table 17) in the adipose tissue of animals fed a high-fat diet, which indicates activation of the inflammatory process.

In turn, a prolonged inflammatory process may lead to the development of various complications and be a risk factor for insulin resistance and diabetes. Cytokines are not only able to reduce sensitivity of cells to insulin action, but also intensify inflammatory processes and increase accumulation of inflammatory intermediates, causing tissue damage and organ dysfunction J. Hirosumi et al.//Nature.-2002.-Vol. 420, No 6913.-P. 333-336. C. Jiang, W. Wang, J. Tang.// Journal of Endocrinological Investigation.-2013.-Vol. 36, No 11.-P. 986-992.

TABLE 17

Cytokine profile in the adipose tissue of animals from experimental groups (M ± m, n = 10)

| | Levels, RU/mg protein | | | | | | |
|---|---|---|---|---|---|---|---|
| | Pro- inflammatory cytokines | | | | Anti-inflammatory cytokines | | |
| Groups | IL-1 | IL-6 | IL-12 | IFN-$\gamma$ | IL-4 | IL-10 | TGF |
| C | 5.6 ± 1.3 | 5.9 ± 0.7 | 1.2 ± 0.03 | 4.7 ± 1.2 | 4.8 ± 0.5 | 4.7 ± 0.7 | 4.5 ± 0.9 |
| C + zinc | 4.9 ± 1.7 | 5.4 ± 0.3 | 1.0 ± 0.03 | 5.0 ± 0.8 | 5.0 ± 0.4 | 4.9 ± 0.2 | 5.1 ± 0.6 |
| DIO | 9.8 ± 2.8* | 8.9 ± 0.7* | 2.87 ± 0.08* | 7.6 ± 1.2* | 3.9 ± 0.2* | 3.1 ± 0.6* | 3.1 ± 0.1* |
| DIO + zinc | 5.8 ± 1.8# | 6.1 ± 0.7# | 1.99 ± 0.01# | 4.9 ± 0.8# | 5.1 ± 1.2# | 5.8 ± 0.8# | 5.2 ± 0.9# |

*- the difference is significant versus the control group of animals; #- the difference is significant versus the group of animal models of obesity
Note: C - control; C + zinc - control on the background of administration of Zn-64 stable isotope in aspartate form; DIO - diet induced obesity; DIO + zinc - diet induced obesity on the background of administration of Zn-64 stable isotope in aspartate form.

It has been proven that high levels of pro-inflammatory cytokines, including those mentioned above, can provoke apoptosis of $\beta$-cells. High concentrations of IL-12, the expression of which is activated by IFN-$\gamma$, lead to infiltration of CD8+lymphocytes in the pancreas and the development of acute pancreatitis. IL-1$\beta$, via binding to specific receptors on the surface of these cells, causes activation of NF-$\kappa$B-mediated apoptosis, which leads to DNA fragmentation and loss of functional activity of cells. In addition, IL-1$\beta$ may also be regarded as one of the factors contributing to the development of resistance of peripheral tissues to insulin. IL-1$\beta$ has been shown to activate I$\kappa$B kinase-$\beta$ which has an effect on insulin signaling by phosphorylating a serine residue in the insulin receptor substrate (IRS)-1. In addition, IL-1β is able to increase resistance to the action of insulin indirectly, by activating lipogenesis in the liver and contributing to an increase in the levels of triglycerides and free fatty acids in adipocytes.

It has been shown that IL-6 is accumulated in direct proportion to an increase in the adipose tissue mass in peripheral blood. Adipocytes are the second largest source of IL-6 after the immune system: 35% of circulating IL-6 is synthesized by adipose cells. Its concentration in the blood is directly proportional to the body mass index and is increased in obesity. At the same time, a decrease in body weight is accompanied by a decrease in the blood levels of IL-6. When in excess, IL-6 exacerbates insulin resistance by suppressing synthesis of one of the insulin receptor subunits. By activating lipolysis in visceral adipose tissue, IL-6 contributes to the progressive development of fatty hepatosis and systemic atherosclerosis. In addition, IL-6 induces increased production of C-reactive protein (CRP), another factor associated with obesity V. Rotter et al.//the Journal of Biological Chemistry.-2003.-No 278.—P. 45777-45784. Fantuzzi G./Journal of Allergy and Clinical Immunology.-2005.-Vol. 115, No 5.-P. 911-919.

One of the controlling mechanisms for the levels and, accordingly, the biological effects of pro-inflammatory cytokines, is implemented by a group of anti-inflammatory cytokines. These cytokines are able to inhibit the synthesis of pro-inflammatory cytokines by affecting transcription of specific genes, induce the synthesis of receptor antagonists of interleukins RAIL, enhance the production of soluble receptors and reduce the density of pro-inflammatory receptors on cells. Therefore, to clarify possible mechanisms of the effects of Zn-64 stable isotope in aspartate form on the profile of pro-inflammatory cytokines, the levels of IL-4, IL-10, and TGF were determined.

Detected changes in the levels of pro-inflammatory cytokines occurred against the background of a slight decrease in the levels of anti-inflammatory cytokines in obese animals. At the same time, in animals treated with Zn-64 stable isotope in aspartate form, the levels of anti-inflammatory cytokines were not only higher than in the untreated animal models of obesity, but also higher than in the animals from the control group.

It should be emphasized that the absence of changes in the animals from the control group treated with the test substance suggests that a long-time use of Zn-64 stable isotope in aspartate form is safe and it is able to show a therapeutic effect only with the development of pathological conditions.

As mentioned above, the pathogenesis of obesity is accompanied by a systemic chronic inflammatory process, the intensity of which can be assessed by the serum levels of pro- and anti-inflammatory cytokines.

Analysis of the cytokine profile in the serum of animals having obesity (Table 18) showed an increase in the levels of pro-inflammatory cytokines, more pronounced compared with the data obtained from adipose tissue. No statistically significant changes in the levels of anti-inflammatory cytokine IL-4 were found. A slight increase in the serum levels of IL-10 in obese animals can be regarded as a certain compensatory response of the body to a metabolic disorder.

In animals treated with Zn-64 stable isotope in aspartate form, there was a decrease in the levels of pro-inflammatory cytokines against the background of an increase in the levels of anti-inflammatory cytokines, which were even higher than in the animals from the control group.

TABLE 18

Cytokine profile in the serum of animals from experimental groups
(M ± m, n = 10)

| | Levels, RU/mg protein | | | | | | |
|---|---|---|---|---|---|---|---|
| | Pro-inflammatory cytokines | | | | Pro- inflammatory cytokines | | |
| Groups | IL-1 | IL-6 | IL-12 | IFN-γ | IL-4 | IL-10 | TGF |
| C | 3.4 ± 0.3 | 4.5 ± 0.3 | 0.5 ± 0.05 | 3.6 ± 0.8 | 5.1 ± 0.2 | 3.9 ± 0.4 | 3.8 ± 0.8 |
| C + zinc | 3.5 ± 0.7 | 4.3 ± 0.2 | 0.3 ± 0.04 | 4.6 ± 0.6 | 4.6 ± 0.8 | 4.1 ± 0.5 | 4.1 ± 0.4 |
| DIO | 11.1 ± 2.0* | 7.9 ± 0.5* | 3.7 ± 0.07* | 6.5 ± 0.8* | 4.4 ± 0.9 | 4.1 ± 1.5 | 3.5 ± 1.3 |
| DIO + Zinc | 4.2 ± 0.4# | 5.1 ± 0.4# | 2.4 ± 0.06*,# | 4.1 ± 1.2 | 5.6 ± 1.6 | 6.8 ± 1.1*,# | 5.7 ± 0.3*,# |

*- the difference is significant versus the control group of animals; #- the difference is significant versus the group of animal models of obesity
Note: C - control; C + zinc - control on the background of administration of Zn-64 stable isotope in aspartate form; DIO - diet induced obesity; DIO + zinc - diet induced obesity on the background of administration of Zn-64 stable isotope in aspartate form.

One of the basic mechanisms of the effect of zinc on the cytokine profile may be its inhibition of transcription factors sensitive to oxidative stress. Zinc may also partially block genes encoding pro-inflammatory cytokines, such as IL-6 and IL-8.

A certain normalizing effect of Zn-64 stable isotope in aspartate form on the cytokine profile in animal models of obesity may serve as evidence of the possible anti-inflammatory potential of the studied test substance in obesity.

Thus, a decrease in the levels of pro-inflammatory cytokines in the serum and adipose tissue of animals treated with Zn-64 stable isotope in aspartate form may in part be due to an increase in the levels of anti-inflammatory cytokines. Taking into account the existence of a close relationship between the amount of adipose tissue and the levels of pro-inflammatory cytokines that it produces, it appears that that the revealed positive effect of Zn-64 stable isotope in aspartate form on the cytokine profile is associated primarily with its influence on body weight, and therefore on the amount adipose tissue.

In addition to cytokines, adipocytes secrete a number of biologically active substances involved in the regulation of energy metabolism. One of such substances is resistin or adipocyte-specific secretory factor (ADSF/FIZZ3). Participation of resistin in stimulation of the mechanisms of inflammation, activation of the endothelium and proliferation of vascular smooth muscle cells makes it possible to view it as a marker or even an etiological factor in the development of diseases. This adipose-derived hormone has a feedback effect on the fat metabolism: on the one hand, its concentrations increase with the differentiation of adipocytes, and on the other hand, resistin suppresses adipogenesis. Resistin, as one of the causes of insulin resistance, can be a link between obesity and the development of diabetes. According to the literature data, resistin levels may be used as a predictor of susceptibility to type II diabetes and obesity. It has been shown that resistin is capable of reducing sensitivity of peripheral tissues to the action of insulin, thus stimulating the development of insulin resistance. Resistin activates NF-κB-dependent expression and release of pro-inflammatory cytokines and adhesion molecules, including TNF-α and IL-6 Fantuzzi G./Journal of Allergy and Clinical Immunology. 2005.-Vol. 115, No 5.-P. 911-919. C. Jiang et al.,//Journal of Endocrinological Investigation.-2013.-Vol. 36, No 11.-P. 986-992.

Therefore, the levels of resistin in the adipose tissue and serum of animal models of obesity from all experimental groups were investigated. In accordance with the results obtained in the experiment, there was a tendency to an increase in the levels of this adipokine, more pronounced in adipose tissue (Table 19).

TABLE 19

Resistin and ghrelin levels in adipose tissue and serum of animals from experimental groups (M ± m, n = 10)

| Experimental groups | Resistin, RU/mg protein | | Ghrelin, RU/mg protein |
|---|---|---|---|
| | Adipose tissue | Serum | Serum |
| C | 0.26 ± 0.05 | 0.18 ± 0.05 | 0.019 ± 0.003 |
| C + zinc | 0.25 ± 0.05 | 0.12 ± 0.05 | 0.016 ± 0.003 |
| DIO | 0.34 ± 0.05* | 0.19 ± 0.05 | 0.027 ± 0.003* |
| DIO + zinc | 0.25 ± 0.05# | 0.16 ± 0.05 | 0.019 ± 0.003# |

*the difference is significant versus the control group of animals;
the difference is significant versus the group of animal models of obesity
Note:
C—control;
C + zinc—control on the background of administration of Zn-64 stable isotope in aspartate form;
DIO—diet induced obesity;
DIO + zinc—diet induced obesity on the background of administration of Zn-64 stable isotope in aspartate form.

Taking into account that resistin is a promoter of the maturation of fat cells and acts as an autocrine regulator of the formation of adiabatic factors in adipose tissue, even a slight increase in the levels of this adipokine will contribute to the growth of adipose tissue and progression of obesity-associated metabolic disorders.

The levels of resistin in animal models of obesity injected with Zn-64 stable isotope in aspartate form were within the control values.

Since resistin is mainly secreted by preadipocytes and, to a lesser extent, by mature adipocytes of visceral adipose tissue, the positive effect of Zn-64 stable isotope in aspartate form can be explained by its ability to have an effect on the body weight of animals, and hence the accumulation of fat mass in animals maintained on a high-fat diet.

Another factor directly involved in the regulation of appetite is ghrelin, a lipophilic hormone secreted mainly by P/D1 cells lining the fundus of the stomach, and, to a lesser extent, by other organs, such as the hypothalamus, hypophysis, gonads and ε-cells of the islets of Langerhans. This peptide plays an important role in the regulation of hunger and energy metabolism, stimulating food intake and provoking the development of obesity. Ghrelin receptors are localized in the same hypothalamic structures as the leptin receptor, Ob-Rb, and in the arcuate and ventromedial nuclei. Its high levels may contribute to long-term weight gain. When the threshold of ghrelin level in the body is lowered, appetite decreases F. Ferrini et al., II Current Neuropharmacology.-2009.-Vol. 7, No 1.-P. 37-49. J. Camiña et al.,// Endocrine.—2003.-Vol. 22, No 1.-P. 5-12.

Studies conducted over the past few years have revealed the importance of ghrelin in the regulation of energy balance in the body through the influence of this hormone on the hypothalamus with the involvement of neuropeptide Y and the endocanabinoid system.

Ghrelin expression is enhanced in response to hypoglycemia and is inhibited during hyperglycemia. This may indicate that ghrelin combines the body's metabolic and hormonal responses to fasting, with the involvement of insulin and the mechanisms that maintain a proper serum glucose concentration. Ghrelin has orexigenic, adipogenic and somatotropic properties and acts as a leptin antagonist, increasing the need for food. It has been shown that active immunization against ghrelin causes weight loss. The orexigenic effect of ghrelin consists in its ability to increase neuropeptide-Y neuronal activity and inhibit proopiomelanocortin neurons.

Ghrelin receptors are located both in the central nervous system (hypophysis, hypothalamus) and in other organs (pancreas, intestine, stomach). This peptide plays an important role in the regulation of hunger and energy metabolism, stimulating food intake and provoking the development of obesity. Its levels increase in fasting, weight loss, calorific food intake and hypoglycemia. Elevated plasma levels of ghrelin after weight loss caused by diet are consistent with the hypothesis that ghrelin plays a role in the long-term regulation of body weight. The levels of ghrelin are reduced in people with obesity, type 2 diabetes and hypertension.

Given a close relationship between the impaired energy homeostasis and the development of obesity, the serum levels of ghrelin in animal models of obesity treated and untreated with Zn-64 stable isotope in aspartate form were analyzed.

The data show (FIG. 16) that the development of obesity was accompanied by a decrease in the levels of this hormone, and the administration of Zn-64 stable isotope in aspartate form to animals in the control group also caused a decrease in its serum levels. In general, such data are consistent with information provided in the literature, because it is known that the levels of circulating ghrelin inversely correlate with a positive energy balance, total body weight and adipose tissue mass, adipocyte size and leptin levels. For example, the levels of ghrelin in patients with anorexia are higher than in patients that develop obesity. In animal models of obesity injected with the test substance, the levels of ghrelin were similar to those determined in animals from the control group M. Kojima, K. Kangawa.// Physiological Reviews.-2005—Vol. 85, No 2.-P. 495-522.

Thus, the data suggest that Zn-64 stable isotope in aspartate form has a normalizing effect on the functional status of adipocytes, which may result in the restoration of cytokine balance to the physiologically normal state.

Levels of Divalent Metal Ions in the Organs of Animal Models of Obesity

Participation of zinc in physiological and pathophysiological processes depends largely on its levels in the body. Zinc is found in all cells and organs, but its concentrations in one or another organ vary considerably and depend on the specific activity of the organ. Zinc reserves in the human body are quite small and amount to about 1.5 to 3 g. This figure depends on many factors: the age and sex of a person, the condition of gastrointestinal mucosa, associated diseases, pregnancy, etc. Zinc is found in almost all tissues. About 62-63% of zinc reserves are in skeletal muscles. According to the data provided by a number of researchers, zinc is distributed in the human body as follows (μg/g): skin, adrenal glands—6, ovaries—12, brain—13, lymph nodes—14, GI tract—21, heart—27, kidneys—37, liver—38, muscles—48, bones—66, prostate gland—87, sperm—125. Whole blood contains about 2.5 to 5.3 μg/ml of zinc. There is less zinc in plasma (0.7 to 1.2 μg/ml, which is about 0.2 to 1% of the total amount of zinc in the body). The levels of zinc in blood serum are slightly higher (1.1 to 1.3 μg/ml) than in plasma due to the destruction of red blood cells.

The levels of zinc and some divalent metals (copper and manganese) were determined in skeletal muscles, kidneys and liver of animals having obesity, as well as the effects of Zn-64 stable isotope in aspartate form on the levels of these metals.

The choice of copper and manganese for analysis is explained by their exceptional importance and involvement in key metabolic processes. In addition, the studied metals have an effect on the digestibility and bioavailability of each other, so an abnormal level of one of them is often the result or cause of changes in the levels of the other metals mentioned above. Most often they compete with each other. Thus, for example, iron present in food in large amounts reduces the absorption of zinc by about 2-fold. The presence of copper also reduces the absorption of zinc in the gastrointestinal tract due to its competitive association with transport metalloenzymes.

TABLE 20

Levels of divalent metal ions in the muscles, kidneys and liver of animals from experimental groups (M ± m, n = 10)
Levels, μg/ tissue

|  | Zinc | Manganese | Copper |
|---|---|---|---|
| Muscles | | | |
| C | 7.63 ± 0.66 | — | 0.72 ± 0.05 |
| DIO | 6.82 ± 0.63 | — | 1.06 ± 0.12* |
| DIO + zinc | 9.10 ± 0.42*,# | — | 0.72 ± 0.15# |
| Kidneys | | | |
| C | 18.97 ± 0.52 | 0.75 ± 0.02 | 4.74 ± 0.49 |
| DIO | 21.73 ± 1.02* | 0.63 ± 0.05* | 4.41 ± 0.51 |
| DIO + zinc | 20.28 ± 1.75 | 0.64 ± 0.03* | 4.94 ± 0.82 |
| Liver | | | |
| C | 27.64 ± 1.47 | 2.21 ± 0.24 | 3.99 ± 0.21 |
| DIO | 21.75 ± 1.12* | 1.58 ± 0.12* | 2.56 ± 0.11* |
| DIO + zinc | 31.43 ± 1.78*,# | 1.94 ± 0.12# | 3.93 ± 0.09# |

*the difference is significant versus the control group of animals;
the difference is significant versus the group of animal models of obesity
Note:
C—control;
C + zinc—control on the background of administration of Zn-64 stable isotope in aspartate form;
DIO—diet induced obesity;
DIO + zinc—diet induced obesity on the background of administration of Zn-64 stable isotope in aspartate form.

Copper belongs among the essential trace elements. The body of an adult contains about 110-150 mg of copper. Half of this amount is in the muscles. Smaller reserves of copper are concentrated in the liver, the gray matter in the brain hemispheres and in the bone marrow. This important trace element is found in enzymes and proteins (mainly ceruloplasmin). The latter is a metalloenzyme that catalyzes oxidation of a number of biologically active substances and ensures the delivery of copper to various tissues and organs. It is known that copper is a specific activator of cytochrome oxidase, tyrosinase and copper oxidase. Copper activates arginase and aminopeptidase, enzymes of protein metabolism, which enhance the synthesis of nucleic acids necessary for healing processes. This biotic is involved in the processes of blood formation, hemoglobin synthesis, function of the cytochrome system and is part of red blood cell stroma. Copper used in microdoses increases glycogen levels in skeletal muscles and liver. It shows an insulin-like activity, accelerating the glucose oxidation and inhibiting the breakdown of glycogen. Copper strengthens the neutralizing function of the liver and normalizes mineral metabolism. Copper is part of many enzymes, it determines their function and regulates their action. It is part of all oxidases, and as such is an important element of redox reactions in the body. These enzymes are necessary for the processes of cellular respiration and protection of cells from the effects of free radicals and are involved in the synthesis of myelin, biosynthesis of connective tissue, and metabolism of glands. The antioxidant activity of copper is associated with its participation in the structural formation of superoxide dismutase.

Manganese is an essential trace element necessary to ensure a proper metabolic status of the body. Its highest levels are found in the bones, liver and gray matter in the brain hemispheres. This biotic has an insulin-like effect, reducing the blood glucose levels and increasing the synthesis of glycogen. It has been found that manganese stimulates blood formation. It has a high oxidative activity and a pronounced lipotropic (cholin-like) action. This trace element has an effect on the fat and protein metabolism and the synthesis of a number of vitamins. In addition, it is part of the most important enzymatic systems. Manganese salts weaken a hypertensive effect of adrenaline and induce a decrease in adrenaline hyperglycemia. Manganese has cholesterol-lowering and anti-sclerotic effects.

According to the results obtained (Table 20), there was a tendency towards redistribution of zinc between the organs in the development of obesity. Thus, the zinc levels increased slightly in the kidneys and decreased in the liver and muscles. An increase in the zinc levels in the muscles of animals treated with Zn-64 stable isotope in aspartate form is, on the one hand, quite natural, given that most of all zinc reserves in a normal physiological condition are located in skeletal muscles, and on the other hand, this can be considered as indirect confirmation of the absence of visible functional impairments in the processes of transportation and deposition of zinc in obese animals that were administered the test substance.

More significant is a decrease in the zinc levels in the liver of animal models of obesity. After all, the liver is the main place for the synthesis of zinc-containing proteins. Therefore, a decrease in zinc reserves in this organ will contribute to the development and progression of disorders associated with insufficiency of zinc-dependent and zinc-containing enzymes. One of the consequences of reducing zinc levels in the liver can be a decrease in the serum activity of superoxide dismutase in obese animals that was identified at the previous phase of this study.

Zinc levels in the liver of animals fed a high-fat diet and injected with Zn-64 stable isotope in aspartate form were even slightly higher than in animals from the control group, which is indicative of the restoration of zinc homeostasis.

As for copper, there was a tendency towards an increase in its levels in the muscles and a decrease in the kidneys. The most pronounced changes in the copper concentrations were observed in the liver, an organ that plays a major role in the metabolism of this trace element.

It should be emphasized that zinc is a competitor of copper in the processes of absorption in the intestines and when at high concentrations, it may cause development of copper deficiency in the body. Therefore, an absence of significant changes in the copper levels in animals treated with Zn-64 stable isotope in aspartate form indicates that the dose level of this element was selected properly.

These results suggest a positive effect of Zn-64 stable isotope in aspartate form on key systems directly involved in the development and progression of obesity.

In general, summarizing the results, Zn-64 stable isotope in aspartate form administered to animal models of obesity exhibits a complex effect that extends to a number of systems an impaired function of which may have the most serious consequences for the body.

Considering the importance of preserving zinc homeostasis to ensure a proper physiological status of all body tissues, adipose tissue in particular, it appears that the obtained data on the positive effect of Zn-64 stable isotope in aspartate form in obesity are partly associated with the restoration of zinc levels, reduced during the pathogenesis of obesity.

According to the accumulated data on the physiological role of zinc, an increase in its levels may cause a cascade of biochemical shifts, which, ultimately, determine its overall positive effect.

There are several potential mechanisms for the implementation of modulating effects of Zn-64 stable isotope in aspartate form. First of all, it is the enhancement of synthesis of zinc-dependent enzymes and transcription factors. Increasing the number of key antioxidant enzymes due to availability of zinc—a necessary structural component of these enzymes—against the background of intensification of free radical processes and the progression of oxidative stress will help to maintain an appropriate antioxidant reserve. An important fact is the ability of zinc to induce the synthesis of a number of antioxidants, anti-inflammatory cytokines and factors that are actively involved in the regulation of cellular signaling cascades and are involved in the regulation of basic processes. Thus, according to the literature data, the levels of zinc-alpha-glycoprotein (ZAG), which contributes to a decrease in fat deposits by stimulating lipolysis in adipocytes, is significantly reduced in obesity. In addition, the process of differentiation of adipocytes, brown adipose tissue in particular, is strictly determined and controlled by a group of transcription factors, many of which contain zinc.

Thus, the results of the comprehensive analysis of the effects of Zn-64 stable isotope in aspartate form on the pathogenesis of obesity show this trace element as a promising additive to be used in the development of biologically active compounds not only for the treatment of pathologies accompanied by a chronic inflammatory process, systemic depletion of the antioxidant reserve and disturbances in the function of the serotonergic system but also for the prevention of diseases associated with systemic metabolic disorders.

Conclusions

For the first time, a comprehensive study into the effects of Zn-64 stable isotope in aspartate form on the key pathogenetic links of the development and progression of obesity in diet-induced obesity models was conducted. The obtained results provide a factual basis for advisability of the use of Zn-64 stable isotope in aspartate form as an auxiliary therapeutic agent in the treatment of overweight and obese patients.

It has been shown that the administration of Zn-64 stable isotope in aspartate form to animals that were maintained on a high-fat diet is accompanied by a decrease in their body mass index and helps to reduce weight and the amount of food consumed compared to the untreated animal models of obesity.

It has been found that Zn-64 stable isotope in aspartate form has a positive effect on the lipid metabolism in the body of animals that were fed a high-fat diet.

It has been found that Zn-64 stable isotope in aspartate form has a positive effect on the morphofunctional properties of the pancreas and liver of animals that were fed a high-fat compared to the untreated animal models of obesity.

It has been found that Zn-64 stable isotope in aspartate form administered to animals fed a high-fat diet has a modulating effect on the activity of key enzymes involved in serotonin metabolism, which helps to restore the levels of central and peripheral serotonin compared to the values in the untreated animal models of obesity.

It has been shown that the administration of Zn-64 stable isotope in aspartate form contributes to the normalization of prooxidant-antioxidant homeostasis in animals that were fed a high-fat diet due to a decrease in the intensity of free radical processes (decrease in the levels of lipid peroxidation products and protein oxidative modification) against the background of activation of antioxidant defense via increased activity of antioxidant enzymes (superoxide dismutase and catalase).

The ability of Zn-64 stable isotope in aspartate form to influence a cytokine profile in the serum and adipose tissue of animals maintained on a high-fat diet, namely to reduce the levels of pro-inflammatory cytokines (IL-1, IL-6, IL-12, IFN-γ) against the background of a slight increase in the levels of anti-inflammatory cytokines (IL-4, IL-10, TGF) has been shown, which generally indicates a decrease in the intensity of systemic inflammation.

It has been found that Zn-64 stable isotope in aspartate form has no visible effects on the levels of resistin in adipose tissue and blood serum of animals having obesity, as well as on the serum levels of ghrelin.

It has been found that the administration of Zn-64 stable isotope in aspartate form causes redistribution of divalent metal ions (zinc, copper, manganese) between muscles, kidneys and liver in animal models of obesity and contributes to restoration of their physiological levels.

Example 7 Effects of Experimental Drugs on Fluctuations of Insulin Levels in the Blood of Laboratory Animals (Rats) by Intraperitoneal Administration The first group consisted of animals that were injected with saline (body weight 180-220 grams).

Number of animals: 8 (4 animals per group); 2 points of sampling—on the second day after the drug administration and on the 7th day after the last injection of saline solution (4×2=8).

The second group consisted of animals that were injected with zinc acetate with natural distribution of isotopes (body weight 180-220 grams). The current dose was calculated by zinc. Each animal was injected with 3750 μg of zinc per 1 kg of animal body weight. A comparison group for evaluating the effects of zinc on experimental animals. Zinc acetate is a standard zinc compound used in most animal experiments and diabetes experiments.

Number of animals: 8 (4 animals per group); 2 points of sampling—on the second day after the drug administration and on the 7th day after the last injection of saline solution (4×2=8).

The third group consisted of animals that were injected with zinc isotope in the form of aspartate ($Zn^{64M}$) (body weight≈180-220 grams). The current dose was calculated by zinc. Each animal was injected with 3750 μg of zinc per 1 kg of animal body weight.

Number of animals: 8 (4 animals per group); 2 points of sampling—on the second day after the drug administration and on the 7th day after the last injection of saline solution (4×2=8).

The Scheme of Experiment:

Animals are placed in cages, 4 per cage, with free access to food/water. 3 days after the animals have been in cages, they are injected with the experimental drug—natural zinc or isotopically light zinc. Administration is performed every other day, in the amount of 7 injections per animal (intraperitoneal method of drug administration). The dose of the drug injected to each animal was calculated on the basis of the ratio: 3750 μg of zinc per 1 kg of animal body weight. After the last injection, a half of the animals are maintained on hunger (for 12 hours) with free access to water. Upon expiration of this time period, the animals are taken out of the experiment. The second half of the animals continues to have free access to food/water for a further 7 days. On day 6 after the last injection, the animals are maintained on hunger (for 12 hours) with free access to water. Upon expiration of this time period, the animals are taken out of the experiment.

Research Materials

Compliance with Animal Welfare Regulations that Govern Animal Research Activities International recommendations for conducting biomedical research using animals in accordance with the General Principles of Working with Animals, approved by the First National Congress on Bioethics (Kiev, Ukraine, 2001) and agreed with the provisions of the "European Convention for the Protection of vertebrates that are used for experimental and other scientific purposes" (Strasbourg, France, 1986) were followed while working with laboratory animals. Experimental work with rats was carried out in the vivarium of the Taras Shevchenko National University of Kyiv. Studies with animals were regulated by the rules of experimental work with experimental animals, which were approved by the Scientific Council of this institution, which, in turn, were coordinated with the current legislation of Ukraine, adopted at that time.

Conditions for Research Performance in Rats

Studies were performed on white rats aged from 2 to 3 months and weighing 120-300 g. Experimental animals were kept on a standard vivarium diet with free access to water. During the experiments, the animals were kept at room temperature 19-24° C., humidity not more than 50%, in a natural day-night light mode in plastic cages. Before the experiments, animals were acclimatized in the research room for 7 days.

Preparation of Blood Serum of Rats

The rat serum was prepared from whole blood. To remove concomitant proteins and fibrinogen, the whole blood was left undisturbed at 37° C. for 30 minutes after which the samples were centrifuged at 2500 g for 15 min. The resulting supernatant (serum) was immediately separated from blood corpuscles and frozen at −20° C. for further analyses.

Preparation of Kidney and Liver Homogenates

The total kidney, liver and muscle homogenates were prepared as follows. Organ excision and homogenization were carried out at a temperature of 1-4° C. Homogenization of tissues was carried out in 50 mM Tris-HCl buffer (pH 7.4) which contained 140 mM NaCl, 1 mM EDTA. The volume of the used buffer in ml was 5 times larger than the mass of isolated organs in grams. The isolated liver was perfused with chilled saline (0.9% NaCl) via the portal vein using a syringe. The minced liver was transferred to a homogenizer with a finely ground Teflon pestle and homogenized in chilled buffer. An isolated pair of kidneys was perfused with chilled saline, released from adipose tissue and minced with scissors. The minced tissue was transferred to a homogenizer with a finely ground Teflon pestle and homogenized in chilled buffer. The total kidney and liver homogenates were centrifuged at 600 g for 15 minutes. The liquid was decanted after the mince settled down and was centrifuged again at 15,000 g for 15 minutes. These two procedures allowed us to get rid of nuclear and mitochondrial debris. Aliquots of the prepared homogenates were frozen in nitrogen (Rybalchenko V. K., Koganov M. M. Structure and function of membrane 1988.-312 pp).

1. Method for Determination of Insulin Level in Animal Serum:

Enzyme-Linked Immunosorbent Assay (Insulin levels in blood serum of rats were determined using enzyme immunoassay based on the common method used for soluble proteins. It was carried out in 96-well microplates with sorption capacity for soluble proteins [Crowther J. R. The ELISA Guidebook/J. R. Crowther.-Totowa, N.J.: Humana Press Inc., 2001.-P. 436].

The serum was prepared as a 1 to 10 dilution with 50 mM Tris-HCl buffer (pH 7.4) containing 150 mM NaCl. Samples in volume of 100 μl were incubated in microplate wells at 4° C. overnight. After incubation, the wells were washed with the buffer comprising 50 mM Tris-HCl buffer (pH 7.4) with 150 mM NaCl and 0.05% Tween 20 to remove the unbound material. Non-specific binding sites were blocked with a 5% fat-free milk blocking solution and incubated for 1 hour at 37° C. After washing, the separate wells of the microplate were loaded with primary rabbit anti-insulin antibodies and incubated for 1 hour at 37° C. After incubation, the microplate wells were washed and loaded with appropriate secondary antibodies conjugated to horseradish peroxidase and incubated for another 1 hour at 37° C. The binding of secondary antibodies was visualized by adding 100 μl of OPD solution to each well at a concentration of 0.4 mg/ml prepared in citrate buffer (pH 5.0) containing 0.013% $H_2O_2$. The optical density was measured at 492 nm. The insulin concentrations were calculated using the calibration curve generated under the given conditions and human insulin of known concentration.)

Determination of Superoxide Dismutase Activity in the Rat Liver and Serum

A method which is based on the ability of the enzyme to inhibit the process of adrenaline auto-oxidation was chosen to measure the superoxide dismutase (SOD, EC 1.15.1.1) activity is used.

10 μl aliquots of the test samples (liver and kidney homogenates) were placed into microplate wells. 200 μl of 0.2 M bicarbonate buffer (pH 10.65) was added to each well. The reaction was started by adding 10 μl of a 0.1% solution of adrenaline to each well. No source of enzymes was added to the blank sample. The optical density was measured using a microplate reader at a wavelength of 347 nm at the 4th and 8th minute after adrenaline was added.

A classical method of measuring enzymatic activity based on the accumulated quantity of the product or decrease in the amount of substrate is not applicable to SOD because it is impossible to construct a calibration curve for the reaction product which is the oxidized product of adrenaline. The activity of this enzyme was expressed in conventional units/min*mg of protein which were calculated using the following formula:

$$A = \frac{X * 50}{Y * 4 * 100 * a},$$

where X is the optical density of blank samples without test sample equal to the difference between the optical density of the blank sample at minute 8 and optical density of the same at minute 4; Y is the optical density of blank samples with the test sample equal to the difference between the optical density of the blank sample at minute 8 and optical density of the same at minute 4; a is an amount of protein in the blank sample, mg; 4 is incubation period between the determination of extinction, 4 min; 50/100 is conversion into conventional units (Sirota T. V. Novel approach to the study of adrenaline auto-oxidation and its use for the measurements of superoxide dismutase activity// Vopr Med Khim—1999.-45 (3).-P. 263-272).

Determination of Glucose Tolerance

Animals that had access only to water 16 hours before the start of the experiment were used in the glucose tolerance test. Rats were anesthetized with intraperitoneal injection of sodium thiopental at a dose of 40 mg/kg. 5 animals were used within the same experimental group. Basal levels of glycaemia were determined in rats, after which the animals were fed 2 ml of aqueous glucose solution at a dose of 3 g/kg. The concentration of glucose was determined 60 minutes after the start of the experiment. Blood collection was performed via the tail vein (Gorbulinska O. V. Sugar-lowering effects of water extracts of yakon (Smallanthus sonchifolius poepp. & endl.)/O. V. Gorbulinska, M. R. Khokhla, L. T. Mishenko et. al.//Biological Studios—2014.-8 (2).-P. 57-64.) Results see FIG. 16A-FIG. 16E.

According to all the data analyzed, there are no reliable differences between the control groups (rats injected with saline) and the groups where rats were administered zinc. This may be due to two factors—either zinc solution was administered incorrectly (intraperitoneally instead of orally) or, since intact rats were used, they may have compensatory mechanisms which, in the event of an increase in the amount of zinc in the body, do not allow the shift of the balance of the insular system towards hyperproduction of insulin, as this may result in hypoglycemia with all that it entails.

At the same time, a significant increase in the body weight of rats is observed in the group that was administered an isotope of zinc. This is a positive result, since people with type 1 diabetes often have a decrease in body weight. The obtained data may indicate that the isotope of zinc may have a positive effect on the dynamics of weight gain.

Analysis of insulin levels in the serum of the experimental groups of animals showed the following results: no significant changes in the insulin levels during the entire experiment were noted in the control group of animals. In the group of animals injected with zinc acetate, a significant increase is observed in the insulin levels on the first day after the drug withdrawal, and then a drop in the insulin levels to the value of those of intact/control animals. A reverse situation is observed in the group which was given injections of zinc isotope. On the first day after the drug withdrawal, the insulin levels were slightly higher than in the group of intact animals, and at day 7 after the withdrawal a significant increase in the insulin levels in this group of animals was observed. FIG. 17.

The results show that zinc isotope, as compared with zinc acetate, either has a more prolonged effect on insulin levels in blood serum or is more slowly released from the sites of deposition, and this also causes a slower effect of increasing insulin levels.

Analysis of the superoxide dismutase activity showed no significant changes in its activity in serum in all experimental groups of animals. This may be due either to the lack of effect of the injected zinc preparations on the activity of this enzyme or (which is most likely) to incorrect administration of zinc preparations. FIG. 18A-FIG. 18B.

Microscopic study of islets of Langerhans has shown a positive dynamics after administration of zinc isotope—a significant increase in the islet area compared to the control group and the group injected with zinc acetate. FIG. 19.

The results obtained correlate with the results from the analysis of insulin levels in serum of the laboratory animals. Microscopic results indicate that the administration of zinc preparations, zinc isotope in particular, leads to an increase in the area of pancreatic islets, which in its turn may indicate the possibility of increasing insulin production by these islets. This is a move in the right direction, since the development of type I diabetes is associated with a significant insulin deficiency due to problems with its synthesis by these islets. FIG. 20A-FIG. 20F.

TABLE 21

Glucose tolerance test (night on hunger, glucose at a dose of 3 g/kg of body weight in a volume of 2 ml)

| | Body weight, g | 0 min (1 h after effector administration) | 60 min (1 h after glucose administration) |
|---|---|---|---|
| Control (2 ml saline) | | | |
| 1 | 190 | 4.7 | 7.9 |
| 2 | 196 | 5.8 | 8 |
| 3 | 217 | 5.1 | 8 |
| 4 | 206 | 5.4 | 8.2 |
| 5 | 190 | 4.8 | 7.6 |
| Zn isotope (dose: 5 mg/kg in a volume of 2 ml) | | | |
| 1 | 195 | 4.5 | 6 |
| 2 | 178 | 4.8 | 6.3 |
| 3 | 187 | 4.5 | 6.5 |
| 4 | 186 | 4.7 | 6.6 |
| 5 | 184 | 4.8 | 6.5 |

A glucose tolerance test was performed to determine a potential effect of zinc isotope on the dynamics of glucose concentration in the blood flow. Experimental procedure: laboratory animals are given intragastric injections of either normal saline solution or zinc in saline solution (5 mg/kg) in a volume of 2 ml. After that, 60 minutes after the aforementioned injections, the basal level of glucose is measured and a glucose solution is injected in an amount of 3 g/kg in a volume of 2 ml using the same route of administration. The blood glucose levels are measured again 60 minutes after injecting the glucose solution. The difference in the drop in glucose levels indicates a positive effect of the injected effector on the dynamics of glucose levels in the bloodstream.

The glucose tolerance test has shown a drop in glucose concentration after administering zinc isotope as compared to the control group. This may indicate the influence of administration of zinc isotope on the insulin levels in the bloodstream, which in its turn results in triggering mechanisms associated with clearing the blood from glucose. Given that insulin is a zinc-dependent protein, it can be assumed that the administration of zinc causes either an increase in the activity of this protein relative to its receptor in tissues or an increase in the amount of this hormone in the bloodstream.

Analysis of accumulation of metals in the liver tissues (zinc, manganese and copper) has shown that only zinc level significantly increases in both groups of animals that received zinc preparations both at day 1 after the drug withdrawal and at day 7 after the withdrawal. This indicates that zinc administered to the animals is accumulated and its removal does not increase. All other analyzed metals are within the limits of their concentrations observed in the control group of animals. FIG. 21A-FIG. 21C.

Analysis of accumulation of metals in the kidney tissues (zinc, manganese and copper) has shown that only zinc level significantly increases in both groups of animals that received zinc preparations both at day 1 after the drug withdrawal and at day 7 after the withdrawal. This indicates that zinc administered to the animals is accumulated and its removal does not increase. All other analyzed metals are within the limits of their concentrations observed in the control group of animals. FIG. 22A-FIG. 22C. FIG. 23A-FIG. 23F.

Research Report on the Potential Effects of Test Substance ($Zn^{64}$ Aspartate) on Type I Diabetes in Experimental Animals (Rats)

Oral Administration

The First Group—

Control. Weight of animals≈140-150 grams (initial body weight of animal).

Number of animals: 5 (males). All 5 animals were group-housed in one cage and provided ad libitum access to food and water. At the start of the experiment, each animal was given a single injection of 10 mM citrate buffer (pH 4.5) intraperitoneally. 24 hours later, 7 doses of the test substance were administered to the animals orally. Frequency of administration—every other day. Dose of administration—800 µg of zinc per animal.

After the last administration, the animals were fasted for 12 hours with ad libitum access to water. Upon expiration of this time period, the animals were taken out of the experiment The Second Group—

Diabetes. Weight of animals 140-150 grams (initial body weight of animal).

Number of animals: 10 (males). Animals were housed in cages, 4 per cage, and provided ad libitum access to food and water. To induce diabetes in animals, each animal was given a single injection of streptozotocin solution at a dose of 6 mg per 100 g of animal weight dissolved in 10 mM citrate buffer (pH 4.5) intraperitoneally. Dose of administration—800 µg of zinc per animal. The fasted animals were tested for sufficient levels of glycemia two days after induction of diabetes. Rats with blood glucose concentrations within the range >20 mmol/l were used in the experiments.

The Third Group—

Diabetes+zinc: Weight of animals 140-150 grams (initial body weight of animal).

Number of animals: 10 (males). Animals were housed in cages, 4 per cage, and provided ad libitum access to food and water. To induce diabetes in animals, each animal was given a single injection of streptozotocin solution at a dose of 6 mg per 100 g of animal weight dissolved in 10 mM citrate buffer (pH 4.5) intraperitoneally. The fasted animals were tested for sufficient levels of glycemia two days after induction of diabetes. Rats with blood glucose concentrations within the range >20 mmol/l were used in the experiments.

24 hours later, 7 doses of the test substance were administered to the animals orally. Frequency of administration—every other day.

Dose of administration—800 µg of zinc per animal.

Research Materials

Compliance with Animal Welfare Regulations that Govern Animal Research Activities The laboratory animals used in the experiments were maintained in compliance with international standards and recommendations on clinical and biological research involving animals and in compliance with Basic Principles of Humane Animal Handling approved by the $1^{st}$ National Congress in Bioethics (Kyiv, Ukraine, 2001), which are in line with the standards of the European Convention for the Protection of Vertebrate Animals used for Experimental and other Scientific Purposes (Strasbourg, 18 Mar. 1986). All experiments involving animals were performed in the vivarium of Taras Shevchenko National University of Kyiv according to animal testing regulations developed in compliance with applicable laws of Ukraine and approved by the Academic Board of the said institution.

Conditions of Maintenance of Laboratory Animals

White rats 2 to 3 months old weighing 120-130 g were used in the experiments. The laboratory animals were fed standard vivarium diet and had free access to water. During the experiments, the animals were housed in plastic cages and environmental controls were set to maintain conditions of 19-24° C. and 50% relative humidity with a 12-h light-dark cycle. All animals were allowed to acclimatize to their environment for 7 days before the onset of the experiments.

Determination of Glucose Concentration in Serum of Rats

The glucose concentration in whole blood was measured by the glucose oxidase method using a GlucoDr Auto AGM-4000 blood glucose meter (Allmedicus Co., Ltd., Korea). All procedures were performed according to the manufacturer's instructions Induction of Type I Experimental Diabetes in Rats Type I experimental diabetes was induced by a single intraperitoneal injection of streptozotocin solution at a dose of 6 mg per 100 g of animal weight dissolved in 10 mM citrate buffer (pH 4.5). The rats of the control group were administered 10 mM citrate buffer (pH 4.5) by the aforementioned method. The whole blood glucose concentrations were measured two days after induction of diabetes in rats. Animals were considered diabetic at blood glucose level reaching 22-32 mmol/L (M. Zafar, S. Naqvi//Int. J. Morphol.-2010.-Vol. 28, No 1.-P. 135-142.).

Preparation of Blood Serum of Rats

The rat serum was prepared from whole blood. To remove concomitant proteins and fibrinogen, the whole blood was left undisturbed at 37° C. for 30 minutes after which the samples were centrifuged at 2500 g for 15 min. The resulting supernatant (serum) was immediately separated from blood corpuscles and frozen at −20° C. for further analyses.

Determination of Glycated Hemoglobin in the Blood of Rats

The levels of glycated hemoglobin in whole blood of rats was measured spectrophotometrically in accordance with the established procedure. The assay was performed using a standard assay kit manufactured by Lachema (Czech Republic).

The method for glycated hemoglobin measurement is based on the fact that the stable form of glycohemoglobin (HbA1c) contains 1-deoxy-1-(N-valyl) fructose, which is dehydrated with phosphoric acid to form a colored complex with an absorption spectrum at 433 nm. Neither the labile form of glycohemoglobin nor fetal hemoglobin interferes with the determination of glycated hemoglobin.

Total hemoglobin was measured spectrophotometrically. 20 µl of whole blood was mixed with 5 ml of the transforming solution. The absorbance was read at a wavelength of 540 nm against the transforming solution. The total hemoglobin fraction was calculated according to the manufacturer's recommendations using the following formula:

$$Hb = \frac{A * 367.7}{4.92}$$

where Hb is total hemoglobin, A is optical density of the test sample. The amount of total hemoglobin is expressed in g/L.

Hemolysate was prepared by adding an anticoagulant, 3.8% solution of Na citrate diluted at 1:10, to freshly collected blood. 1 ml of stabilized blood was collected and centrifuged at 1000 g for 10 min to remove plasma. 3 ml of saline was added to the obtained erythrocyte sediment, the mixture was gently stirred and centrifuged again, as described above. 3 ml of distilled water was added to the sediment and the well-mixed mixture was allowed to stand at room temperature for 10 minutes. After another centrifugation, 1.5 ml of supernatant (hemolysate) was separated and mixed with 0.25 ml of 85% phosphate acid solution. The test tubes were closed with rubber stoppers and heated in a boiling water bath for 30 minutes. At dehydration, the tubes were cooled in running water for 10 minutes. 0.5 ml of a 2.45 M solution of trichloroacetic acid was added to each tube. The contents of the tubes were shaken and centrifuged at 1000 g for 20 minutes. To 1 ml aliquot of supernatant pipetted into another set of dry tubes, 2.5 µM of thiobarbituric acid solution was added. The contents of the tubes were thoroughly mixed and incubated at 37° C. for 40 min. The same manipulations were carried out for control samples, water was added to C1 instead of acid, and acid and a mixture of hemolysates from different samples were added to C2. The optical density of the samples was measured on a spectrophotometer at a wavelength of 443 nm against distilled water.

Concentration of glycohemoglobin was calculated using the following formula:

$$HbA1c = \frac{A_1 - (A_2 - A_3)}{Hb * K},$$

where $A_1$ is the optical density of the test sample, A2 is the optical density of the control sample for reagents, A3 is the optical density of the positive control sample, K is the tangent of an angle calculated in accordance with the fructose calibration curve, Hb is the total hemoglobin content.

Concentration of glycohemoglobin was expressed as µmols of fructose per g of hemoglobin (Glycated hemoglobin/Assay kit//Pliva-lachema diagnostica.-2008.—10003258.).

Determination of Insulin Levels in Rat Serum

Insulin levels in blood serum of rats were determined using enzyme immunoassay based on the common method used for soluble proteins. It was carried out in 96-well microplates with sorption capacity for soluble proteins.

The serum was prepared as a 1 to 10 dilution with 50 mM Tris-HCl buffer (pH 7.4) containing 150 mM NaCl. Samples in volume of 100 µl were incubated in microplate wells at 4° C. overnight. After incubation, the wells were washed with the buffer comprising 50 mM Tris-HCl buffer (pH 7.4) with 150 mM NaCl and 0.05% Tween 20 to remove the unbound material. Non-specific binding sites were blocked with a 5% fat-free milk blocking solution and incubated for 1 hour at 37° C. After washing, the separate wells of the microplate were loaded with primary rabbit anti-insulin antibodies and incubated for 1 hour at 37° C. After incubation, the microplate wells were washed and loaded with appropriate secondary antibodies conjugated to horseradish peroxidase and incubated for another 1 hour at 37° C. The binding of secondary antibodies was visualized by adding 100 µl of OPD solution to each well at a concentration of 0.4 mg/ml prepared in citrate buffer (pH 5.0) containing 0.013% $H_2O_2$. The peroxidase reaction was stopped after 10 min by adding 100 µl of 1 M $H_2SO_4$. The optical density was measured at 492 nm. Concentrations of insulin, cytokines and IgG were expressed in relative units related to the total protein concentrations in serum determined using the Bradford protein assay.

Determination of Protein Concentrations

The protein concentrations were measured using the Bradford protein assay, which is based on an absorbance shift of the dye Coomassie Brilliant Blue G-250.

To measure the protein concentration, 10 µl of 30% NaOH, 70 µl of distilled water, and 2 ml of Bradford reagent were added to each sample. To prepare 100 ml of Bradford reagent, 6 ml of stock solution, 3 ml of 95% ethanol, 6 ml of 88% $H_3PO_4$ and 35 mg of Coomassie Brilliant Blue dye were mixed and the resulting mixture was adjusted to the volume of 100 ml with distilled water. The stock solution contained 10 ml of 95% ethanol, 20 ml of 88% $H_3PO_4$ and 35 mg of Coomassie Brilliant Blue.

The absorbance, which was visible in 2-5 min, was then measured spectrophotometrically at 595 nm against a control sample that contained 20 µl of distilled water instead of biomaterial. The protein concentration in each test sample was determined using a calibration curve and expressed in mg/ml.

Statistical Processing of the Results

Statistical processing of the obtained results was carried out using the methods of variation statistics and correlation analysis using Origin Pro 7.0 and SPSS 16 software. Key statistical values were obtained by calculations of the mean (M) and the standard error of the mean (m). The difference between variables was evaluated using a parametric statistical technique (ANOVA). Student's t-test was used to evaluate the statistical significance of differences between two samples. The difference was considered statistically significant when $p<0.05$.

Results

The study examining the potential effects of $Zn^{64}$ Aspartate on the development of type I diabetes in the experimental group of rats showed the following results (Table 22). It was demonstrated that the main parameters that characterize the development of type I diabetes, namely concentrations of glucose, glycated hemoglobin and insulin, improved after administration of the test substance. A significant decrease in glucose levels (by 26%) and glycated hemoglobin (by 30%) was registered. It was also found, that the serum insulin levels increased by 13%. The obtained results may indicate that this test substance has a positive effect on the course of type I diabetes and may be used as a prophylactic agent to reduce the toxic effects of increased glucose levels in the bloodstream during the development of this pathology.

TABLE 22

Values confirming the diagnosis of type I diabetes in streptozotocin-induced type I diabetes rat models

|  | Glucose, mM | Glycated hemoglobin, μmol fructose/g Hb | Insulin, RU/mg protein |
| --- | --- | --- | --- |
| Control (n = 5) | 4.9 ± 0.1 | 0.34 ± 0.03 | 23 ± 1 |
| Diabetes (n = 10) | 27 ± 3* | 0.72 ± 0.1* | 15 ± 3* |
| Diabetes + 64Zn Aspartate (n = 10) | 20 ± 3 | 0.51 ± 0.05*# | 17 ± 2* |

*$p < 0.05$ versus the control group
$p < 0.05$ versus type I diabetes group

Cytokines are endogenous, biologically active polypeptide mediators represented by a large heterogeneous group of low-molecular, non-specific antigens, and glycoproteins that are produced in response to an external extracellular stimulus and are involved in formation and regulation of specific immune responses in the body through the interaction between non-specific protective reactions and specific immunity. Pro-inflammatory cytokines, such as IL-1, IL-6, IL-8, IL-12, TNF-α, IFN-γ, take part in the launch of specific immune responses, whereas anti-inflammatory cytokines (IL-4, IL-10, IL-13, TGF) are involved in the development of anti-inflammatory reactions and inhibit the synthesis of pro-inflammatory interleukins.

TABLE 23

Relative levels of pro-inflammatory cytokines IL-1β, IL-12 and IFN-γ in the serum of experimental animals (M ± m, n = 10)

|  | IL-1β | IL-12 | IFN-γ |
| --- | --- | --- | --- |
| Control | 19.08 ± 0.71 | 8.25 ± 1.03 | 16.22 ± 0.35 |
| Diabetes | 26.16 ± 0.51* | 11.4 ± 1.85* | 18.56 ± 0.63* |
| Diabetes + zinc | 22.27 ± 0.92*# | 8.83 ± 1.65# | 15.24 ± 0.28*# |

*$p < 0.05$ versus the control group
$p < 0.05$ versus type I diabetes group

One of the controlling mechanisms for the levels and, accordingly, the biological effects of pro-inflammatory cytokines is implemented by a group of anti-inflammatory cytokines that includes IL-4, IL-10, IL-13, TGFβ. Cytokine imbalance is not only the basis for the occurrence of inflammatory processes, but it also determines the further form of the immune response, in particular whether it will be a predominantly cellular or humoral immune response. These cytokines are able to inhibit the synthesis of pro-inflammatory cytokines by affecting transcription of specific genes in producer cells, induce the synthesis of interleukin 1 receptor antagonists, enhance the production of soluble receptors and reduce the density of pro-inflammatory receptors on cells. Thus, IL-4 И IL-10 inhibit production of PGE2, super and nitroxide radicals, and block the formation of IL-1, IL-6, IL-8, TNF, inhibit the synthesis of IL-2, IFN-γ in lymphocytes.

TABLE 24

Relative levels of anti-inflammatory cytokines IL-4, IL-10 та TGF-β in the serum of experimental animals (M ± m, n = 10)

|  | IL-4 | IL-10 | TGF-β |
| --- | --- | --- | --- |
| Control | 2.41 ± 1.22 | 1.23 ± 1.05 | 3.22 ± 0.35 |
| Diabetes | 5.97 ± 0.57* | 8.83 ± 0.25* | 5.56 ± 0.63* |
| Diabetes + zinc | 6.42 ± 0.61* | 14.93 ± 0.56*# | 8.24 ± 0.28*# |

*$p < 0.05$ versus the control group
$p < 0.05$ versus type I diabetes group

The results of this study showed a certain positive effect of $Zn^{64}$ Aspartate on the cytokine profile, which can be regarded as a factor that normalizes an inflammatory process that occurs in the body during the development of type I diabetes.

Summarizing Results of the Study

The present study into the potential effects of the test substance on the glucose metabolism and related processes have shown the prospects of its use to normalize glucose metabolism in the body in patients developing type I diabetes. Presumably it can be used as an independent agent, as well as in combination with other drugs.

Intraperitoneal route of administration of the test substance is not suitable as a potential regulator of glucose metabolism. Oral administration showed a much better effect and led to a decrease in the glucose levels in the control animals.

The results show that zinc isotope, as compared with zinc acetate (natural zinc), either has a more prolonged effect on insulin levels in blood serum or is more slowly released from the sites of its deposition, and this also causes a slower effect of increasing insulin levels.

The results of microscopic examination indicate that the administration of zinc preparations, zinc isotope in particular, leads to an increase in the area of pancreatic islets, which in its turn may indicate the possibility of increasing insulin production by these islets. This is a move in the right direction, since the development of type 1 diabetes is associated with a significant insulin deficiency due to problems with its synthesis by these islets. The results obtained correlate with the results from the analysis of insulin levels in serum of the laboratory animals.

The glucose tolerance test showed a significant decrease in glucose levels after administration of zinc isotope $^{64}Zn$ as compared to the control group. This may indicate the influence of administered test substance on the insulin levels in the bloodstream, which in turn results in triggering mechanisms associated with clearing glucose from the blood. Given that insulin is a zinc-dependent protein, it can be assumed that the administration of zinc causes either an increase in the activity of this protein relative to its receptor in tissues or an increase in the amount of this hormone in the bloodstream.

The results obtained using a type I diabetes model may indicate that this test substance has a positive effect on the course of type I diabetes and may be used as a prophylactic agent to reduce the toxic effects of increased glucose levels in the bloodstream during the development of this pathology.

The results of this study showed a certain positive effect of $Zn^{64}$ Aspartate on the cytokine profile, which can be regarded as a factor that normalizes an inflammatory process that occurs in the body during the development of type I diabetes.

Based on mathematical model of a stable system, mass-spectrometry experimental data and analysis of the literature sources, the change of amino acids chirality in proteins with subsequent violation of proteins conformation and defects in DNA are the result of distortion in helixes because of stable isotopes substitution. There is a strong evidence to suggest that the isotope composition of the same chemical elements affects chemical bonds formation in solenoidal/helical structures of biomolecules. Isotope induced changes in biomolecules conformation appear to represent the onset of pathologies. But the most important feature of such changes is their reversibility. Conformation of biomolecules can be corrected with the modulation of isotope ratios of elements they are made from. Perfect conformation of proteins means perfect healthy/youthful homeostasis. It allows for complex effect on pathological changes in cells, tissues, organs and organism with immune, endocrine and nervous systems all mobilized against degenerative diseases. Isotope selective therapy can be the next step after treatment strategy based on molecular signatures.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A method of treating type I diabetes comprising administering to a subject in need thereof a therapeutically effective amount of a composition comprising a $^{64}Zn_e$ compound or a salt thereof, wherein the $^{64}Zn_e$ compound or a salt thereof is at least 80% $^{64}Zn_e$.

2. The method of claim 1, further comprising a diluent or an excipient.

3. The method of claim 2, wherein the diluent is deuterium-depleted water.

4. The method of claim 1, wherein the $^{64}Zn_e$ compound or a salt thereof is at least 95% $^{64}Zn_e$.

5. The method of claim 1, wherein the $^{64}Zn_e$ compound or a salt thereof is at least 99% $^{64}Zn_e$.

6. The method of claim 1, wherein the composition contains between 0.05 mg and 110 mg of $^{64}Zn_e$.

7. The method of claim 6, wherein the composition contains between 1 and 10 mg of $^{64}Zn_e$.

8. The method of claim 1, wherein the $^{64}Zn_e$ compound or a salt thereof is at least 90% $^{64}Zn_e$ and the composition is an aqueous solution in which $^{64}Zn_e$ is present at a concentration of between 0.1 mg/ml and 10 mg/ml.

9. The method of claim 1, wherein $^{64}Zn_e$ is in a form of a salt of asparaginate (chemical formula—$C_4H_5O_4N^{64}Zn_e$) with 2 aspartic acid molecules.

10. The method of claim 1, wherein the composition is administered by injection.

11. The method of claim 1, wherein the composition is administered orally.

* * * * *